(12) United States Patent
Lu et al.

(10) Patent No.: US 9,700,047 B2
(45) Date of Patent: Jul. 11, 2017

(54) MACROCYCLIC PICOLINAMIDES AS FUNGICIDES

(71) Applicant: Dow AgroSciences LLC, Indianapolis, IN (US)

(72) Inventors: Yu Lu, Indianapolis, IN (US); Timothy A. Boebel, Indianapolis, IN (US); Fangzheng Li, Indianapolis, IN (US); Karla Bravo-Altamirano, Indianapolis, IN (US); John F. Daeuble, Sr., Indianapolis, IN (US); Chenglin Yao, Indianapolis, IN (US); Kevin G. Meyer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/036,321

(22) PCT Filed: Apr. 30, 2015

(86) PCT No.: PCT/US2015/028407
§ 371 (c)(1),
(2) Date: May 12, 2016

(87) PCT Pub. No.: WO2015/171408
PCT Pub. Date: Nov. 12, 2015

(65) Prior Publication Data
US 2017/0055528 A1    Mar. 2, 2017

Related U.S. Application Data

(60) Provisional application No. 61/989,149, filed on May 6, 2014.

(51) Int. Cl.
| | | |
|---|---|---|
| A01N 43/40 | (2006.01) | |
| C07D 405/12 | (2006.01) | |
| C07D 313/00 | (2006.01) | |
| A01N 43/22 | (2006.01) | |
| A01N 47/36 | (2006.01) | |
| A01N 37/44 | (2006.01) | |
| A01N 43/54 | (2006.01) | |
| A01N 43/653 | (2006.01) | |
| A01N 43/88 | (2006.01) | |
| A01N 47/18 | (2006.01) | |
| A01N 47/24 | (2006.01) | |
| A01N 61/00 | (2006.01) | |

(52) U.S. Cl.
CPC .......... *A01N 43/40* (2013.01); *A01N 37/44* (2013.01); *A01N 43/22* (2013.01); *A01N 43/54* (2013.01); *A01N 43/653* (2013.01); *A01N 43/88* (2013.01); *A01N 47/18* (2013.01); *A01N 47/24* (2013.01); *A01N 47/36* (2013.01); *A01N 61/00* (2013.01); *C07D 313/00* (2013.01); *C07D 405/12* (2013.01)

(58) Field of Classification Search
CPC ...................................................... A01N 43/40
USPC ....................................................... 549/266
See application file for complete search history.

(56) References Cited

U.S. PATENT DOCUMENTS

| | | | |
|---|---|---|---|
| 6,355,660 B1 | 3/2002 | Ricks et al. | |
| 6,521,622 B1 | 2/2003 | Ricks et al. | |
| 6,706,740 B2 | 3/2004 | Ricks et al. | |
| 6,861,390 B2 | 3/2005 | Meyer et al. | |
| 6,916,932 B2 | 7/2005 | Meyer et al. | |
| 6,927,225 B2 | 8/2005 | Ricks et al. | |
| 7,034,035 B2 | 4/2006 | Ricks et al. | |
| 7,183,278 B1 | 2/2007 | Imamura et al. | |
| 7,250,389 B1 | 7/2007 | Sakanaka et al. | |
| 8,785,479 B2 | 7/2014 | Meyer et al. | |
| 8,835,462 B2 | 9/2014 | Meyer et al. | |
| 8,883,811 B2 | 11/2014 | Owen et al. | |
| 9,265,253 B2 | 2/2016 | Li et al. | |
| 2002/0177578 A1 | 11/2002 | Ricks et al. | |
| 2003/0018012 A1 | 1/2003 | Ricks et al. | |
| 2003/0018052 A1 | 1/2003 | Ricks et al. | |
| 2003/0022902 A1 | 1/2003 | Ricks et al. | |
| 2003/0022903 A1 | 1/2003 | Ricks et al. | |
| 2004/0034025 A1 | 2/2004 | Ricks et al. | |
| 2004/0048864 A1 | 3/2004 | Ricks et al. | |
| 2004/0171838 A1 | 9/2004 | Meyer et al. | |
| 2004/0186296 A1 | 9/2004 | Niyaz et al. | |
| 2004/0192924 A1 | 9/2004 | Meyer et al. | |

(Continued)

FOREIGN PATENT DOCUMENTS

| | | |
|---|---|---|
| EP | 1054011 | 11/2000 |
| EP | 1516874 | 3/2005 |

(Continued)

OTHER PUBLICATIONS

Gisi, U., The American Phytopathological Society, vol. 86, No. 11, 1996, p. 1273.

(Continued)

*Primary Examiner* — Taofiq A Solola
(74) *Attorney, Agent, or Firm* — Charles W. Arnett; Faegre Baker Daniels LLP

(57) ABSTRACT

This disclosure relates to macrocyclic picolinamides of Formula (I) and their use as fungicides.

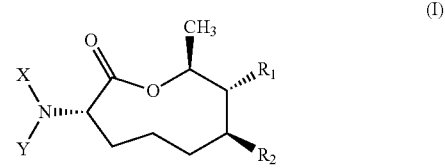

23 Claims, No Drawings

(56) References Cited

U.S. PATENT DOCUMENTS

| | | |
|---|---|---|
| 2005/0239873 A1 | 10/2005 | Hockenbery et al. |
| 2006/0040995 A1 | 2/2006 | Bacque et al. |
| 2007/0060579 A1 | 3/2007 | Wachendorff-Neumann et al. |
| 2007/0066629 A1 | 3/2007 | Tormo i Biasco et al. |
| 2008/0070985 A1 | 3/2008 | Derrer et al. |
| 2008/0293798 A1 | 11/2008 | Dietz |
| 2008/0318785 A1 | 12/2008 | Koltzenburg |
| 2009/0203770 A1 | 8/2009 | Hockenberry et al. |
| 2009/0306142 A1 | 12/2009 | Carson et al. |
| 2011/0034493 A1 | 2/2011 | Boebel et al. |
| 2011/0053891 A1 | 3/2011 | Boebel et al. |
| 2011/0053966 A1 | 3/2011 | Klittich et al. |
| 2011/0082039 A1 | 4/2011 | Keeney et al. |
| 2011/0082160 A1 | 4/2011 | Owen |
| 2011/0082162 A1 | 4/2011 | Lorsbach et al. |
| 2011/0306644 A1 | 12/2011 | Hoekstra et al. |
| 2012/0035054 A1 | 2/2012 | Ehr et al. |
| 2012/0245031 A1 | 9/2012 | Gewehr et al. |
| 2013/0090298 A1 | 4/2013 | Lee et al. |
| 2013/0296371 A1 | 11/2013 | Meyer et al. |
| 2013/0296372 A1 | 11/2013 | Owen et al. |
| 2013/0296373 A1 | 11/2013 | Meyer |
| 2013/0296374 A1 | 11/2013 | Owen et al. |
| 2013/0296375 A1 | 11/2013 | Meyer et al. |
| 2014/0187587 A1 | 7/2014 | Ouimette et al. |
| 2014/0187588 A1 | 7/2014 | Lalonde et al. |
| 2014/0187590 A1 | 7/2014 | Ouimette et al. |
| 2014/0275171 A1 | 9/2014 | Meyer, Jr. et al. |
| 2015/0065529 A1 | 3/2015 | Owen, Jr. et al. |
| 2015/0094341 A1 | 4/2015 | Li et al. |
| 2015/0183759 A1 | 7/2015 | DeLorbe et al. |

FOREIGN PATENT DOCUMENTS

| | | |
|---|---|---|
| WO | WO 01/014365 | 3/2001 |
| WO | WO 0114339 | 3/2001 |
| WO | WO 03/011857 | 2/2003 |
| WO | WO 03/035617 | 5/2003 |
| WO | WO 2007017416 | 2/2007 |
| WO | WO 2009040397 | 9/2008 |
| WO | WO 2011028657 | 3/2011 |
| WO | WO 2011044213 | 4/2011 |
| WO | WO 2011069893 | 6/2011 |
| WO | WO 2012/016972 | 2/2012 |
| WO | WO 2012016989 | 2/2012 |
| WO | WO 2012070015 | 5/2012 |
| WO | WO 2013/110002 | 7/2013 |
| WO | WO 2013/116251 | 8/2013 |
| WO | WO 2015/103161 | 7/2015 |

OTHER PUBLICATIONS

Huang, et al., Synergistic Interactions between Chitinase ChiCW and Fungicides Against Plant Fungal Pathogens, J. Microbiol. Biotechnol., 2008, 18(4) 784-787.

Backman, P., Fungicide Formulation: Relationship to Biological Activity, 1978, 16, 211-237.

Latin, et al, Re-Examining Fungicide Synergism for Dollar Spot Control, GCM, 2008, 84-87.

O'Sullivan, et al., Fungicide Resistance—an Increasing Problem, Proceedings of National Tillage Conference 2007, Published by Crop Research Centre Oak Park Carlow, date Jan. 31, 2007, 14 pages.

Koyanagi et al., "Bioisoterism, etc.," Synthesis and Chemistry of Agrochemicals IV; Baker, D. et al., 1995, 15-24.

Masashi Ueki et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-634.

K. Tani et al., Journal of Antibiotics, vol. 55, No. 3, Mar. 2002, pp. 315-321.

Y. Usuki et al., Journal of Antibiotics, vol. 55, No. 6, Jun. 2002, pp. 607-610.

Anonymous, Synergistic Fungicidal Composition of Heterocyclic Aromatic Amides and Triazoles, IP.COM, Electronic Publication, 2004, 11 pages.

Anonymous, Synergistic Fungicidal Composition of Heterocyclic Aromatic Amides and Triazoles, IP.COM Journal, IP.COM, Inc., West Henrietta, NY, US, Jul. 2004, 10 pages.

Z. Hu et al., Synthesis of Novel Analogues of Antimycin A3, Tetrahedron Letters 49 (2008), pp. 5192-5195.

Usuki, et al., "Semi-synthesis and biological evaluation of analogues of UK-2A, a novel antifungal antibiotic from *Steptomyces* sp. 517-02," Bioorganic & Medicinal Chemistry Letters, Pergamon, Amsterdam, KL, vol. 15, No. 8, Apr. 15, 2005, pp. 2011-2014, XP027801790.

Pubchem, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.

International Searching Authority, International Search Report and Written Opinion for PCT/US2015/028407, dated Aug. 5, 2015, 8 pages.

MACROCYCLIC PICOLINAMIDES AS FUNGICIDES

CROSS-REFERENCE TO RELATED APPLICATIONS

This application is a U.S. National Phase Patent Application based on International Application No. PCT/US2015/028407 filed Apr. 30, 2015, which claims the benefit of U.S. Provisional Patent Application Ser. No. 61/989,149 filed May 6, 2014, which is expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

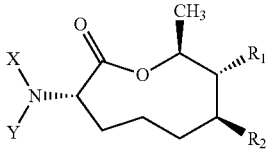

I wherein
X is hydrogen or C(O)R$_3$;
Y is hydrogen, C(O)R$_3$, or Q;
Q is

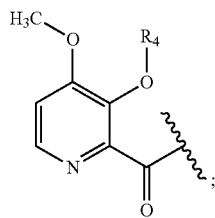

R$_1$ and R$_2$ are independently selected from the group consisting of hydrogen, alkyl, alkenyl, and aryl, each optionally substituted with 0, 1 or multiple R$_6$;
R$_3$ is alkoxy or benzyloxy, each optionally substituted with 0, 1, or multiple R$_6$;
R$_4$ is hydrogen, —C(O)R$_5$, or —CH$_2$OC(O)R$_5$;
R$_5$ is alkyl, alkoxy, or aryl, each optionally substituted with 0, 1, or multiple R$_6$;
R$_6$ is hydrogen, alkyl, aryl, halo, acyloxy, alkenyl, alkoxy, heteroaryl, heterocyclyl, or thioalkyl, each optionally substituted with 0, 1, or multiple R$_7$; and
R$_7$ is hydrogen, alkyl, aryl, or halo.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl, and the like.

The terms "aryl" and "Ar" refer to any aromatic ring, mono- or bi-cyclic, containing 0 heteroatoms.

The term "heterocycle" refers to any aromatic or non-aromatic ring, mono- or bi-cyclic, containing one or more heteroatoms The term "alkoxy" refers to an —OR substituent.
The term "acyloxy" refers to an —OC(O)R substituent.
The term "cyano" refers to a —C≡N substituent.
The term "hydroxyl" refers to an —OH substituent.
The term "amino" refers to a —N(R)$_2$ substituent.
The term "arylalkoxy" refers to —O(CH$_2$)$_n$Ar where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —NO$_2$ substituent.
The term thioalkyl refers to an —SR substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendable, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzovindiflupyr benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, niflurdide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, taufluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; anamorph: *Septoria tritici*), wheat brown rust (*Puccinia triticina*), wheat stripe rust (*Puccinia strhformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f sp. *tritici*), powdery mildew of barley (*Blumeria graminis* f sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formula 1.3, where $R_1$ and $R_2$ are as originally defined, can be prepared according to the methods outlined in Scheme 1, steps a-c. Compounds of Formula 1.1, where $R_1$ is as originally defined, can be obtained by reaction of (S)-5-methylfuran-2(5H)-one, a compound of Formula 1.0 (prepared as in Kobayashi et al. *Tetrahedron* 2003, 59, 9743-9758) with an organolithium reagent, such as $R_1Li$, or a Grignard reagent, such as $R_1MgX$, where $R_1$ is as originally defined and X is bromide or chloride, and copper (I) iodide in a solvent such as tetrahydrofuran (THF) at cryogenic temperatures such as −78° C., as shown in a. Compounds of Formula 1.2, where $R_1$ and $R_2$ are as originally defined, can be obtained by treating compounds of Formula 1.1, where $R_1$ is as originally defined, with lithium diisopropylamide (LDA), which was generated in situ from n-butyllithium (n-BuLi) and diisopropylamine (i-Pr$_2$NH) at −20° C., followed by reacting with alkyl or benzyl bromide or alkyl or benzyl chloride, such as $R_2Br$, where $R_2$ is as originally defined, in a solvent such as THF from −78° C. to ambient temperature, as shown in b. Compounds of Formula 1.3, where $R_1$ and $R_2$ are as originally defined, can be prepared from compounds of Formula 1.2, where $R_1$ and $R_2$ are as originally defined, by treating with a reducing agent such as lithium aluminum hydride (LiAlH$_4$, LAH), in a solvent such as THF from 0° C. to ambient temperature, as depicted in c.

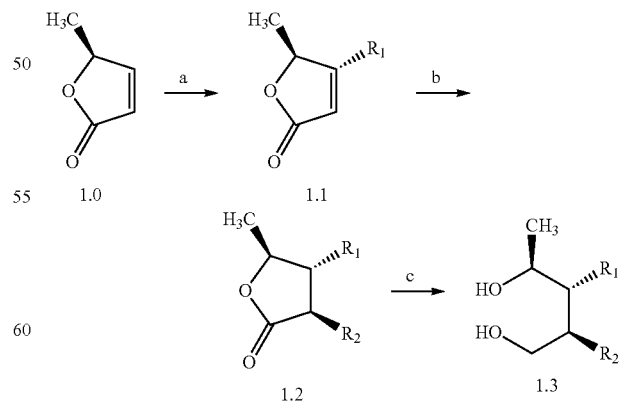

Scheme 1

Compounds of Formula 2.3, where $R_1$ and $R_2$ are as originally defined, can be prepared as shown in Scheme 2, steps a-d. Diols of Formula 1.3, where $R_1$ and $R_2$ are as originally defined, can be protected as bis-trimethylsilyl (TMS) ethers to give compounds of Formula 2.0, where $R_1$ and $R_2$ are as originally defined, by reacting with a base such as triethylamine ($Et_3N$) and silylating reagent, such as chloro trimethylsilane (TMSCl), in an aprotic solvent, such as dichloromethane (DCM), at ambient temperature, as shown in a. Compounds of Formula 2.1, where $R_1$ and $R_2$ are as originally defined, can be obtained by reacting compounds of Formula 2.0, where $R_1$ and $R_2$ are as originally defined, with an oxidant, such as a solution of chromium trioxide ($CrO_3$) and pyridine, in a solvent such as DCM at low temperatures such as from $-25°$ C. to $-10°$ C., as shown in b. Compounds of Formula 2.2, where $R_1$ and $R_2$ are as originally defined, can be prepared by addition of compounds of Formula 2.1, where $R_1$ and $R_2$ are as originally defined, into a mixture of n-BuLi and bromo(methyl)-triphenylphosphorane ($Ph_3PBrCH_3$), in a solvent such as THF at cryogenic temperatures such as $-78°$ C., and slowly warming to ambient temperature, as shown in c. Compounds of Formula 2.3, where $R_1$ and $R_2$ are as originally defined, can be obtained from compounds of Formula 2.2, where $R_1$ and $R_2$ are as originally defined, by reacting with a base such as $Et_3N$, a catalyst such as N,N-dimethylpyridin-4-amine (DMAP), and acetylating reagent such as acetyl chloride (AcCl), in a solvent such as DCM at ambient temperature, as shown in d.

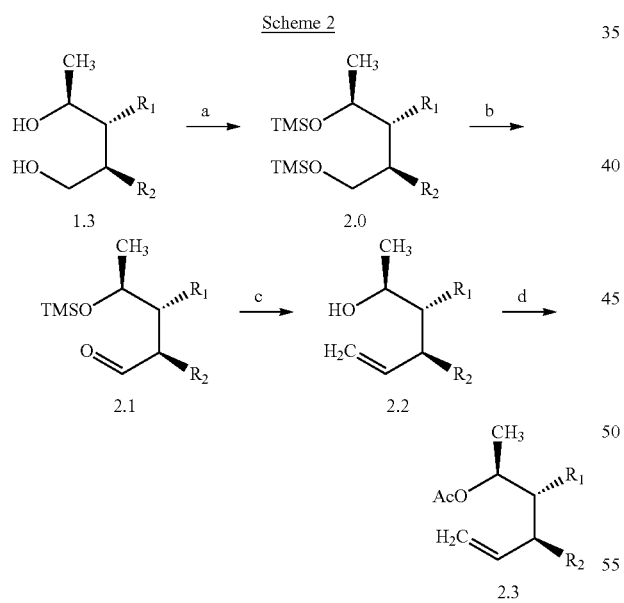

Scheme 2

Compounds of Formula 3.3, where $R_1$ and $R_2$ are as originally defined, can be prepared as outlined in Scheme 3, steps a-c. Compounds of Formula 3.1 can be prepared by treating compounds of Formula 2.3, where $R_1$ and $R_2$ are as originally defined, with an alkylborane reagent, such as 9-borabicyclo[3.3.1]nonane (9-BBN), in a solvent such as THF, at a temperature between ambient temperature and about 50° C., followed by treatment with an alkaline aqueous solution, such as aqueous potassium phosphate ($K_3PO_4$), a brominated olefin, such as a compound of Formula 3.0 (prepared as in Singh et al. *Org. Lett.* 2003, 17, 3155-3158), and a palladium catalyst, such as [1,1-bis(diphenylphosphino)ferrocene]dichloropalladium(II) [$PdCl_2(dppf)$] at ambient room temperature to about 55° C., as shown in step a. Compounds of the Formula 3.2, where $R_1$ and $R_2$ are as originally defined, can be prepared from enamides, generalized by Formula 3.1, where $R_1$ and $R_2$ are as originally defined, using an asymmetric hydrogenation reaction employing a catalyst such as (+)-1,2-bis((2S,5S)-2,5-diethylphospholano)benzene(1,5-cyclooctadiene) rhodium(I) trifluoromethanesulfonate ((S,S)-Et-DuPHOS-Rh) under a hydrogen gas ($H_2$) atmosphere at a pressure between 40 and 200 pounds per square inch (psi) in a solvent such as methanol (MeOH) as shown in step b. Compounds of Formula 3.3, where $R_1$ and $R_2$ are as originally defined, can be prepared from compounds of Formula 3.2, where $R_1$ and $R_2$ are as originally defined and the carboxylic acid is protected as either the methyl (Me) or benzyl (Bn) ester, by treating with a hydroxide base, such as lithium hydroxide monohydrate ($LiOH.H_2O$), in an aqueous MeOH solvent mixture, as shown in step c.

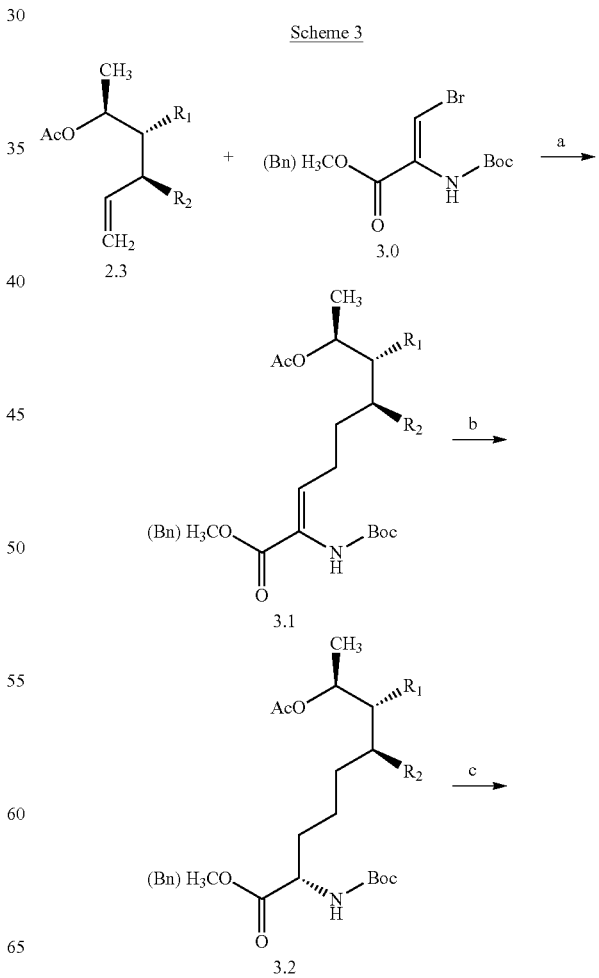

Scheme 3

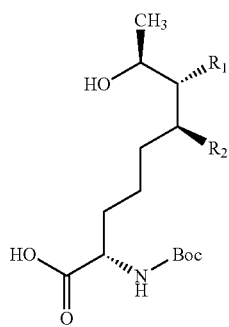

Compounds of Formula 4.0, where $R_1$ and $R_2$ are as originally defined, can be prepared according to the methods outlined in Scheme 4. Compounds of Formula 4.0, can be obtained from compounds of Formula 3.3, where $R_1$ and $R_2$ are as originally defined, by the addition of a solution of compounds of Formula 3.3 in a halogenated solvent such as DCM or an aromatic solvent such as toluene to a mixture of a base, such as DMAP, and a mixed anhydride, such as 2-methyl-6-nitrobenzoic anhydride (MNBA), in either a halogenated solvent such as DCM or an aromatic solvent such as toluene at a temperature between about 21° C. and about 60° C. over a period of 4-12 hours (h), as shown in step a.

Scheme 4

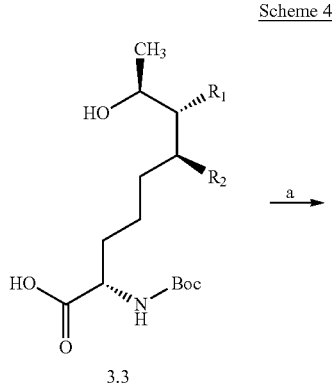

Compounds of Formula 5.1 can be prepared through the methods shown in Scheme 5, steps a-b. Compounds of Formula 5.0, where $R_1$ and $R_2$ are as originally defined and X and Y are hydrogen, can be obtained from compounds of Formula 4.0, where $R_1$ and $R_2$ are as originally defined, by treating with an acid, such as a 4.0 Molar (M) hydrogen chloride (HCl) solution in dioxane, in a solvent such as DCM, as shown in a. The resulting hydrochloride salt may be neutralized prior to use to give the free amine or neutralized in situ in step b. Compounds of Formula 5.1, where $R_1$ and $R_2$ are as originally defined, can be prepared from compounds of Formula 5.0, where $R_1$ and $R_2$ are as originally defined, by treatment with 3-hydroxy-4-methoxypicolinic acid in the presence of a base, such as 4-methylmorpholine, and a peptide coupling reagent, such as O-(7-azabenzotriazol-1-yl)-N,N,N',N'-tetramethyluronium hexafluorophosphate (HATU) or benzotriazol-1-yl-oxytripyrrolidinophosphonium hexafluorophosphate (Py-BOP), in an aprotic solvent such as DCM, as shown in b.

Scheme 5

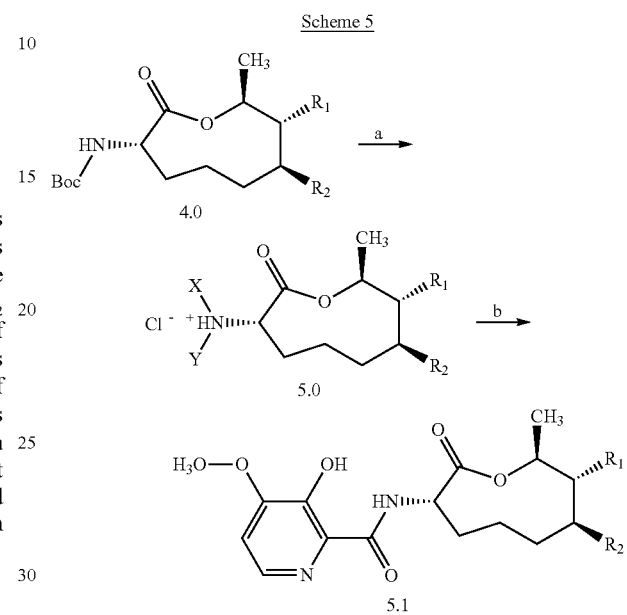

Compounds of Formula 6.0, where $R_1$, $R_2$ and $R_4$ are as originally defined, can be prepared by the method shown in Scheme 6. Compounds of Formula 6.0, where $R_1$ and $R_2$ are as originally defined, can be prepared from compounds of Formula 5.1, where $R_1$ and $R_2$ are as originally defined, by treatment with the appropriate alkyl halide with or without a reagent such as sodium iodide (NaI) and an alkali carbonate base such as sodium carbonate ($Na_2CO_3$) or potassium carbonate ($K_2CO_3$) in a solvent such as acetone or by treatment with an acyl halide in the presence of an amine base, such as pyridine, $Et_3N$, DMAP, or mixtures thereof in an aprotic solvent such as DCM, as shown in step a.

Scheme 6

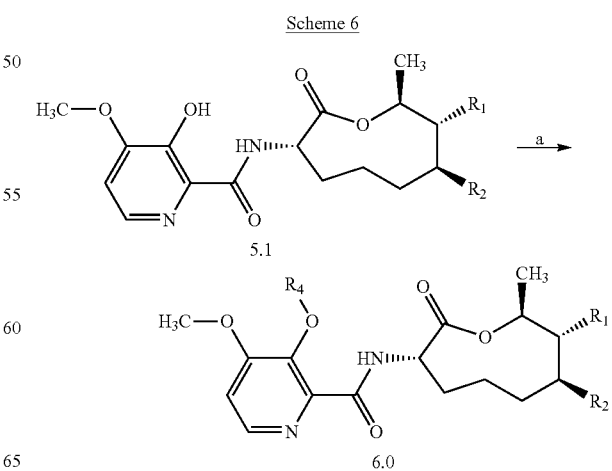

EXAMPLES

Example 1

Step 1

Preparation of
(4R,5S)-4-butyl-5-methyldihydrofuran-2(3H)-one

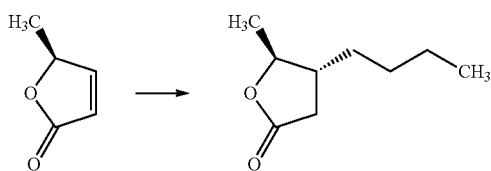

To a suspension of copper(I) iodide (6.08 grams (g), 31.9 millimole (mmol)) in 35 milliliters (mL) of diethyl ether (Et₂O) at −78° C. was added n-BuLi (2.5 Molar (M) in hexanes, 25.6 mL, 64.0 mmol) dropwise. After stirring between −30 and −20° C. for 30 minutes (min), the reaction mixture became a homogenous, dark brown solution. The solution was cooled to −78° C. and (S)-5-methylfuran-2 (5H)-one (2.09 g, 21.3 mmol) in Et₂O (8 mL) was added slowly. The reaction was stirred at −78° C. for 2 hours (h), at which time thin layer chromatography (TLC) analysis showed the reaction to be complete. The reaction was quenched with saturated aqueous ammonium chloride (NH₄Cl) and filtered through Celite® to remove the inorganic salts. The filtrate was extracted with Et₂O (3×), and the combined organic extracts were dried over sodium sulfate (Na₂SO₄), filtered, concentrated, and purified by flash chromatography (silica gel (SiO₂), 0→30% ethyl acetate (EtOAc) in hexanes) to provide the title compound (2.92 g, 88%) as a colorless oil: $^1$H NMR (400 MHz, CDCl₃) δ 4.21 (dq, J=7.6, 6.2 Hz, 1H), 2.68 (dd, J=17.4, 8.2 Hz, 1H), 2.22 (dd, J=17.4, 9.7 Hz, 1H), 2.14-2.00 (m, 1H), 1.62-1.49 (m, 1H), 1.40 (d, J=6.2 Hz, 3H), 1.38-1.26 (m, 5H), 0.91 (t, J=7.0 Hz, 3H); $^{13}$C NMR (101 MHz, CDCl₃) δ 176.51, 82.16, 43.27, 35.44, 32.11, 29.76, 22.55, 19.80, 13.82; [α]$_D$=−44.2° (a=−0.177, c=0.4, CDCl₃).

Example 1

Step 2

(3R,4R,5S)-3-benzyl-4-butyl-5-methyldihydrofuran-2(3H)-one

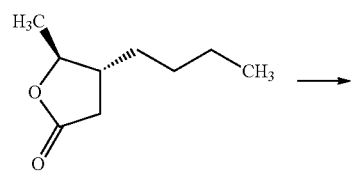

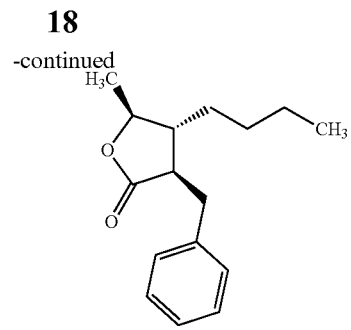

To a solution of diisopropylamine (958 microliters (μL), 6.84 mmol) in THF (11 mL) at −78° C. was added n-BuLi (2.5 M in hexanes, 2.74 mL, 6.85 mmol). The reaction was stirred at 0° C. for 15 min, cooled to −78° C., and treated with (4R,5S)-4-butyl-5-methyldihydrofuran-2(3H)-one (890 milligrams (mg), 5.70 mmol). The reaction was stirred at −78° C. for 30 min, treated with benzyl bromide (1016 μL, 8.55 mmol), and the resulting solution was slowly warmed to room temperature overnight. The reaction was quenched with saturated aqueous NH₄Cl and extracted with Et₂O (3×). The combined organic extracts were concentrated and the residue was purified by flash chromatography (SiO₂, 0→5% EtOAc in hexanes) to provide the title compound (950 mg, 67.7%) as a colorless oil: $^1$H NMR (400 MHz, CDCl₃) δ 7.38-7.10 (m, 5H), 4.12 (dq, J=8.2, 6.2 Hz, 1H), 3.12 (dd, J=14.0, 5.4 Hz, 1H), 2.98 (dd, J=14.0, 6.6 Hz, 1H), 2.63 (ddd, J=10.1, 6.6, 5.4 Hz, 1H), 1.81-1.73 (m, 1H), 1.33-1.26 (m, 2H), 1.26 (d, J=6.2 Hz, 3H), 1.22-1.12 (m, 4H), 0.85-0.79 (m, 3H); $^{13}$C NMR (101 MHz, CDCl₃) 178.11, 138.11, 129.37, 128.54, 126.69, 80.24, 67.96, 48.07, 46.82, 35.64, 31.70, 28.96, 25.61, 22.77, 20.72, 13.80.

Example 1

Step 3

Preparation of
(2R,3R,4S)-2-benzyl-3-butylpentane-1,4-diol

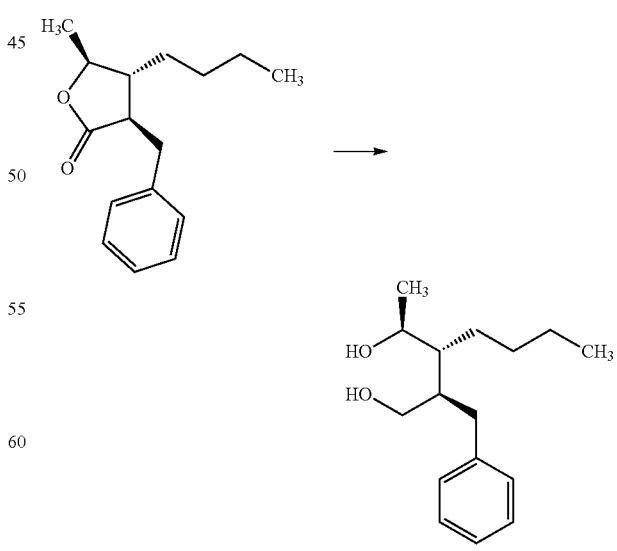

To a solution of (3R,4R,5S)-3-benzyl-4-butyl-5-methyl-dihydrofuran-2(3H)-one (700 mg, 2.84 mmol) in THF (14 mL) at 0° C. was added LAH (1 M in THF, 3.4 mL, 3.4 mmol) and the reaction was slowly warmed to room temperature overnight. TLC analysis showed complete consumption of the starting material (SM) along with the formation of a more polar spot (2:1 hexanes/EtOAc, $R_f$=0.2-0.3). The reaction was quenched by the careful addition of water (0.2 mL), 10% aqueous sodium hydroxide (NaOH, 0.4 mL), and additional water (0.6 mL). Solid $Na_2SO_4$ was added and the mixture was filtered to remove salts. The filter cake was washed with EtOAc and the combined organics were concentrated and the residue was purified by flash chromatography ($SiO_2$, 0→30% EtOAc in hexanes) to provide the title compound (660 mg, 93%) as a colorless, thick oil which solidified upon drying under vacuum: $^1$H NMR (400 MHz, $CDCl_3$) δ 7.35-7.10 (m, 5H), 3.88-3.79 (m, 1H), 3.69 (dt, J=11.1, 3.0 Hz, 1H), 3.49 (dt, J=11.1, 5.5 Hz, 1H), 3.40 (d, J=4.3 Hz, 1H), 3.35-3.23 (m, 1H), 2.82 (dd, J=13.6, 5.8 Hz, 1H), 2.74 (dd, J=13.6, 9.4 Hz, 1H), 2.03-1.94 (m, 1H), 1.53-1.41 (m, 1H), 1.36-1.22 (m, 6H), 1.26 (d, J=6.3 Hz, 3H), 0.88-0.84 (m, 3H); $^{13}$C NMR (101 MHz, $CDCl_3$) δ 141.72, 129.17, 128.30, 125.81, 70.00, 61.40, 46.88, 44.46, 37.01, 30.52, 29.84, 23.01, 22.52, 14.07; ESIMS m/z 501.4 ($[2M+Na]^+$).

Example 2

Steps 1a-1c

Preparation of (2S,3R)-3-((S)-1-phenylbut-3-en-2-yl)heptan-2-ol

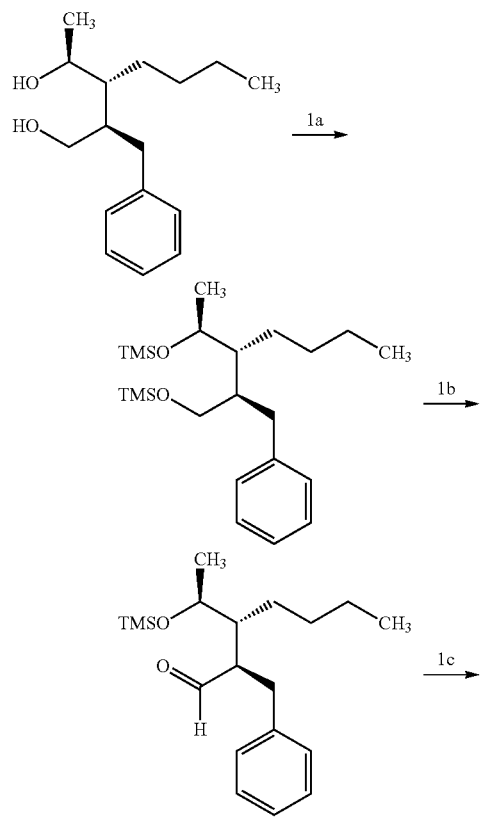

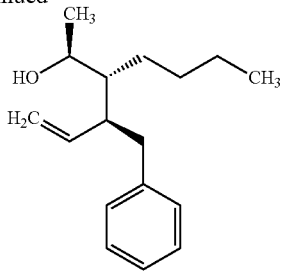

Step 1a

Preparation of (4S,5R,6R)-6-benzyl-5-butyl-2,2,4,9,9-pentamethyl-3,8-dioxa-2,9-disiladecane To a solution of (2R,3R,4S)-2-benzyl-3-butylpentane-1,4-diol (470 mg, 1.88 mmol) and $Et_3N$ (1308 μL, 9.39 mmol) in DCM (10 mL) at room temperature was added chlorotrimethylsilane (596 μL, 4.69 mmol). The reaction was stirred at room temperature for 1 hr, diluted with hexane (20 mL), and the resulting salts were removed by filtration through Celite®. The cake was washed with 20:1 hexanes/EtOAc and the organics were concentrated to provide a colorless oil: $^1$H NMR (400 MHz, $CDCl_3$) δ 7.29-7.14 (m, 5H), 4.05 (qd, J=6.3, 3.7 Hz, 1H), 3.42 (dd, J=10.1, 4.4 Hz, 1H), 3.35 (dd, J=10.1, 7.6 Hz, 1H), 3.03 (dd, J=13.5, 3.4 Hz, 1H), 2.23 (dd, J=13.4, 10.7 Hz, 1H), 2.14-1.96 (m, 1H), 1.54 (d, J=4.0 Hz, 1H), 1.41-0.21 (m, 6H), 1.19 (d, J=6.3 Hz, 3H), 1.02-0.79 (m, 3H), 0.01 (s, 9H), 0.00 (s, 9H).

Step 1b

Preparation of (2R,3R)-2-benzyl-3-((S)-1-((trimethylsilyl)oxy)-ethyl)heptanal

To a suspension of $CrO_3$ (563 mg, 5.63 mmol) in DCM (15 mL) at room temperature was added pyridine (907 μL, 11.26 mmol), and the solution was stirred at room temperature for 30 min, cooled to −25° C., treated with a solution of (4S,5R,6R)-6-benzyl-5-butyl-2,2,4,9,9-pentamethyl-3,8-dioxa-2,9-disiladecane (742 mg, 1.88 mmol) in DCM (5 mL), and stirred between −25 and −10° C. for 2 h. The resulting solution was filtered through a plug of $SiO_2$ to remove inorganic salts and the plug was washed with 10:1 hexanes/EtOAc. The resulting colorless solution was concentrated to give a colorless oil: $^1$H NMR (400 MHz, $CDCl_3$) δ 9.55 (d, J=1.5 Hz, 1H), 7.19-7.03 (m, 5H), 3.80 (p, J=6.1 Hz, 1H), 2.91-2.74 (m, 3H), 1.71 (qd, J=6.0, 3.4 Hz, 1H), 1.38-1.17 (m, 6H), 1.13 (d, J=6.2 Hz, 3H), 0.78 (t, J=7.0 Hz, 3H), 0.00 (s, 9H).

Step 1c

Preparation of (2S,3R)-3-((S)-1-phenylbut-3-en-2-yl)heptan-2-ol

To a suspension of $Ph_3PBrCH_3$ (1.68 g, 4.69 mmol) in THF (8 mL) at 0° C. was added n-BuLi (2.5 M in hexane, 1.8 mL, 4.51 mmol) dropwise. The reaction mixture turned from a cloudy, white mixture to a homogeneous, yellow solution. The solution was stirred for 30 min at 0° C., cooled to −78° C., and treated with (2R,3R)-2-benzyl-3-((S)-1-((trimethylsilyl)oxy)ethyl)heptanal (602 mg, 1.88 mmol) in THF (2 mL). The reaction mixture was slowly warmed to room temperature overnight, quenched with water, and the pH was adjusted to 1 by the addition of 1 Normal (N) aqueous hydrogen chloride (HCl). The acidic solution was stirred for 10 min, extracted with Et$_2$O (3×), and the combined organic phases were dried over Na$_2$SO$_4$, filtered, and concentrated. The residue was purified by flash chromatography (SiO$_2$, 0→10% EtOAc in hexanes) to provide the title compound (247 mg, 53% over 3 steps) as a colorless oil: IR (neat) 3389, 3063, 2929, 1454 cm$^{-1}$; $^1$H NMR (400 MHz, CDCl$_3$) δ 7.32-7.10 (m, 5H), 5.78 (ddd, J=17.2, 10.3, 8.5 Hz, 1H), 4.98-4.77 (m, 2H), 3.90 (pd, J=6.2, 4.8 Hz, 1H), 2.95 (dd, J=13.4, 5.0 Hz, 1H), 2.63 (dd, J=13.4, 9.3 Hz, 1H), 2.51 (tt, J=9.2, 4.8 Hz, 1H), 1.50-1.40 (m, 1H), 1.40-1.23 (m, 6H), 1.20 (d, J=6.3 Hz, 3H), 0.94-0.85 (m, 3H); $^{13}$C NMR (101 MHz, CDCl$_3$) δ 141.24, 140.70, 129.26, 128.07, 125.69, 115.57, 69.34, 48.89, 47.09, 38.57, 31.07, 27.64, 23.11, 21.07, 14.07.

Example 2

Step 2

Preparation of (2S,3R)-3-((S)-1-phenylbut-3-en-2-yl)heptan-2-yl acetate

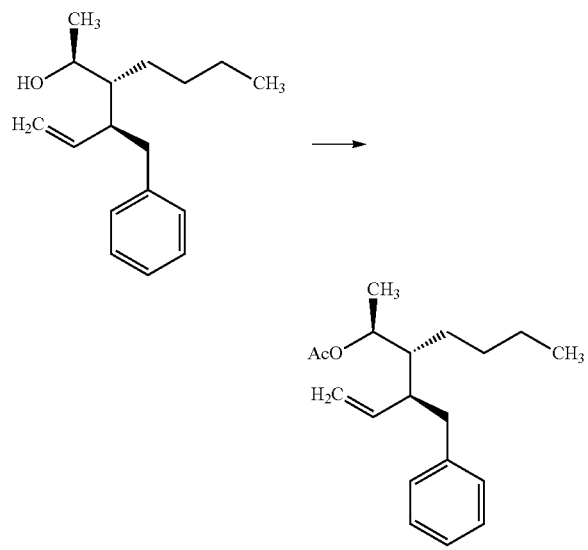

To a solution of (2S,3R)-3-((S)-1-phenylbut-3-en-2-yl)heptan-2-ol (247 mg, 1.00 mmol) in DCM (5 mL) at room temperature were added Et$_3$N (391 μL, 2.80 mmol), acetic anhydride (177 μL, 1.869 mmol) and DMAP (22.84 mg, 0.187 mmol). The reaction was stirred at room temperature for 2 h, quenched with saturated aqueous sodium bicarbonate (NaHCO$_3$), extracted with DCM (3×), and the combined organic phases were dried over Na$_2$SO$_4$, filtered, and concentrated. The residue was purified by flash chromatography (SiO$_2$, 0→10% EtOAc in hexanes) to provide the title compound (256 mg, 95%) as a colorless oil: IR (neat) 3027, 2931, 1733, 1240 cm$^{-1}$; $^1$H NMR (400 MHz, CDCl$_3$) δ 7.31-7.08 (m, 5H), 5.66 (ddd, J=17.1, 10.3, 8.7 Hz, 1H), 5.10-5.01 (m, 1H), 4.94 (ddd, J=10.3, 1.8, 0.6 Hz, 1H), 4.77 (ddd, J=17.1, 1.9, 1.0 Hz, 1H), 2.93 (dd, J=13.5, 4.8 Hz, 1H), 2.56 (dd, J=13.4, 9.6 Hz, 1H), 2.47-2.36 (m, 1H), 2.05 (s, 3H), 1.68-1.58 (m, 1H), 1.45-1.22 (m, 6H), 1.20 (d, J=6.4 Hz, 3H), 0.95-0.84 (m, 3H); $^{13}$C NMR (101 MHz, CDCl$_3$) δ 170.41, 140.98, 139.68, 129.22, 128.04, 125.72, 115.99, 72.04, 47.21, 45.80, 38.44, 30.83, 27.32, 22.92, 21.54, 17.18, 14.01.

Example 3

Step 1

Preparation of (6R,7R,Z)-methyl 7-((S)-1-acetoxyethyl)-6-benzyl-2-((tert-butoxycarbonyl)amino)undec-2-enoate

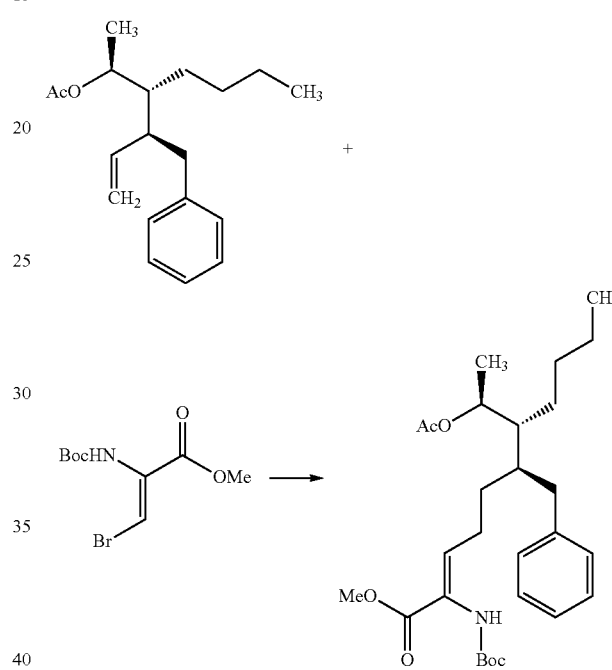

To a solution of (2S,3R)-3-((S)-1-phenylbut-3-en-2-yl) heptan-2-yl acetate (252 mg, 0.874 mmol) in THF (2.3 mL) was added 9-BBN (0.5 M in THF, 2272 μL, 1.136 mmol), and the reaction was stirred at room temperature for 30 min, warmed to 50° C., and stirred at 50° C. for 2 h. The reaction mixture was cooled to room temperature, treated with K$_3$PO$_4$ (582 μL, 1.75 mmol) followed by a solution of (4-methyl 3-bromo-2-((tert-butoxycarbonyl)amino)acrylate (269 mg, 0.961 mmol) in N,N-dimethylformamide (DMF; 4369 μL), and PdCl$_2$(dppf) (32.0 mg, 0.044 mmol). The reaction mixture was heated to 55° C. and stirred overnight. The reaction was quenched by the addition of saturated aqueous NaHCO$_3$ solution (10 mL), extracted with Et$_2$O (3×), and the combined organic phases were dried over Na$_2$SO$_4$ filtered, and concentrated. The residue was purified by flash chromatography (SiO$_2$, 0→15% EtOAc in hexanes) to give the title compound (310 mg, 72.5%) as a colorless oil: $^1$H NMR (400 MHz, CDCl$_3$) δ 7.33-7.09 (m, 5H), 6.37 (t, J=7.2 Hz, 1H), 5.95 (s, 1H), 5.10 (p, J=6.3 Hz, 1H), 3.74 (s, 3H), 2.88 (dd, J=13.5, 4.5 Hz, 1H), 2.30 (dd, J=13.5, 9.8 Hz, 1H), 2.25-2.10 (m, 1H), 2.09-1.99 (m, 1H), 2.06 (s, 3H), 1.88-1.82 (m, 1H), 1.59-1.51 (m, 1H), 1.45 (s, 9H), 1.43-1.21 (m, 8H), 1.26 (d, J=6.3 Hz, 3H), 0.97-0.81 (m, 3H); $^{13}$C NMR (101 MHz, CDCl$_3$) δ 170.55, 165.30, 153.17, 141.66, 136.33, 129.10, 128.29, 125.79, 80.41, 71.93, 52.23, 43.77, 40.24, 37.37, 31.16, 29.48, 28.17, 26.43, 23.03, 21.40, 18.56, 14.01; ESIMS m/z 512.3 ([M+Na]').

Example 3

Step 2

Preparation of (2S,6R,7R)-methyl 7-((S)-1-acetoxyethyl)-6-benzyl-2-((tert-butoxycarbonyl)amino)undecanoate

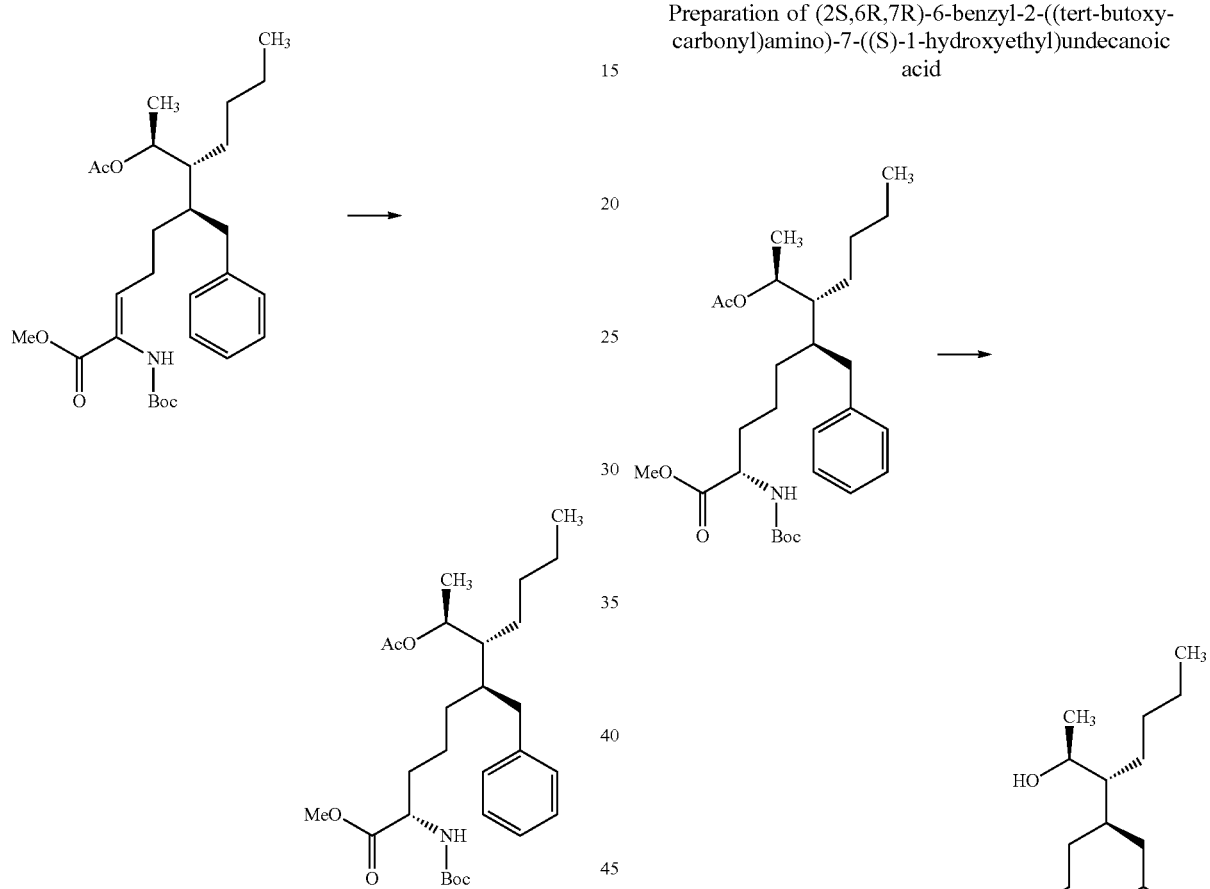

A solution of (6R,7R,Z)-methyl 7-((S)-1-acetoxyethyl)-6-benzyl-2-((tert-butoxycarbonyl)amino)undec-2-enoate (364 mg, 0.743 mmol) in anhydrous MeOH (15 mL) was sparged with nitrogen gas (N₂) for 10 min in a stainless steel reactor and then treated with (S,S)-Et-DuPHOS-Rh (5.37 mg, 7.43 μmol). The reactor was sealed, purged twice with 200 psi of hydrogen gas (H₂), pressurized to 200 psi with H₂, and the mixture was stirred at room temperature overnight. The reaction was concentrated and purified by flash chromatography (SiO₂, 0→30% EtOAc in hexanes) to provide the title compound (324 mg, 87%) as a colorless oil: ¹H NMR (400 MHz, CDCl₃) δ 7.39-7.05 (m, 5H), 5.08 (p, J=6.3 Hz, 1H), 4.92 (d, J=8.5 Hz, 1H), 4.22 (q, J=7.2 Hz, 1H), 3.70 (s, 3H), 2.86 (dd, J=13.5, 4.6 Hz, 1H), 2.27 (dd, J=13.5, 9.7 Hz, 1H), 2.06 (s, 3H), 1.83 (dd, J=9.9, 5.5 Hz, 1H), 1.75-1.61 (m, 1H), 1.53-1.45 (m, 2H), 1.43 (s, 9H), 1.37-1.10 (m, 13H), 0.89 (td, J=5.6, 4.9, 2.6 Hz, 3H); ¹³C NMR (101 MHz, CDCl₃) δ 173.30, 170.57, 155.29, 141.87, 129.10, 128.25, 125.72, 79.81, 71.92, 53.35, 52.17, 43.80, 40.10, 37.45, 32.80, 31.17, 30.52, 28.31, 26.36, 23.30, 22.99, 21.45, 18.59, 14.02; ESIMS m/z 514.3 ([M+Na]⁺).

Example 3

Step 3

Preparation of (2S,6R,7R)-6-benzyl-2-((tert-butoxycarbonyl)amino)-7-((S)-1-hydroxyethyl)undecanoic acid To a solution of (2S,6R,7R)-methyl 7-((S)-1-acetoxyethyl)-6-benzyl-2-((tert-butoxycarbonyl)amino)undecanoate (314 mg, 0.639 mmol) in MeOH (4 mL) and water (2 mL) at room temperature was added LiOH·H₂O (161 mg, 3.83 mmol). The reaction was stirred at room temperature overnight and the solution was diluted with EtOAc, washed with 1 N HCl, the phases separated, and the aqueous phase extracted with additional EtOAc (3×). The combined organic phases were washed with saturated aqueous NaHCO₃, dried over Na₂SO₄, filtered, and concentrated to furnish the title compound (277 mg, 100%) as a white foam: ESIMS m/z 458.3 ([M+Na]⁺).

Example 4

Preparation of tert-butyl((3S,7R,8R,9S)-7-benzyl-8-butyl-9-methyl-2-oxooxonan-3-yl)carbamate (Compound 127)

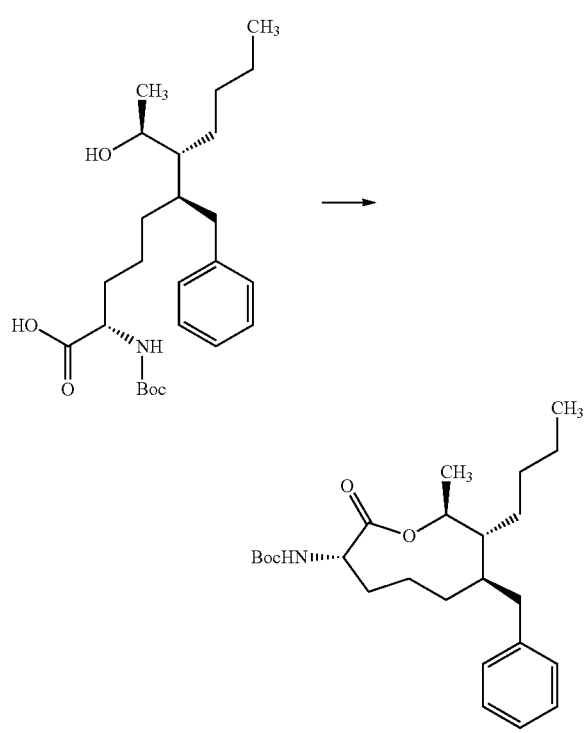

A solution of (2S,6R,7R)-6-benzyl-2-((tert-butoxycarbonyl)amino)-7-((S)-1-hydroxyethyl)undecanoic acid (298 mg, 0.684 mmol) in DCM (20 mL) was added over a 3 h period via a syringe pump to a solution of MNBA (377 mg, 1.095 mmol) and DMAP (501 mg, 4.10 mmol) in DCM (117 mL) at room temperature. The reaction mixture was stirred at room temperature overnight, concentrated, and the residue was purified by flash chromatography (SiO$_2$, 0→10% EtOAc in hexanes) to provide the title compound (202 mg, 70.7%) as a colorless oil, which slowly solidified to a white solid upon drying under vacuum: See Table 2 for characterization data.

Example 5

Steps 1 and 2

Preparation of N-((3S,7R,8R,9S)-7-benzyl-8-butyl-9-methyl-2-oxooxonan-3-yl)-3-hydroxy-4-methoxypicolinamide (Compounds 99 and 71

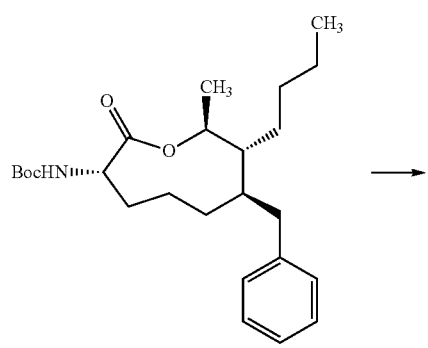

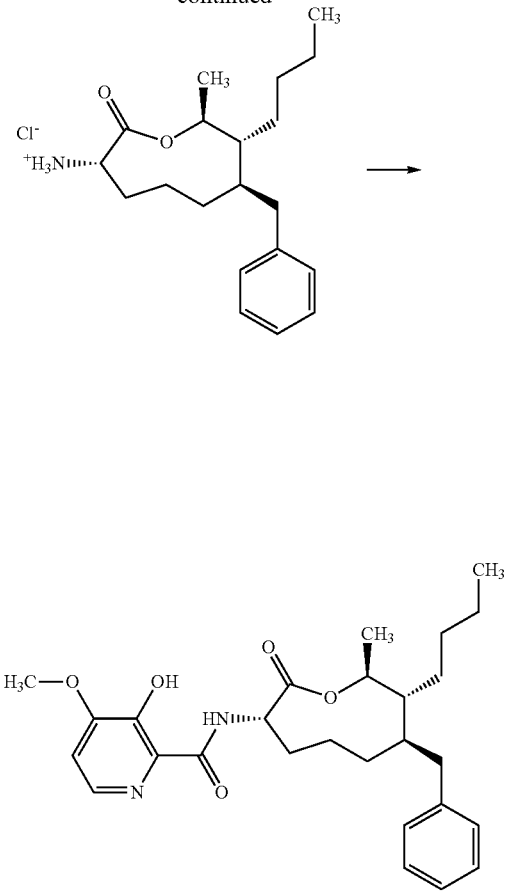

Step 1

To a solution of tert-butyl((3S,7R,8R,9S)-7-benzyl-8-butyl-9-methyl-2-oxooxonan-3-yl)carbamate (194 mg, 0.465 mmol) in DCM (2.5 mL) at room temperature was added HCl (4 M in dioxane, 1.2 mL, 4.8 mmol) and the reaction mixture was stirred at room temperature for 3 h. The solvent was evaporated in vacuo to provide (3S,7R,8R,9S)-7-benzyl-8-butyl-9-methyl-2-oxooxonan-3-aminium chloride (99, 142 mg, 86%) as a white solid: See Table 2 for characterization data.

Step 2

To a solution of the amine hydrochloride from step 1 (142 mg, 0.401 mmol) in DCM (4 mL) were added 3-hydroxy-4-methoxypicolinic acid (74.6 mg, 0.441 mmol) and PyBOP (230 mg, 0.441 mmol). To the resulting suspension was added N-ethyl-N-isopropylpropan-2-amine (231 μL, 1.32 mmol) and after 1 h, the reaction was concentrated and the residue was purified by flash chromatography (SiO$_2$, 0→100% EtOAc in hexanes) to provide the title compound (71, 158 mg, 84%) as a colorless, thick oil: See Table 2 for characterization data.

Example 6

Preparation of ((2-(((3S,7R,8R,9S)-7-benzyl-8-butyl-9-methyl-2-oxooxonan-3-yl)carbamoyl)-4-methoxypyridin-3-yl)oxy)methyl acetate (Compound 2)

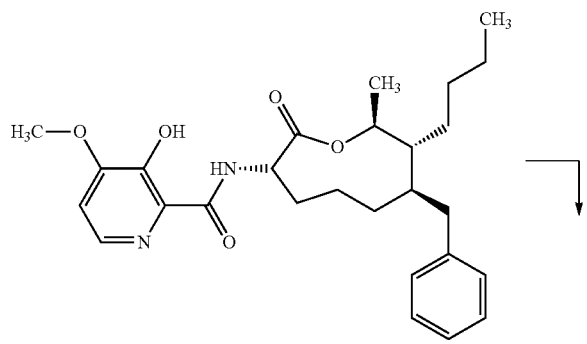

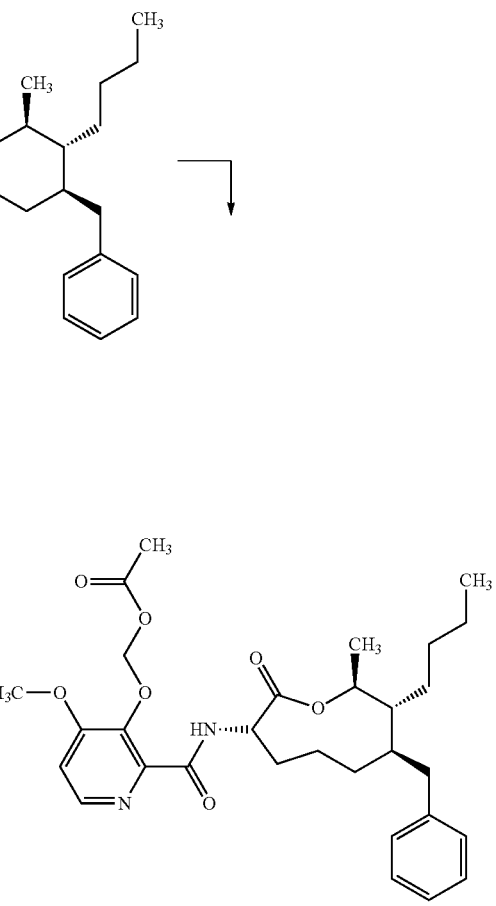

To a solution of N-((3S,7R,8R,9S)-7-benzyl-8-butyl-9-methyl-2-oxooxonan-3-yl)-3-hydroxy-4-methoxypicolinamide (78 mg, 0.166 mmol) in acetone (3 mL) were added bromomethyl acetate (24.48 μL, 0.250 mmol) and $K_2CO_3$ (46.0 mg, 0.333 mmol), and the solution was heated to 50° C. and stirred for 2 h. The solution was cooled to room temperature and concentrated, and the residue was purified by flash chromatography ($SiO_2$, 0→100% EtOAc in hexanes) to provide the title compound (71 mg, 79%) as a colorless oil: See Table 2 for characterization data.

Example 7

Preparation of 2-(((3S,7R,8R,9S)-7-benzyl-8-butyl-9-methyl-2-oxooxonan-3-yl)carbamoyl)-4-methoxypyridin-3-yl acetate (Compound 1)

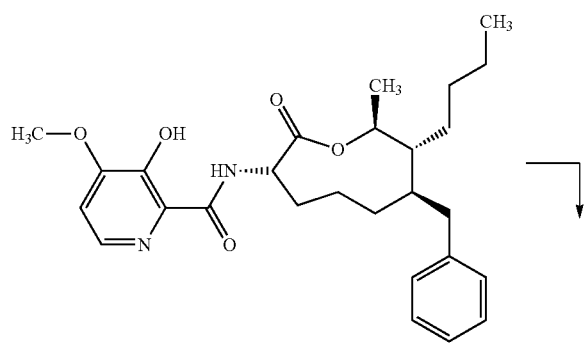

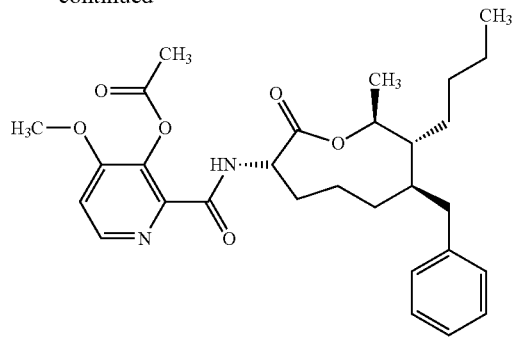

To a solution of N-((3S,7R,8R,9S)-7-benzyl-8-butyl-9-methyl-2-oxooxonan-3-yl)-3-hydroxy-4-methoxypicolinamide (70 mg, 0.149 mmol), DMAP (3.65 mg, 0.030 mmol) and Et₃N (41.6 µL, 0.299 mmol) in DCM (3 mL) was added acetyl chloride (15.9 µL, 0.224 mmol) at room temperature, and the reaction color gradually turned to orange. After stirring at room temperature for 2 h, the reaction mixture was purified by flash chromatography (SiO₂, 0→80% EtOAc in hexanes) to provide the title compound (71 mg, 93%) as a colorless oil: See Table 2 for characterization data.

Example 8

Preparation of ((2-(((3S,7R,8R,9S)-7,8-dibenzyl-9-methyl-2-oxooxonan-3-yl)carbamoyl)-4-methoxy-pyridin-3-yl)oxy)methyl isobutyrate (Compound 7)

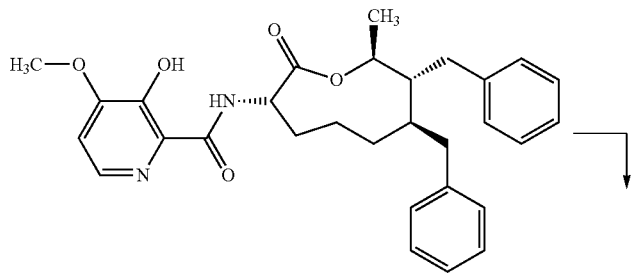

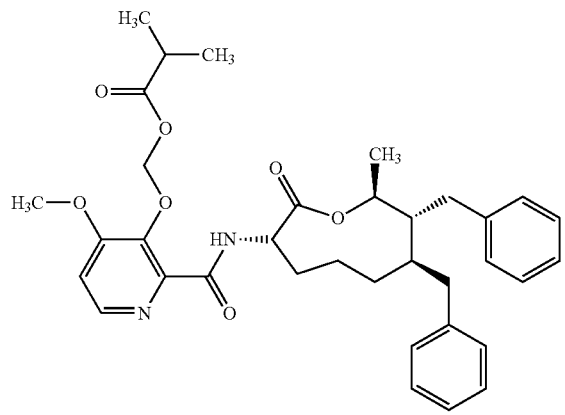

To a solution of N-((3S,7R,8R,9S)-7,8-dibenzyl-9-methyl-2-oxooxonan-3-yl)-3-hydroxy-4-methoxypicolinamide (77 mg, 0.153 mmol) in acetone (3 mL) were added chloromethyl isobutyrate (31.4 mg, 0.230 mmol), NaI (4.6 mg, 0.031 mmol) and $Na_2CO_3$ (32.5 mg, 0.306 mmol), and the solution was heated to 50° C. and stirred for overnight. The solution was cooled to room temperature and concentrated, and the residue was purified by flash chromatography ($SiO_2$, 0→100% EtOAc in hexanes) to provide the title compound (79 mg, 86%) as a colorless oil: See Table 2 for characterization data.

Example 9

Preparation of ((2-(((3S,7R,8R,9S)-7,8-dibenzyl-9-methyl-2-oxooxonan-3-yl)carbamoyl)-4-methoxy-pyridin-3-yl)oxy)methyl 2-ethoxyacetate (Compound 8)

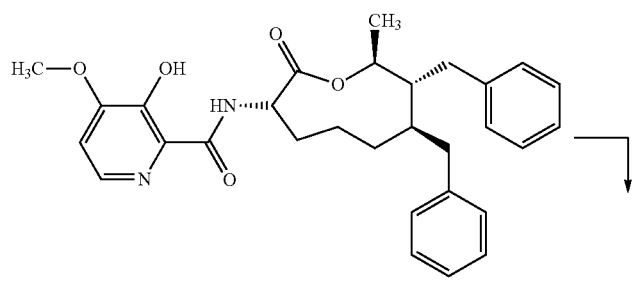

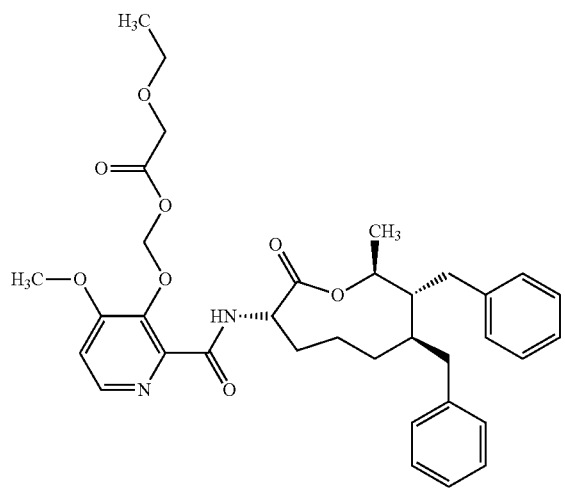

To a solution of N-((3S,7R,8R,9S)-7,8-dibenzyl-9-methyl-2-oxooxonan-3-yl)-3-hydroxy-4-methoxypicolinamide (77 mg, 0.153 mmol) in acetone (3 mL) were added chloromethyl 2-ethoxyacetate (37.4 mg, 0.245 mmol), NaI (4.6 mg, 0.031 mmol) and Na$_2$CO$_3$ (32.5 mg, 0.306 mmol), and the solution was heated to 50° C. and stirred for overnight. The solution was cooled to room temperature and concentrated, and the residue was purified by flash chromatography (SiO$_2$, 0→100% EtOAc in hexanes) to provide the title compound (74 mg, 78%) as a colorless oil: See Table 2 for characterization data.

Example 10

Preparation of 4-methoxy-2-(((3S,7S,8R,9S)-9-methyl-2-oxo-7-(3-phenylpropyl)-8-(4-(trifluoromethoxy)benzyl)oxonan-3-yl)carbamoyl)pyridin-3-yl isobutyrate (Compound 58)

To a solution of 3-hydroxy-4-methoxy-N-((3S,7S,8R,9S)-9-methyl-2-oxo-7-(3-phenylpropyl)-8-(4-(trifluoromethoxy)benzyl)oxonan-3-yl)picolinamide (70.2 mg, 0.114 mmol), DMAP (3.6 mg, 0.029 mmol), and Et$_3$N (32 µL, 0.230 mmol) in dichloromethane (1 mL) was added isobutyryl chloride (18 µL, 0.172 mmol) at room temperature. After stirring at room temperature for 3.5 h, the reaction mixture was purified by flash chromatography (SiO$_2$, 240% acetone in hexanes) to provide the title compound (78 mg, 100%) as a colorless oil: See Table 2 for characterization data.

Example A: Evaluation of Fungicidal Activity: Leaf Blotch of Wheat (*Mycosphaerella graminicola*; Anamorph: *Septoria tritici*; Bayer code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia triticina*; Synonym: *Puccinia recondita* f sp. *tritici*; Bayer code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Wheat Glume Blotch (*Leptosphaeria nodorum*; Bayer code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D: Evaluation of Fungicidal Activity: Apple Scab (*Venturia inaequalis*; Bayer code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% relative humidity for 48 hr, and then moved to a greenhouse set at 20° C. for disease to develop. Fungicide formulation, application and disease assessment on the sprayed leaves followed the procedures as described in the Example A.

Example E: Evaluation of Fungicidal Activity: Grape Powdery Mildew (*Uncinula necator*; Bayer code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example F: Evaluation of Fungicidal Activity: Powdery Mildew of Cucumber (*Erysiphe cichoracearum*; Bayer code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G: Evaluation of Fungicidal Activity: Leaf Spot of Sugar Beets (*Cercospora beticola*; Bayer code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H: Evaluation of Fungicidal Activity: Asian Soybean Rust (*Phakopsora pachyrhizi*; Bayer code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example I: Evaluation of Fungicidal Activity: Barley Powdery Mildew (*Blumeria graminis* fsp. *hordei*; Synonym: *Erysiphe graminis* fsp. *hordei*; Bayer code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J: Evaluation of Fungicidal Activity: Barley Scald (*Rhyncosporium secalis*; Bayer code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example K: Evaluation of Fungicidal Activity: Tomato Early Blight (*Alternaria solani*; Bayer code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.). to permit spores to germinate and infect the leaf. The plants were then transferred to a growth room at 22° C. for disease to develop. Fungicide formulation, application and disease assessment on the sprayed leaves followed the procedures as described in the Example A.

Example L: Evaluation of Fungicidal Activity: Cucumber Anthracnose (*Glomerella lagenarium*; Anamorph: *Colletotrichum lagenarium*; Bayer code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure and Appearance

| *Cmpd. No. | Structure | Prepared According to Example | Appearance |
|---|---|---|---|
| 1 | 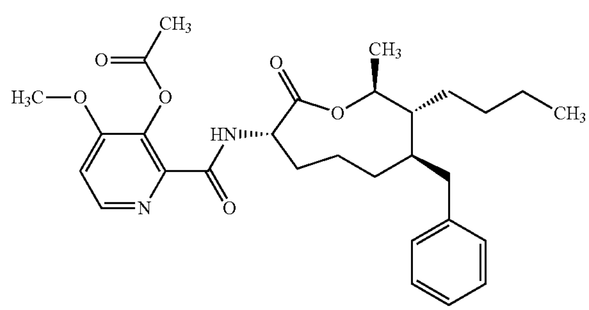 [SMILES: CCCC[C@@H]1[C@@H](Cc2ccccc2)CCC[C@H](NC(=O)c2nccc(OC)c2OC(C)=O)C(=O)O[C@H]1C] | Example 7 | Colorless Oil |
| 2 | 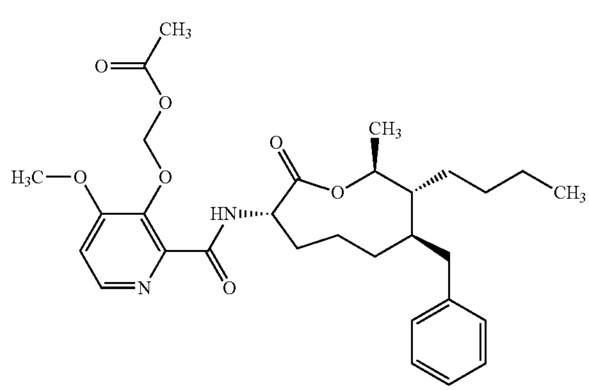 [SMILES: CCCC[C@@H]1[C@@H](Cc2ccccc2)CCC[C@H](NC(=O)c2nccc(OC)c2OCOC(C)=O)C(=O)O[C@H]1C] | Example 6 | Colorless Oil |

TABLE 1-continued

Compound Structure and Appearance

| *Cmpd. No. | Structure | Prepared According to Example | Appearance |
|---|---|---|---|
| 3 | 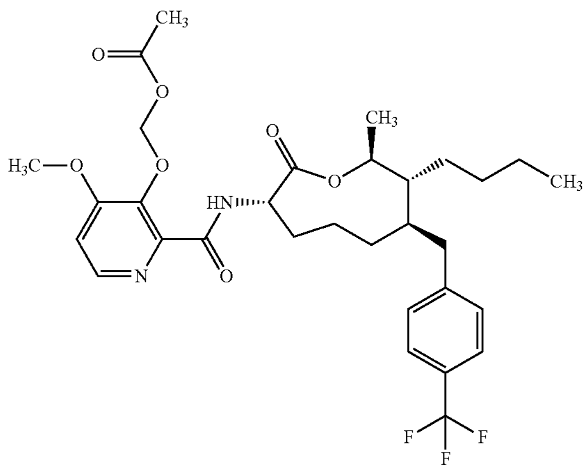 [SMILES: CCCC[C@@H]1[C@@H](Cc2ccc(C(F)(F)F)cc2)CCC[C@H](NC(=O)c2nccc(OC)c2OCOC(C)=O)C(=O)O[C@H]1C] | Example 6 | Colorless Gel |
| 4 | 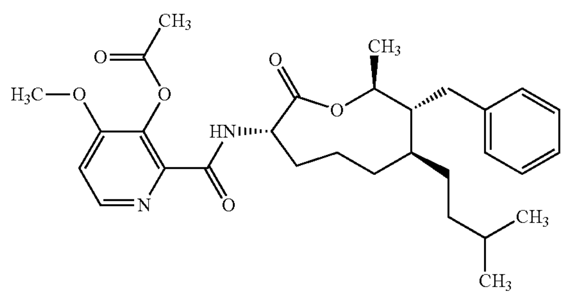 [SMILES: COc1ccnc(C(=O)N[C@H]2CCC[C@H](CCC(C)C)[C@@H](Cc3ccccc3)[C@H](C)OC2=O)c1OC(C)=O] | Example 7 | Colorless Oil |
| 5 | 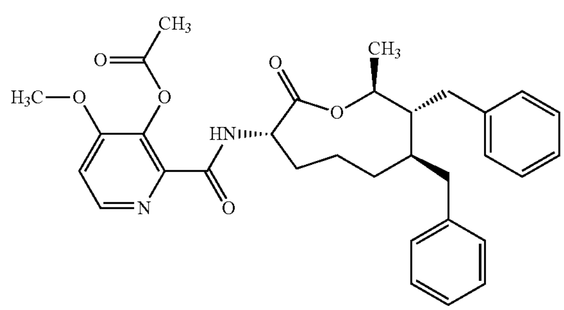 [SMILES: COc1ccnc(C(=O)N[C@H]2CCC[C@H](Cc3ccccc3)[C@@H](Cc3ccccc3)[C@H](C)OC2=O)c1OC(C)=O] | Example 7 | Colorless Oil |
| 6 | 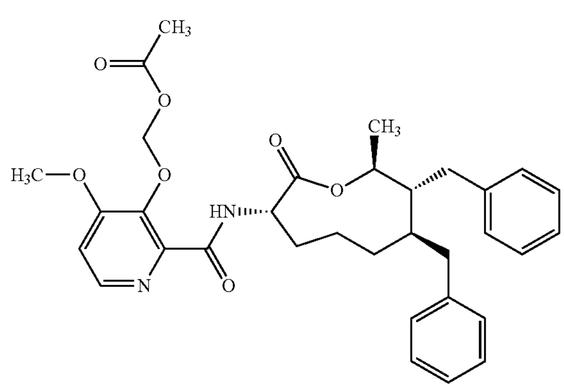 [SMILES: COc1ccnc(C(=O)N[C@H]2CCC[C@H](Cc3ccccc3)[C@@H](Cc3ccccc3)[C@H](C)OC2=O)c1OCOC(C)=O] | Example 6 | Colorless Foam |

US 9,700,047 B2
TABLE 1-continued
Compound Structure and Appearance
| *Cmpd. No. | Structure | Prepared According to Example | Appearance |
|---|---|---|---|
| 7 | 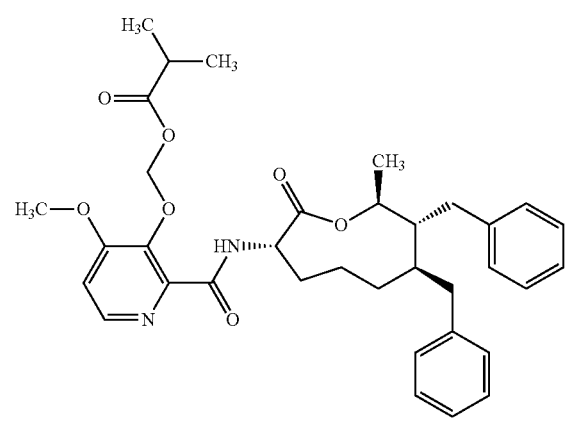 [SMILES: COc1ccnc(C(=O)N[C@H]2CCC[C@H](Cc3ccccc3)[C@@H](Cc3ccccc3)[C@H](C)OC2=O)c1OCOC(=O)C(C)C] | Example 8 | Colorless Foam |
| 8 | 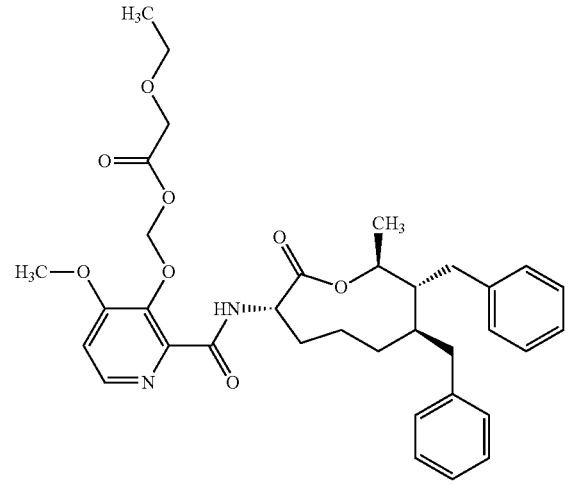 [SMILES: CCOCC(=O)OCOc1c(OC)ccnc1C(=O)N[C@H]1CCC[C@H](Cc2ccccc2)[C@@H](Cc2ccccc2)[C@H](C)OC1=O] | Example 9 | Colorless Oil |
| 9 | 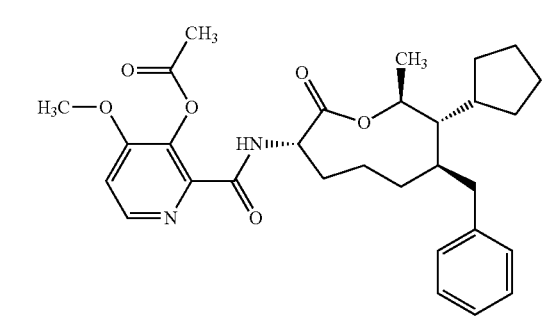 [SMILES: COc1ccnc(C(=O)N[C@H]2CCC[C@H](Cc3ccccc3)[C@@H](C3CCCC3)[C@H](C)OC2=O)c1OC(C)=O] | Example 7 | Colorless Oil |

TABLE 1-continued

Compound Structure and Appearance

| *Cmpd. No. | Structure | Prepared According to Example | Appearance |
|---|---|---|---|
| 10 | 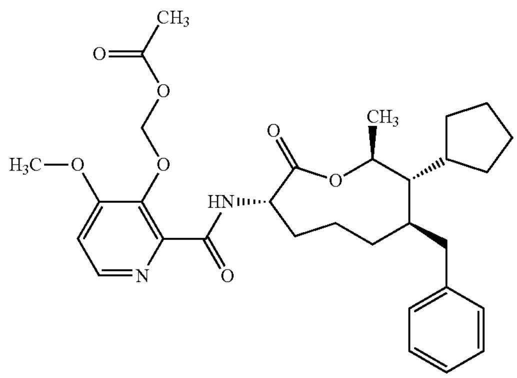 [SMILES: COc1ccnc(C(=O)N[C@H]2CCC[C@H](Cc3ccccc3)[C@@H](C3CCCC3)[C@H](C)OC2=O)c1OCOC(C)=O] | Example 6 | Colorless Oil |
| 11 | 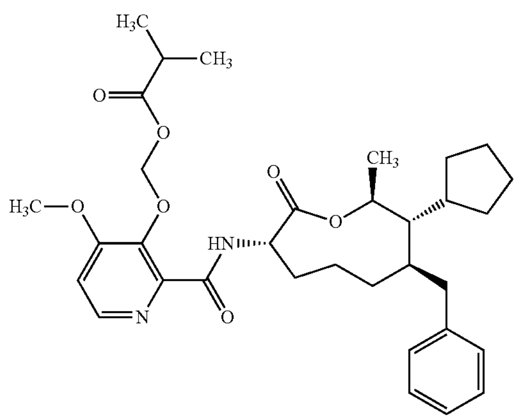 [SMILES: COc1ccnc(C(=O)N[C@H]2CCC[C@H](Cc3ccccc3)[C@@H](C3CCCC3)[C@H](C)OC2=O)c1OCOC(=O)C(C)C] | Example 8 | Colorless Oil |
| 12 | 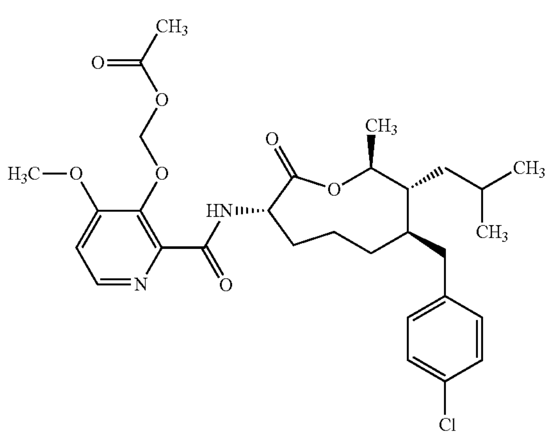 [SMILES: COc1ccnc(C(=O)N[C@H]2CCC[C@H](Cc3ccc(Cl)cc3)[C@@H](CC(C)C)[C@H](C)OC2=O)c1OCOC(C)=O] | Example 6 | Colorless Oil |

TABLE 1-continued
Compound Structure and Appearance
| *Cmpd. No. | Structure | Prepared According to Example | Appearance |
|---|---|---|---|
| 13 | 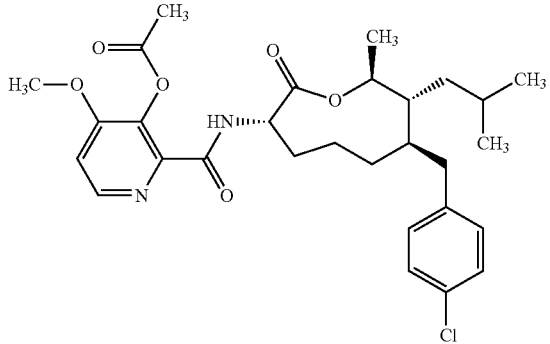 [SMILES: COc1ccnc(C(=O)N[C@H]2CCC[C@H](Cc3ccc(Cl)cc3)[C@@H](CC(C)C)[C@H](C)OC2=O)c1OC(C)=O] | Example 7 | Colorless Oil |
| 14 | 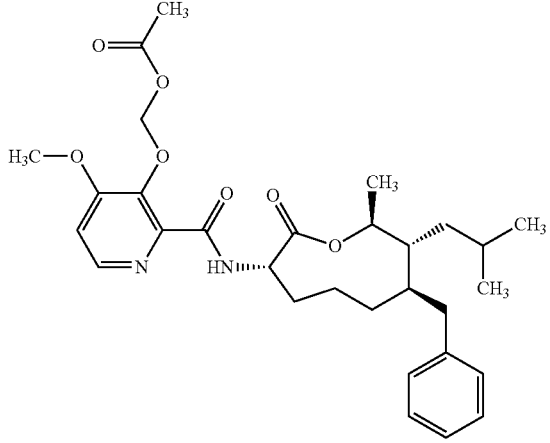 [SMILES: COc1ccnc(C(=O)N[C@H]2CCC[C@H](Cc3ccccc3)[C@@H](CC(C)C)[C@H](C)OC2=O)c1OCOC(C)=O] | Example 6 | White Solid |
| 15 | 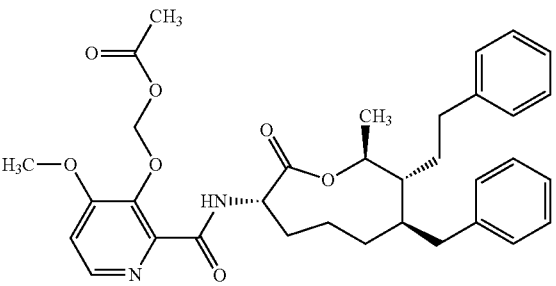 [SMILES: COc1ccnc(C(=O)N[C@H]2CCC[C@H](Cc3ccccc3)[C@@H](CCc3ccccc3)[C@H](C)OC2=O)c1OCOC(C)=O] | Example 6 | Colorless Solid |

TABLE 1-continued

Compound Structure and Appearance

| *Cmpd. No. | Structure | Prepared According to Example | Appearance |
|---|---|---|---|
| 16 | 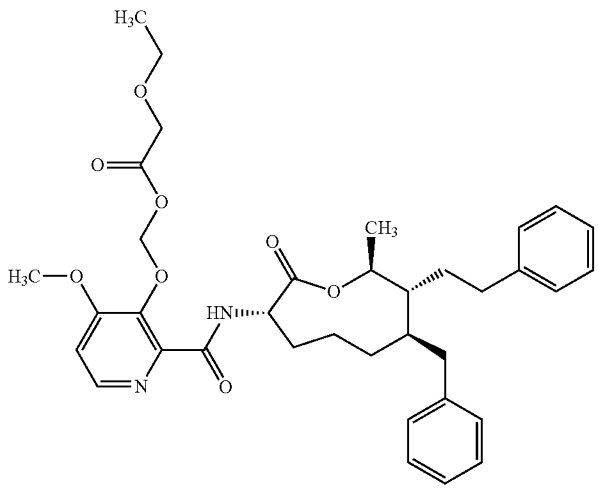 [SMILES: CCOCC(=O)OCOc1c(OC)ccnc1C(=O)N[C@H]1CCC[C@H](Cc2ccccc2)[C@@H](CCc2ccccc2)[C@H](C)OC1=O] | Example 9 | Colorless Thick Oil |
| 17 | 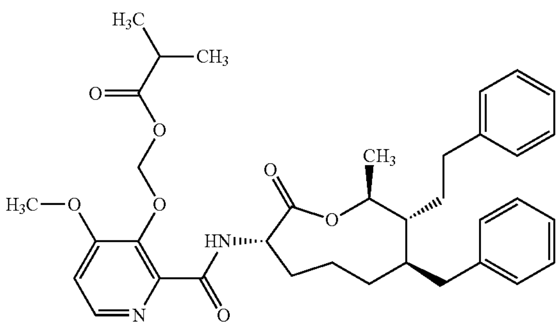 [SMILES: COc1ccnc(C(=O)N[C@H]2CCC[C@H](Cc3ccccc3)[C@@H](CCc3ccccc3)[C@H](C)OC2=O)c1OCOC(=O)C(C)C] | Example 8 | Colorless Solid |
| 18 | 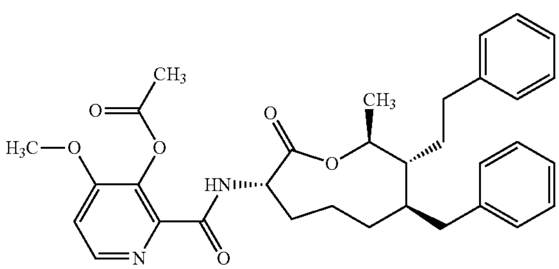 [SMILES: COc1ccnc(C(=O)N[C@H]2CCC[C@H](Cc3ccccc3)[C@@H](CCc3ccccc3)[C@H](C)OC2=O)c1OC(C)=O] | Example 7 | Pale Yellow Oil |
| 19 | 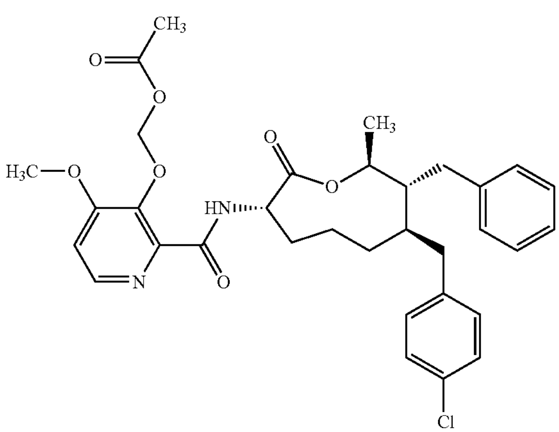 [SMILES: COc1ccnc(C(=O)N[C@H]2CCC[C@H](Cc3ccc(Cl)cc3)[C@@H](Cc3ccccc3)[C@H](C)OC2=O)c1OCOC(C)=O] | Example 6 | Colorless Solid |

TABLE 1-continued
Compound Structure and Appearance
| *Cmpd. No. | Structure | Prepared According to Example | Appearance |
|---|---|---|---|
| 20 | 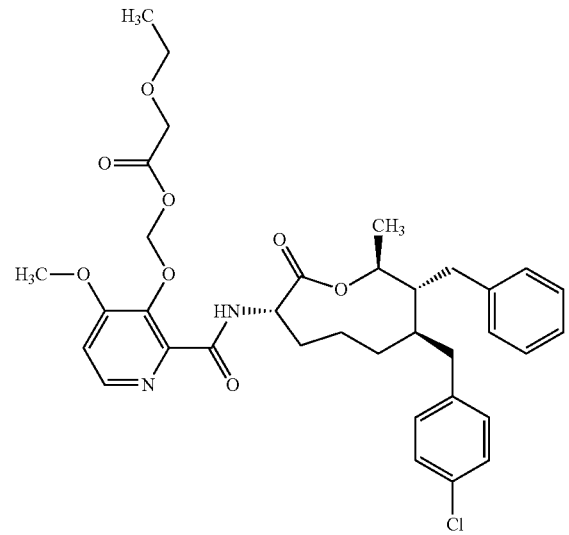 [SMILES: CCOCC(=O)OCOc1c(OC)ccnc1C(=O)N[C@H]1CCC[C@H](Cc2ccc(Cl)cc2)[C@@H](Cc2ccccc2)[C@H](C)OC1=O] | Example 9 | Colorless Oil |
| 21 | 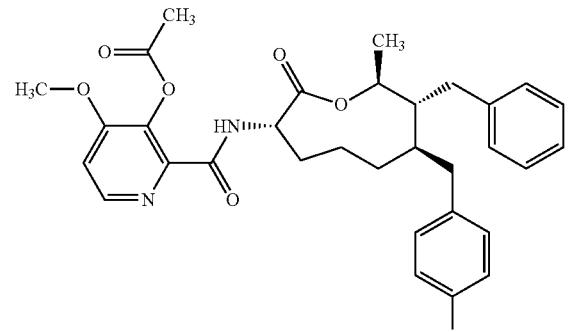 | Example 7 | Yellow Oil |
| 22 | 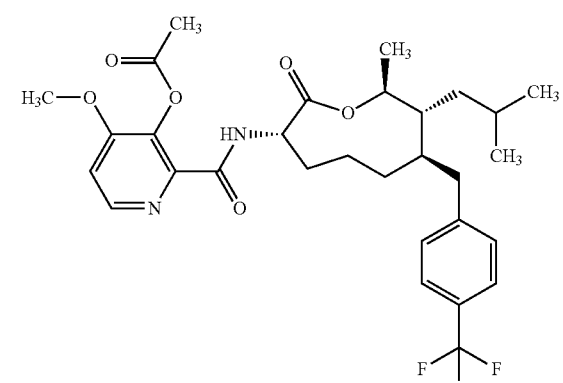 | Example 7 | Colorless Oil |

TABLE 1-continued

Compound Structure and Appearance

| *Cmpd. No. | Structure | Prepared According to Example | Appearance |
| --- | --- | --- | --- |
| 23 | 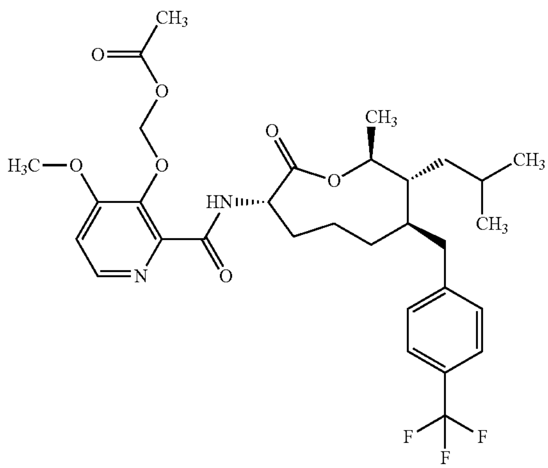 [SMILES: COc1ccnc(C(=O)N[C@H]2CCC[C@H](Cc3ccc(C(F)(F)F)cc3)[C@@H](CC(C)C)[C@H](C)OC2=O)c1OCOC(C)=O] | Example 6 | Colorless Oil |
| 24 | 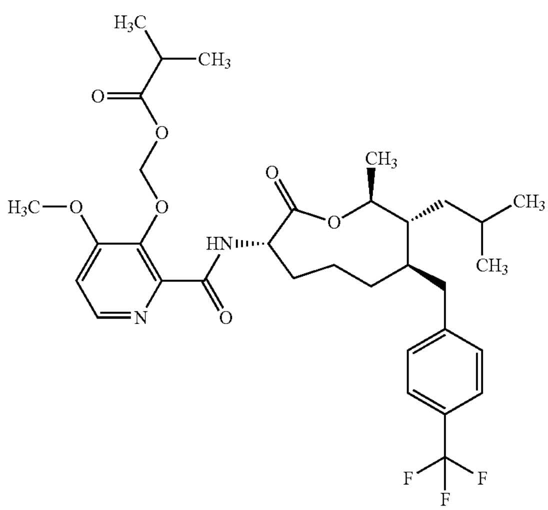 [SMILES: COc1ccnc(C(=O)N[C@H]2CCC[C@H](Cc3ccc(C(F)(F)F)cc3)[C@@H](CC(C)C)[C@H](C)OC2=O)c1OCOC(=O)C(C)C] | Example 8 | Colorless Oil |
| 25 | 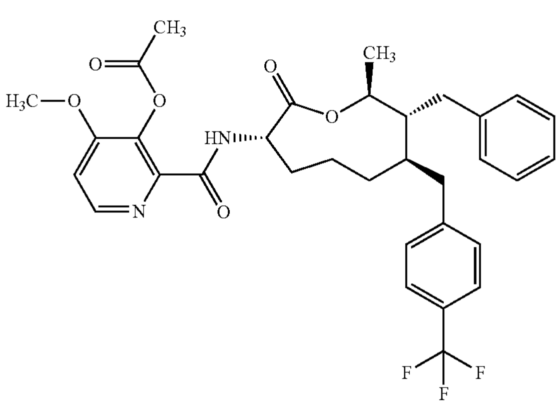 [SMILES: COc1ccnc(C(=O)N[C@H]2CCC[C@H](Cc3ccc(C(F)(F)F)cc3)[C@@H](Cc3ccccc3)[C@H](C)OC2=O)c1OC(C)=O] | Example 7 | Colorless Oil |

TABLE 1-continued

Compound Structure and Appearance

| *Cmpd. No. | Structure | Prepared According to Example | Appearance |
|---|---|---|---|
| 26 | 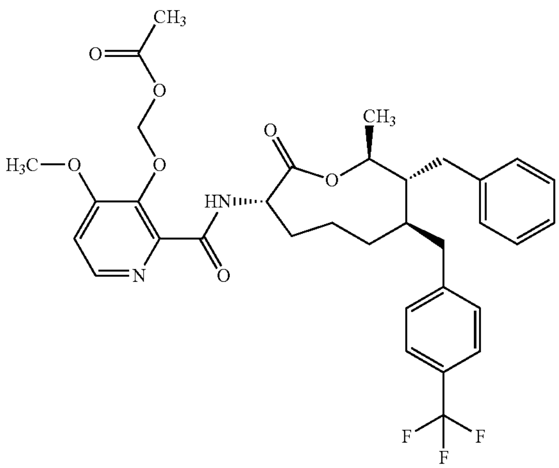 [SMILES: COc1ccnc(C(=O)N[C@H]2CCC[C@H](Cc3ccc(C(F)(F)F)cc3)[C@@H](Cc3ccccc3)[C@H](C)OC2=O)c1OCOC(C)=O] | Example 6 | Colorless Oil |
| 27 | 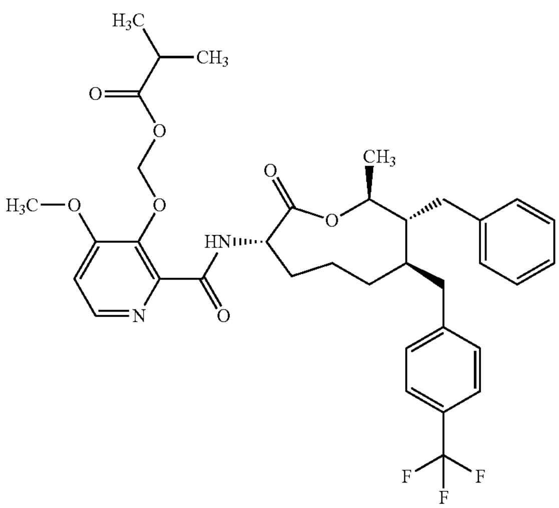 [SMILES: COc1ccnc(C(=O)N[C@H]2CCC[C@H](Cc3ccc(C(F)(F)F)cc3)[C@@H](Cc3ccccc3)[C@H](C)OC2=O)c1OCOC(=O)C(C)C] | Example 8 | Colorless Oil |
| 28 | 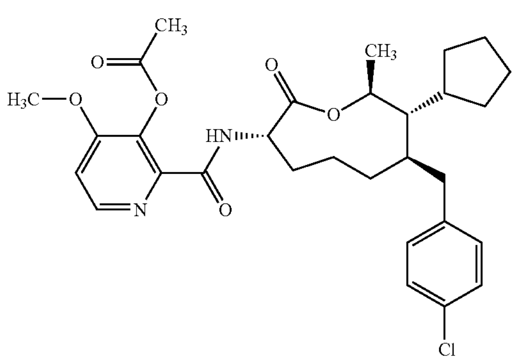 [SMILES: COc1ccnc(C(=O)N[C@H]2CCC[C@H](Cc3ccc(Cl)cc3)[C@@H](C3CCCC3)[C@H](C)OC2=O)c1OC(C)=O] | Example 7 | Colorless Oil |

TABLE 1-continued

Compound Structure and Appearance

| *Cmpd. No. | Structure | Prepared According to Example | Appearance |
|---|---|---|---|
| 29 | 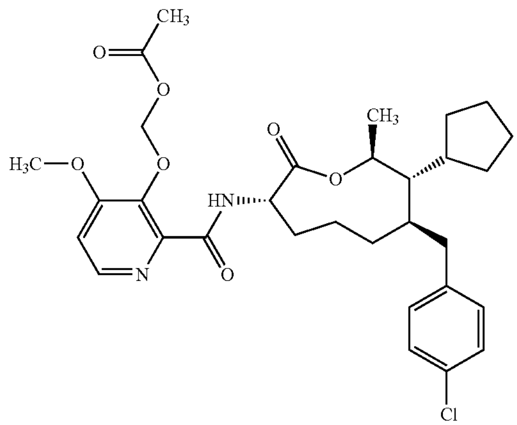 [SMILES: COc1ccnc(C(=O)N[C@H]2CCC[C@H](Cc3ccc(Cl)cc3)[C@@H](C3CCCC3)[C@H](C)OC2=O)c1OCOC(C)=O] | Example 6 | Colorless Oil |
| 30 | 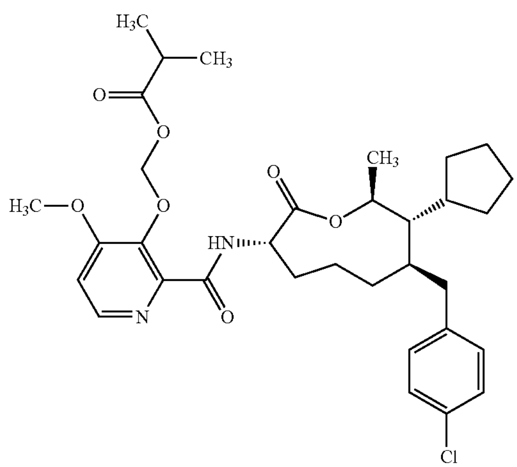 [SMILES: COc1ccnc(C(=O)N[C@H]2CCC[C@H](Cc3ccc(Cl)cc3)[C@@H](C3CCCC3)[C@H](C)OC2=O)c1OCOC(=O)C(C)C] | Example 8 | Colorless Oil |
| 31 | 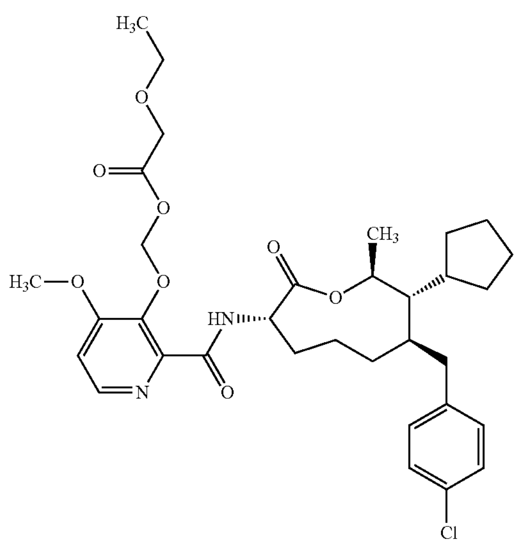 [SMILES: CCOCC(=O)OCOc1c(OC)ccnc1C(=O)N[C@H]1CCC[C@H](Cc2ccc(Cl)cc2)[C@@H](C2CCCC2)[C@H](C)OC1=O] | Example 9 | Colorless Oil |

TABLE 1-continued

Compound Structure and Appearance

| *Cmpd. No. | Structure | Prepared According to Example | Appearance |
|---|---|---|---|
| 32 | 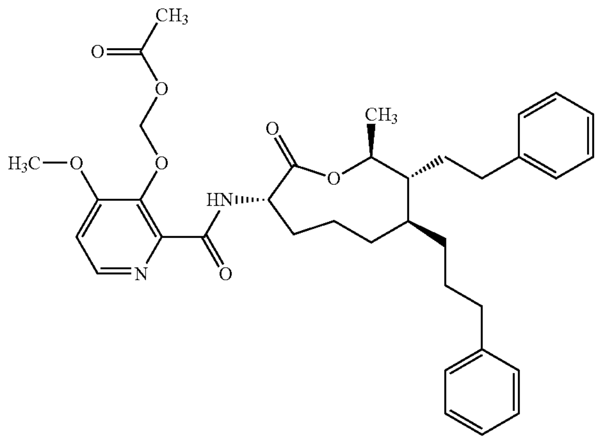 [SMILES: COc1ccnc(C(=O)N[C@H]2CCC[C@H](CCCc3ccccc3)[C@@H](CCc3ccccc3)[C@H](C)OC2=O)c1OCOC(C)=O] | Example 6 | White Foam |
| 33 | 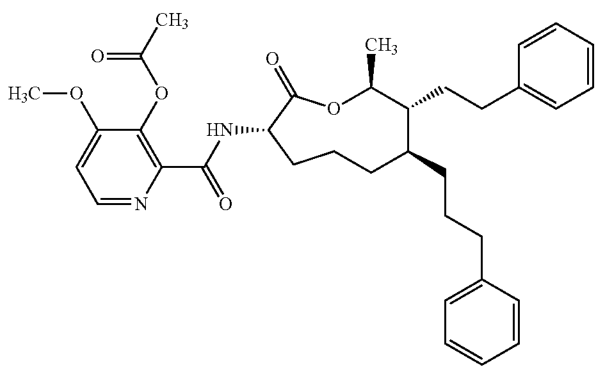 [SMILES: COc1ccnc(C(=O)N[C@H]2CCC[C@H](CCCc3ccccc3)[C@@H](CCc3ccccc3)[C@H](C)OC2=O)c1OC(C)=O] | Example 7 | Light Yellow Oil |
| 34 | 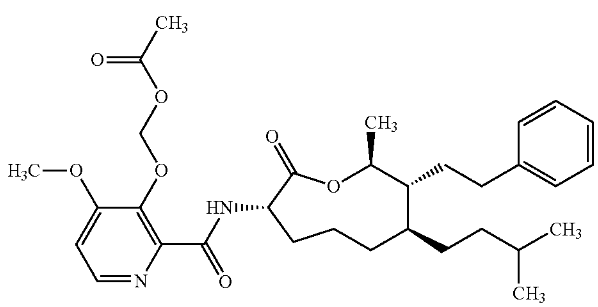 [SMILES: COc1ccnc(C(=O)N[C@H]2CCC[C@H](CCC(C)C)[C@@H](CCc3ccccc3)[C@H](C)OC2=O)c1OCOC(C)=O] | Example 6 | Colorless Oil |
| 35 | 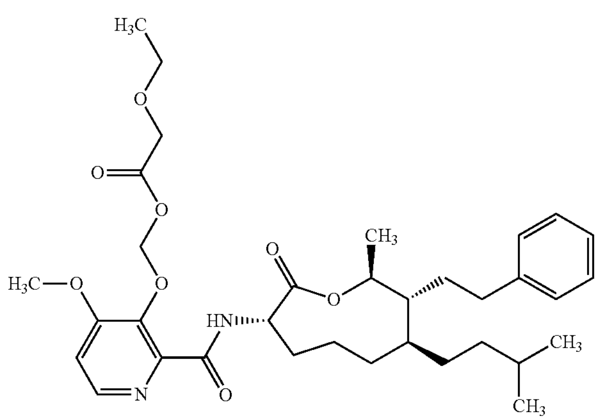 [SMILES: CCOCC(=O)OCOc1c(OC)ccnc1C(=O)N[C@H]1CCC[C@H](CCC(C)C)[C@@H](CCc2ccccc2)[C@H](C)OC1=O] | Example 9 | Colorless Oil |

TABLE 1-continued

Compound Structure and Appearance

| *Cmpd. No. | Structure | Prepared According to Example | Appearance |
|---|---|---|---|
| 36 | 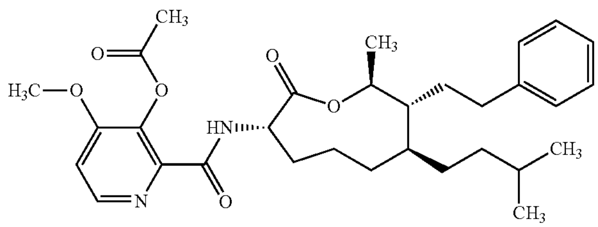 [SMILES: COc1ccnc(C(=O)N[C@H]2CCC[C@H](CCC(C)C)[C@@H](CCc3ccccc3)[C@H](C)OC2=O)c1OC(C)=O] | Example 7 | Yellow Oil |
| 37 | 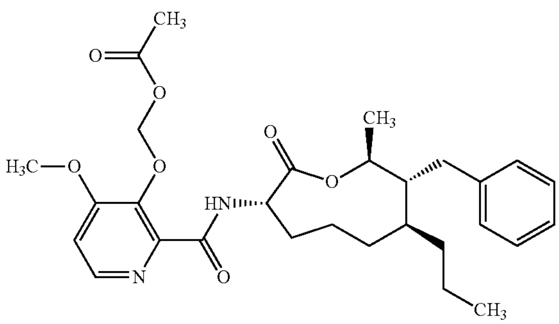 [SMILES: CCC[C@H]1CCC[C@H](NC(=O)c2nccc(OC)c2OCOC(C)=O)C(=O)O[C@@H](C)[C@@H]1Cc1ccccc1] | Example 6 | Colorless Oil |
| 38 | 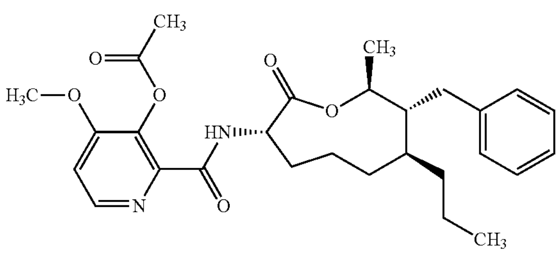 [SMILES: CCC[C@H]1CCC[C@H](NC(=O)c2nccc(OC)c2OC(C)=O)C(=O)O[C@@H](C)[C@@H]1Cc1ccccc1] | Example 7 | Yellow Oil |
| 39 | 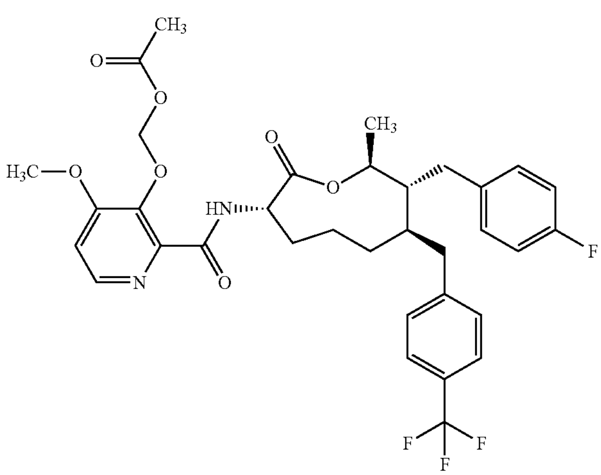 [SMILES: COc1ccnc(C(=O)N[C@H]2CCC[C@H](Cc3ccc(C(F)(F)F)cc3)[C@@H](Cc3ccc(F)cc3)[C@H](C)OC2=O)c1OCOC(C)=O] | Example 6 | White Foam |

TABLE 1-continued

Compound Structure and Appearance

| *Cmpd. No. | Structure | Prepared According to Example | Appearance |
| --- | --- | --- | --- |
| 40 | 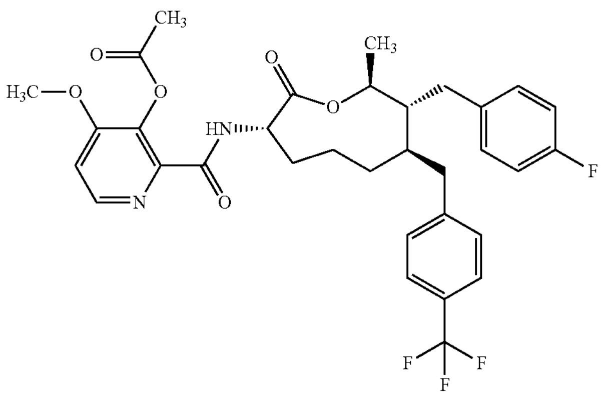 [SMILES: COc1ccnc(C(=O)N[C@H]2CCC[C@H](Cc3ccc(C(F)(F)F)cc3)[C@@H](Cc3ccc(F)cc3)[C@H](C)OC2=O)c1OC(C)=O] | Example 7 | Light Orange Foam |
| 41 | 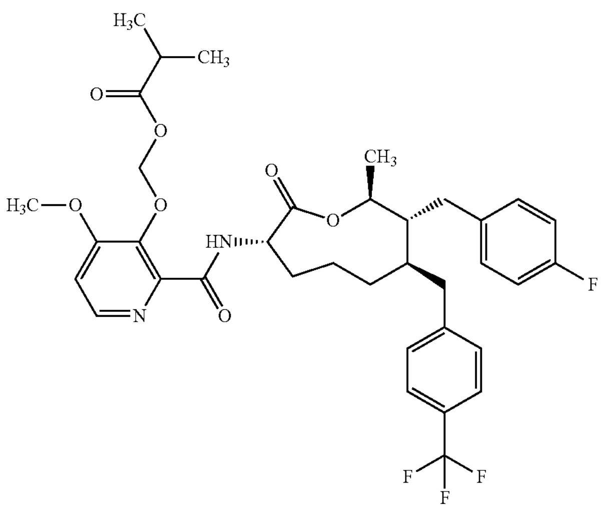 [SMILES: COc1ccnc(C(=O)N[C@H]2CCC[C@H](Cc3ccc(C(F)(F)F)cc3)[C@@H](Cc3ccc(F)cc3)[C@H](C)OC2=O)c1OCOC(=O)C(C)C] | Example 8 | White Foam |
| 42 | 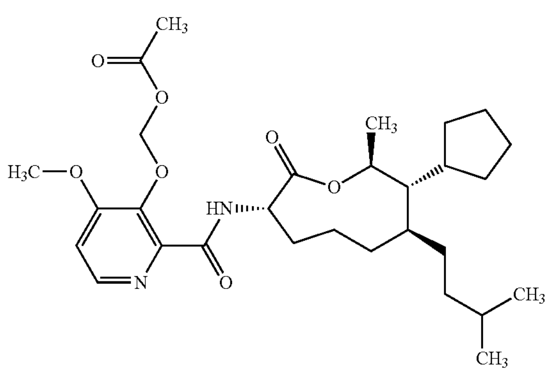 [SMILES: COc1ccnc(C(=O)N[C@H]2CCC[C@H](CCC(C)C)[C@@H](C3CCCC3)[C@H](C)OC2=O)c1OCOC(C)=O] | Example 6 | Colorless Oil |

TABLE 1-continued

Compound Structure and Appearance

| *Cmpd. No. | Structure | Prepared According to Example | Appearance |
|---|---|---|---|
| 43 | 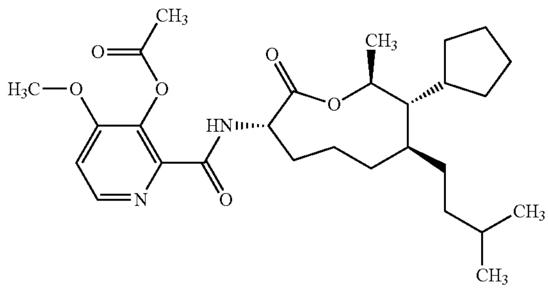 [SMILES: COc1ccnc(C(=O)N[C@H]2CCC[C@H](CCC(C)C)[C@@H](C3CCCC3)[C@H](C)OC2=O)c1OC(C)=O] | Example 7 | Light Orange Foam |
| 44 | 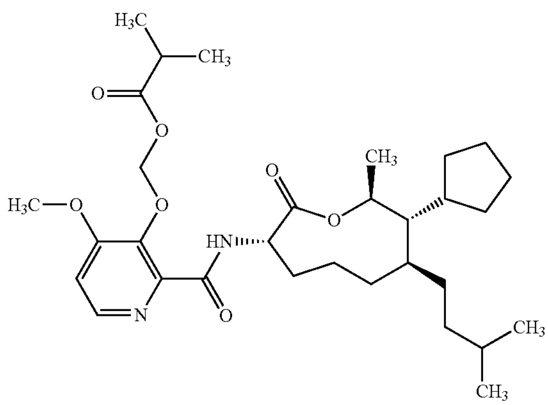 [SMILES: COc1ccnc(C(=O)N[C@H]2CCC[C@H](CCC(C)C)[C@@H](C3CCCC3)[C@H](C)OC2=O)c1OCOC(=O)C(C)C] | Example 8 | Colorless Oil |
| 45 | 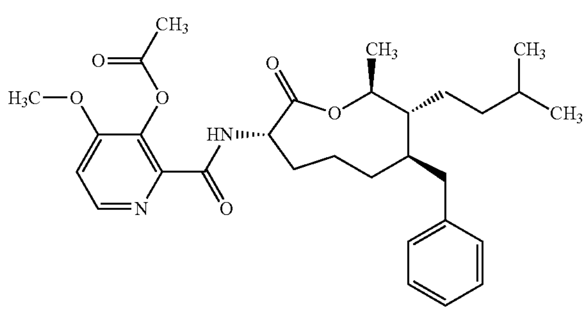 [SMILES: COc1ccnc(C(=O)N[C@H]2CCC[C@H](Cc3ccccc3)[C@@H](CCC(C)C)[C@H](C)OC2=O)c1OC(C)=O] | Example 7 | Colorless Oil |
| 46 | 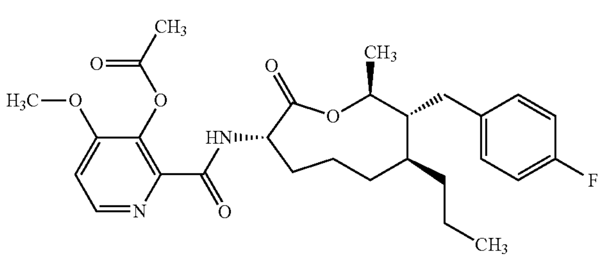 [SMILES: CCC[C@H]1CCC[C@H](NC(=O)c2nccc(OC)c2OC(C)=O)C(=O)O[C@@H](C)[C@@H]1Cc1ccc(F)cc1] | Example 7 | Colorless Oil |

TABLE 1-continued

Compound Structure and Appearance

| *Cmpd. No. | Structure | Prepared According to Example | Appearance |
|---|---|---|---|
| 47 | 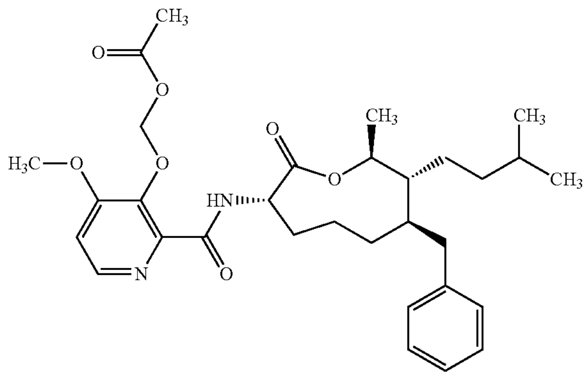 [SMILES: COc1ccnc(C(=O)N[C@H]2CCC[C@H](Cc3ccccc3)[C@@H](CCC(C)C)[C@H](C)OC2=O)c1OCOC(C)=O] | Example 6 | Colorless Oil |
| 48 | 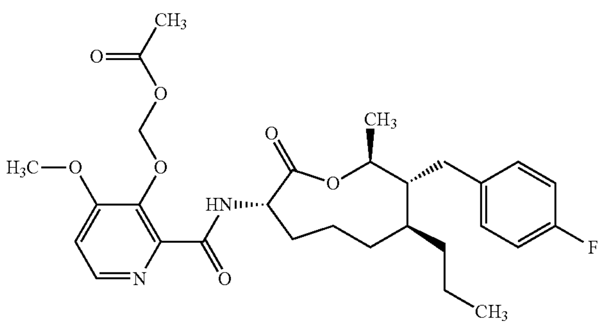 [SMILES: CCC[C@H]1CCC[C@H](NC(=O)c2nccc(OC)c2OCOC(C)=O)C(=O)O[C@@H](C)[C@@H]1Cc1ccc(F)cc1] | Example 6 | Colorless Oil |
| 49 | 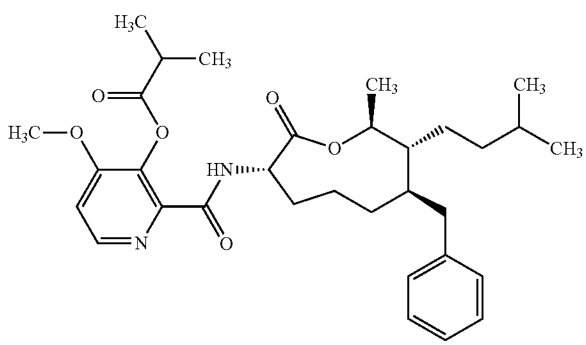 [SMILES: COc1ccnc(C(=O)N[C@H]2CCC[C@H](Cc3ccccc3)[C@@H](CCC(C)C)[C@H](C)OC2=O)c1OC(=O)C(C)C] | Example 10 | Colorless Oil |
| 50 | 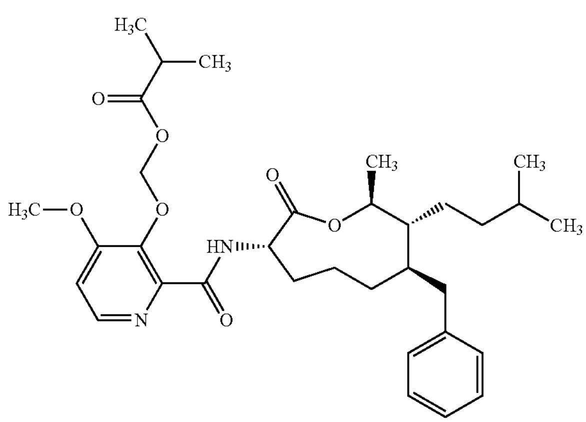 [SMILES: COc1ccnc(C(=O)N[C@H]2CCC[C@H](Cc3ccccc3)[C@@H](CCC(C)C)[C@H](C)OC2=O)c1OCOC(=O)C(C)C] | Example 8 | Colorless Oil |

TABLE 1-continued
Compound Structure and Appearance
| *Cmpd. No. | Structure | Prepared According to Example | Appearance |
|---|---|---|---|
| 51 | 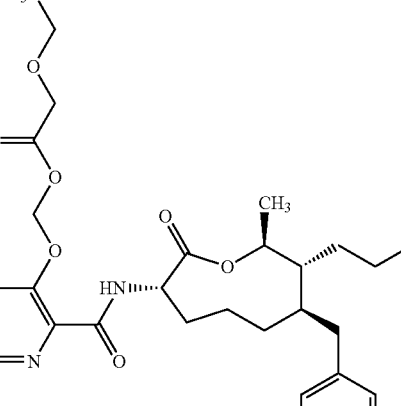 | Example 9 | Colorless Oil |
| 52 | 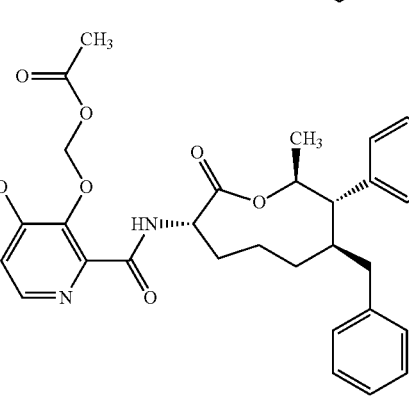 | Example 6 | White Foam |
| 53 | 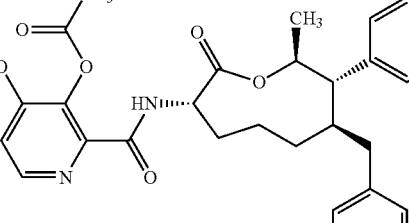 | Example 7 | Light Orange Foam |
| 54 | 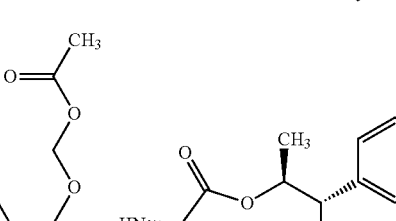 | Example 6 | Light Yellow Oil |

TABLE 1-continued

Compound Structure and Appearance

| *Cmpd. No. | Structure | Prepared According to Example | Appearance |
|---|---|---|---|
| 55 | 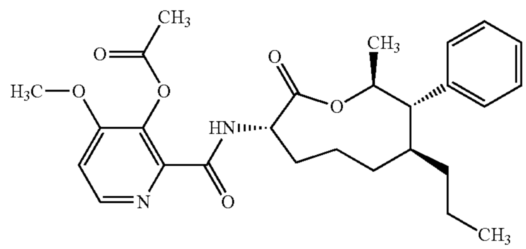 [SMILES: CCC[C@H]1CCC[C@H](NC(=O)c2nccc(OC)c2OC(C)=O)C(=O)O[C@@H](C)[C@@H]1c1ccccc1] | Example 7 | Orange Foam |
| 56 | 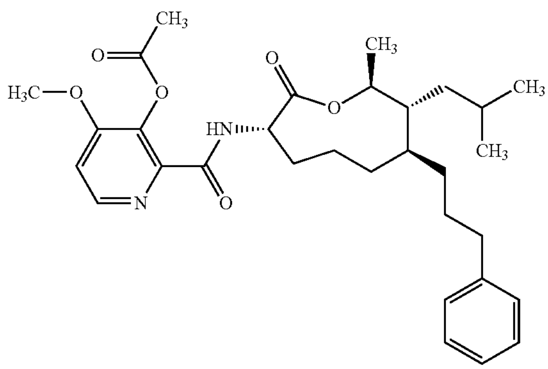 [SMILES: COc1ccnc(C(=O)N[C@H]2CCC[C@H](CCCc3ccccc3)[C@@H](CC(C)C)[C@H](C)OC2=O)c1OC(C)=O] | Example 7 | Colorless Oil |
| 57 | 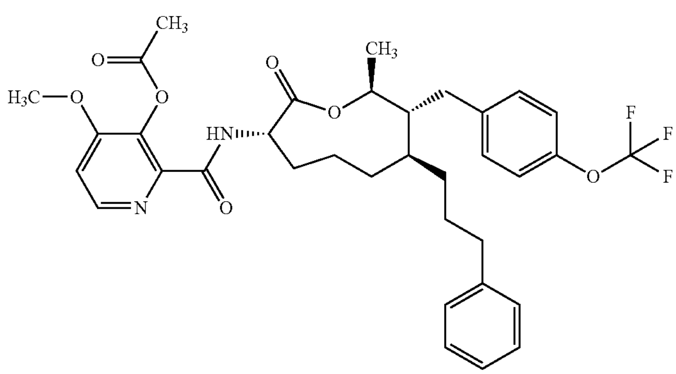 [SMILES: COc1ccnc(C(=O)N[C@H]2CCC[C@H](CCCc3ccccc3)[C@@H](Cc3ccc(OC(F)(F)F)cc3)[C@H](C)OC2=O)c1OC(C)=O] | Example 7 | Colorless Oil |
| 58 | 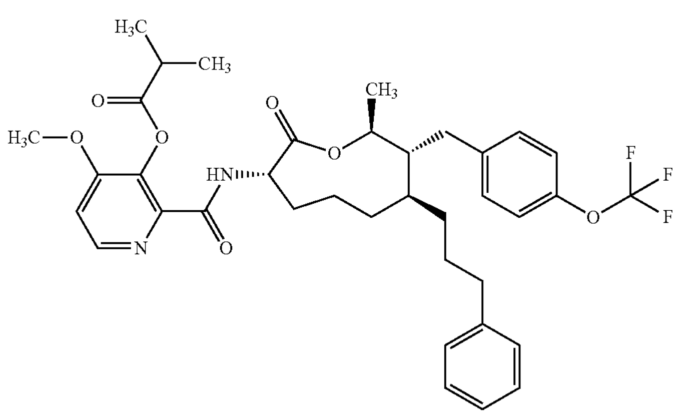 [SMILES: COc1ccnc(C(=O)N[C@H]2CCC[C@H](CCCc3ccccc3)[C@@H](Cc3ccc(OC(F)(F)F)cc3)[C@H](C)OC2=O)c1OC(=O)C(C)C] | Example 10 | Colorless Oil |

TABLE 1-continued

| *Cmpd. No. | Structure | Prepared According to Example | Appearance |
|---|---|---|---|
| 59 | 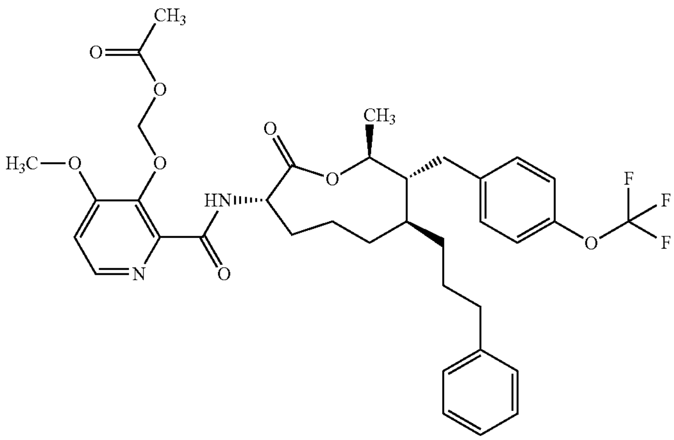 [SMILES: COc1ccnc(C(=O)N[C@H]2CCC[C@H](CCCc3ccccc3)[C@@H](Cc3ccc(OC(F)(F)F)cc3)[C@H](C)OC2=O)c1OCOC(C)=O] | Example 6 | Colorless Oil |
| 60 | 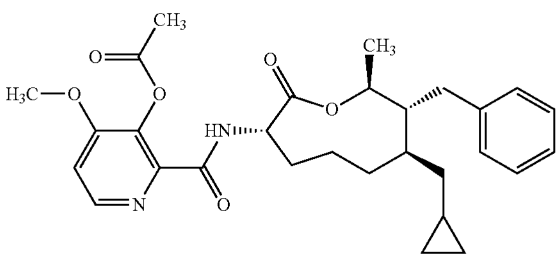 [SMILES: COc1ccnc(C(=O)N[C@H]2CCC[C@H](CC3CC3)[C@@H](Cc3ccccc3)[C@H](C)OC2=O)c1OC(C)=O] | Example 7 | Colorless Oil |
| 61 | 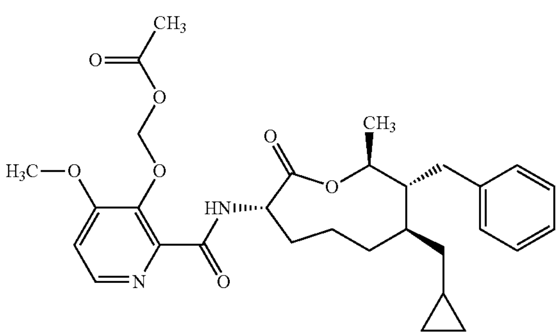 [SMILES: COc1ccnc(C(=O)N[C@H]2CCC[C@H](CC3CC3)[C@@H](Cc3ccccc3)[C@H](C)OC2=O)c1OCOC(C)=O] | Example 6 | Colorless Oil |
| 62 | 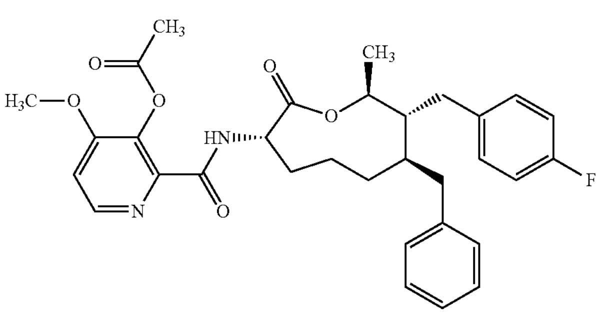 [SMILES: COc1ccnc(C(=O)N[C@H]2CCC[C@H](Cc3ccccc3)[C@@H](Cc3ccc(F)cc3)[C@H](C)OC2=O)c1OC(C)=O] | Example 7 | Colorless Oil |

TABLE 1-continued
Compound Structure and Appearance
| *Cmpd. No. | Structure | Prepared According to Example | Appearance |
| --- | --- | --- | --- |
| 63 | 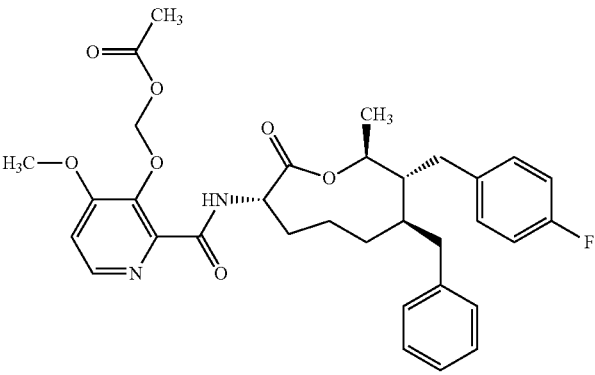 [SMILES: COc1ccnc(C(=O)N[C@H]2CCC[C@H](Cc3ccccc3)[C@@H](Cc3ccc(F)cc3)[C@H](C)OC2=O)c1OCOC(C)=O] | Example 6 | Colorless Oil |
| 64 | 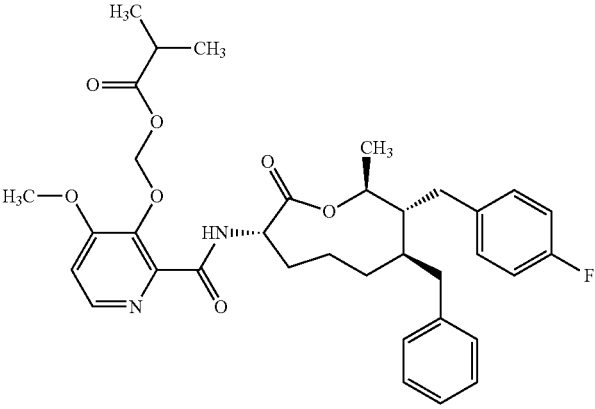 [SMILES: COc1ccnc(C(=O)N[C@H]2CCC[C@H](Cc3ccccc3)[C@@H](Cc3ccc(F)cc3)[C@H](C)OC2=O)c1OCOC(=O)C(C)C] | Example 8 | Colorless Oil |
| 65 | 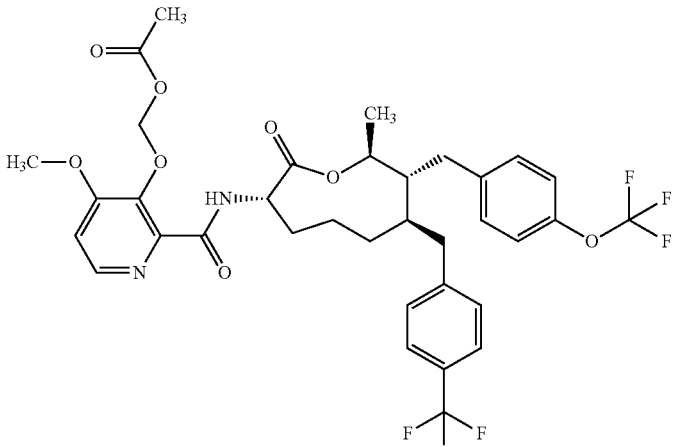 | Example 6 | Colorless Foam |

TABLE 1-continued

Compound Structure and Appearance

| *Cmpd. No. | Structure | Prepared According to Example | Appearance |
|---|---|---|---|
| 66 | 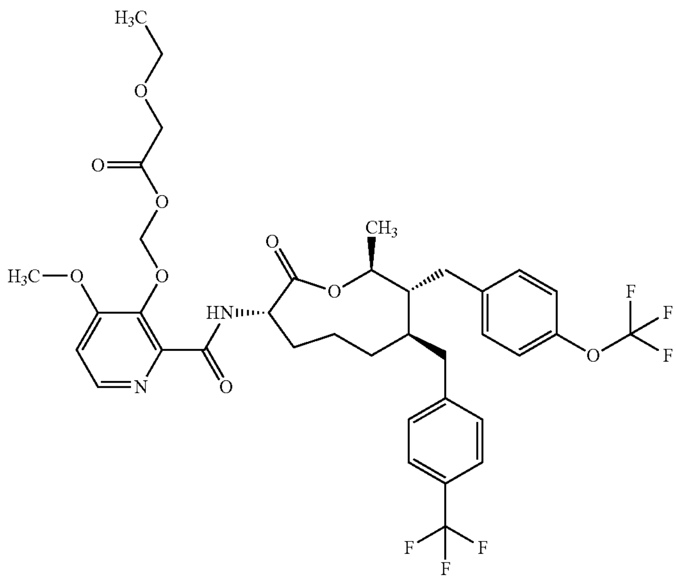 [SMILES: CCOCC(=O)OCOc1c(OC)ccnc1C(=O)N[C@H]1CCC[C@H](Cc2ccc(C(F)(F)F)cc2)[C@@H](Cc2ccc(OC(F)(F)F)cc2)[C@H](C)OC1=O] | Example 9 | Colorless Foam |
| 67 | 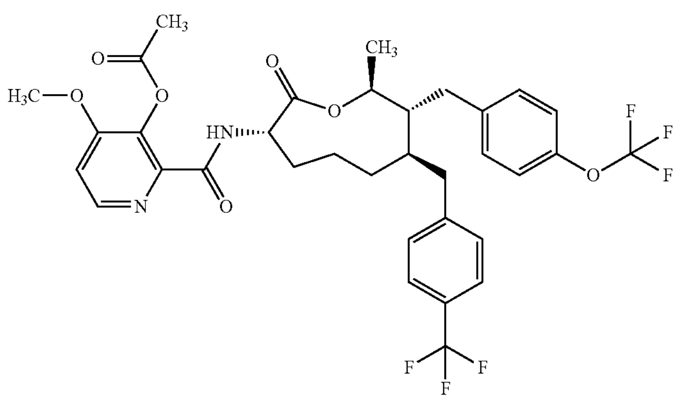 [SMILES: COc1ccnc(C(=O)N[C@H]2CCC[C@H](Cc3ccc(C(F)(F)F)cc3)[C@@H](Cc3ccc(OC(F)(F)F)cc3)[C@H](C)OC2=O)c1OC(C)=O] | Example 7 | Pale Yellow Foam |
| 68 | 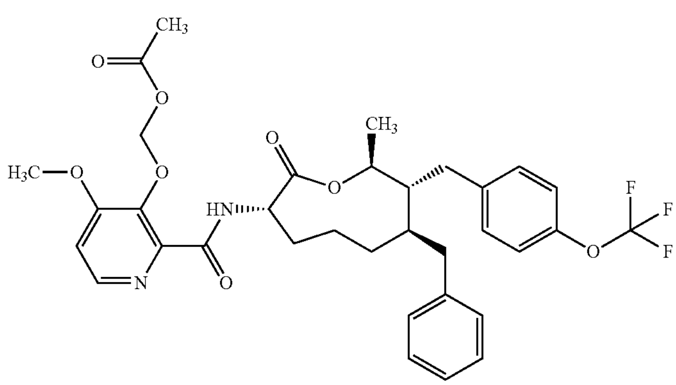 [SMILES: COc1ccnc(C(=O)N[C@H]2CCC[C@H](Cc3ccccc3)[C@@H](Cc3ccc(OC(F)(F)F)cc3)[C@H](C)OC2=O)c1OCOC(C)=O] | Example 6 | Colorless Foam |

TABLE 1-continued
Compound Structure and Appearance
| *Cmpd. No. | Structure | Prepared According to Example | Appearance |
|---|---|---|---|
| 69 | 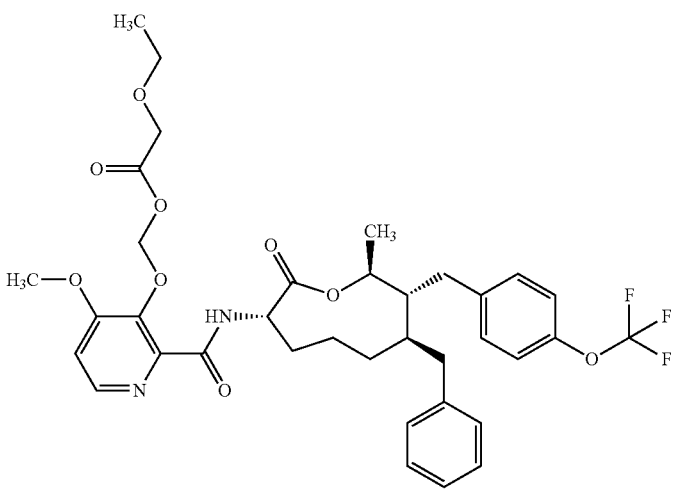 [SMILES: CCOCC(=O)OCOc1c(OC)ccnc1C(=O)N[C@H]1CCC[C@H](Cc2ccccc2)[C@@H](Cc2ccc(OC(F)(F)F)cc2)[C@H](C)OC1=O] | Example 9 | Colorless Foam |
| 70 | 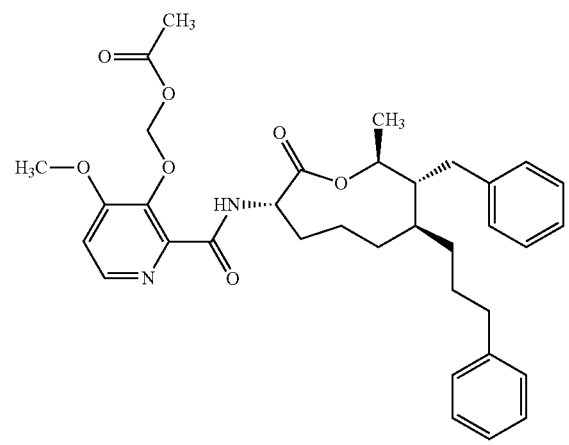 [SMILES: COc1ccnc(C(=O)N[C@H]2CCC[C@H](CCCc3ccccc3)[C@@H](Cc3ccccc3)[C@H](C)OC2=O)c1OCOC(C)=O] | Example 6 | Colorless Foam |
| 71 | 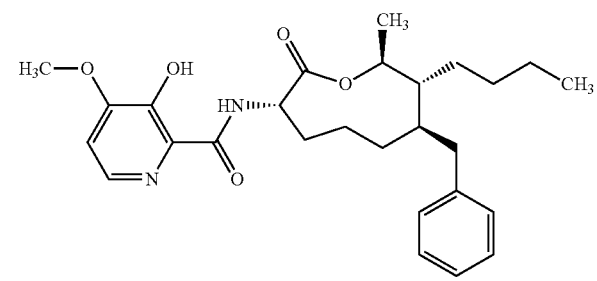 [SMILES: CCCC[C@@H]1[C@@H](Cc2ccccc2)CCC[C@H](NC(=O)c2nccc(OC)c2O)C(=O)O[C@H]1C] | Example 5, Step 2 | Colorless Oil |

TABLE 1-continued
Compound Structure and Appearance
| *Cmpd. No. | Structure | Prepared According to Example | Appearance |
|---|---|---|---|
| 72 | 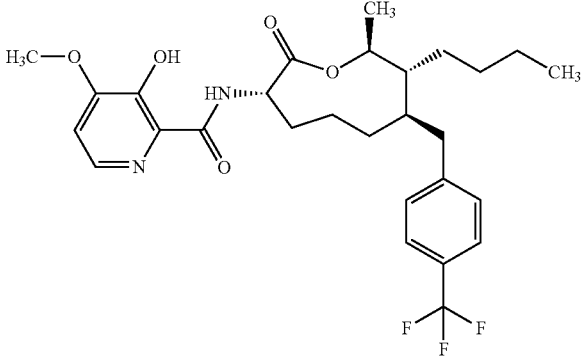 [SMILES: CCCC[C@@H]1[C@@H](Cc2ccc(C(F)(F)F)cc2)CCC[C@H](NC(=O)c2nccc(OC)c2O)C(=O)O[C@H]1C] | Example 5, Step 2 | White Foam |
| 73 | 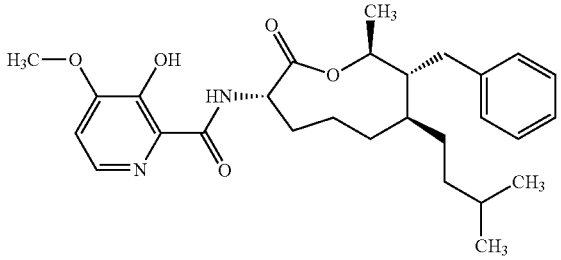 [SMILES: COc1ccnc(C(=O)N[C@H]2CCC[C@H](CCC(C)C)[C@@H](Cc3ccccc3)[C@H](C)OC2=O)c1O] | Example 5, Step 2 | White Foam |
| 74 | 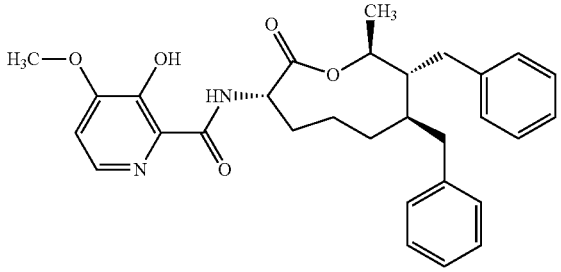 [SMILES: COc1ccnc(C(=O)N[C@H]2CCC[C@H](Cc3ccccc3)[C@@H](Cc3ccccc3)[C@H](C)OC2=O)c1O] | Example 5, Step 2 | White Foam |
| 75 | 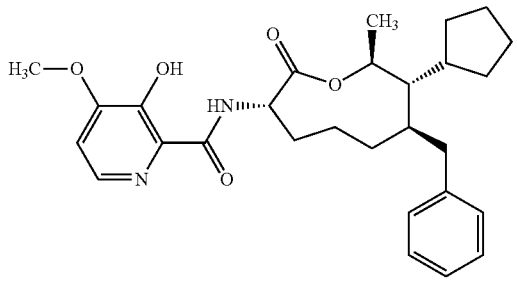 [SMILES: COc1ccnc(C(=O)N[C@H]2CCC[C@H](Cc3ccccc3)[C@@H](C3CCCC3)[C@H](C)OC2=O)c1O] | Example 5, Step 2 | Colorless Foam |

TABLE 1-continued

Compound Structure and Appearance

| *Cmpd. No. | Structure | Prepared According to Example | Appearance |
|---|---|---|---|
| 76 | 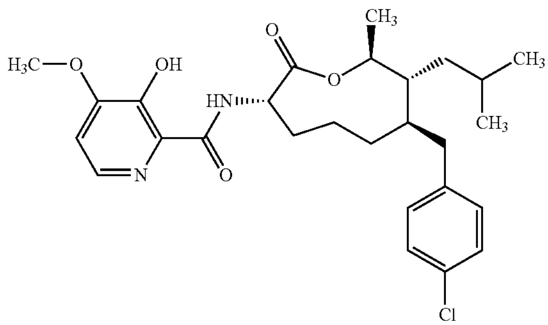 [SMILES: COc1ccnc(C(=O)N[C@H]2CCC[C@H](Cc3ccc(Cl)cc3)[C@@H](CC(C)C)[C@H](C)OC2=O)c1O] | Example 5, Step 2 | Colorless Oil |
| 77 | 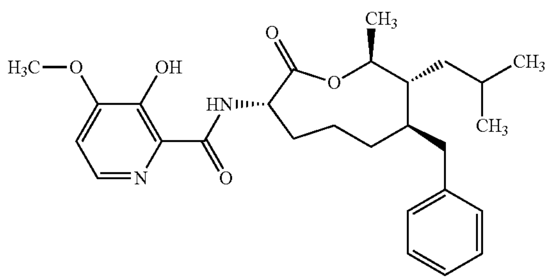 [SMILES: COc1ccnc(C(=O)N[C@H]2CCC[C@H](Cc3ccccc3)[C@@H](CC(C)C)[C@H](C)OC2=O)c1O] | Example 5, Step 2 | White Solid |
| 78 | 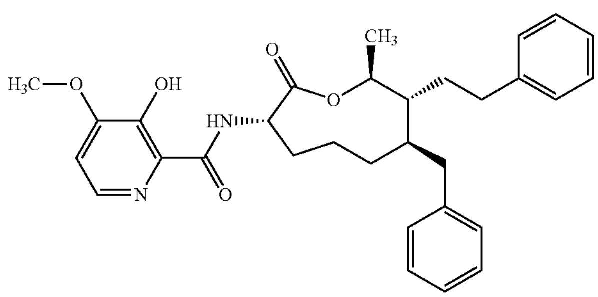 [SMILES: COc1ccnc(C(=O)N[C@H]2CCC[C@H](Cc3ccccc3)[C@@H](CCc3ccccc3)[C@H](C)OC2=O)c1O] | Example 5, Step 2 | Colorless Solid |
| 79 | 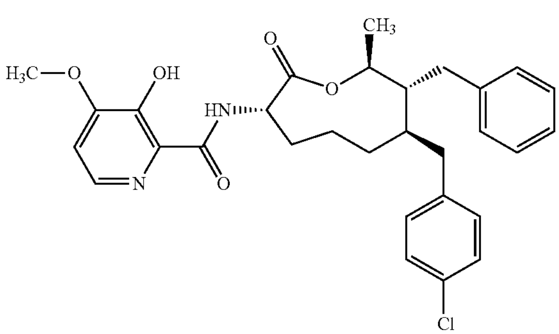 [SMILES: COc1ccnc(C(=O)N[C@H]2CCC[C@H](Cc3ccc(Cl)cc3)[C@@H](Cc3ccccc3)[C@H](C)OC2=O)c1O] | Example 5, Step 2 | Colorless Solid |

TABLE 1-continued

Compound Structure and Appearance

| *Cmpd. No. | Structure | Prepared According to Example | Appearance |
|---|---|---|---|
| 80 | 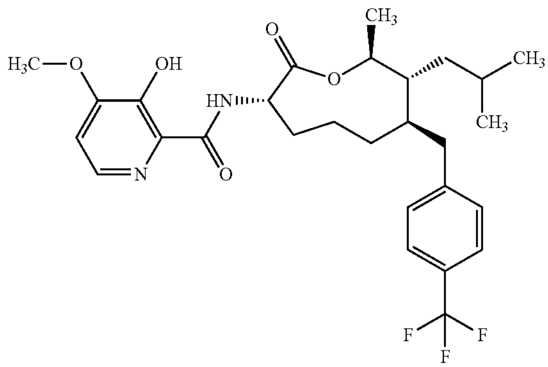 [SMILES: COc1ccnc(C(=O)N[C@H]2CCC[C@H](Cc3ccc(C(F)(F)F)cc3)[C@@H](CC(C)C)[C@H](C)OC2=O)c1O] | Example 5, Step 2 | White Foam |
| 81 | 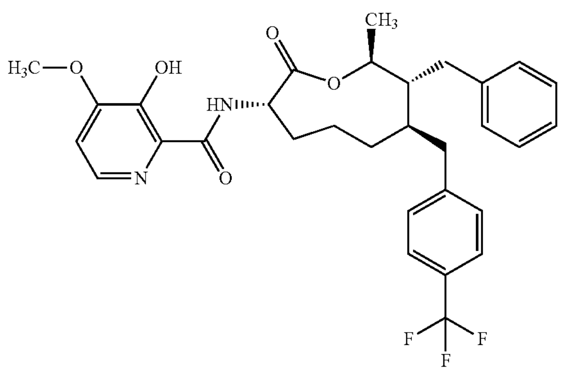 [SMILES: COc1ccnc(C(=O)N[C@H]2CCC[C@H](Cc3ccc(C(F)(F)F)cc3)[C@@H](Cc3ccccc3)[C@H](C)OC2=O)c1O] | Example 5, Step 2 | Colorless Oil |
| 82 | 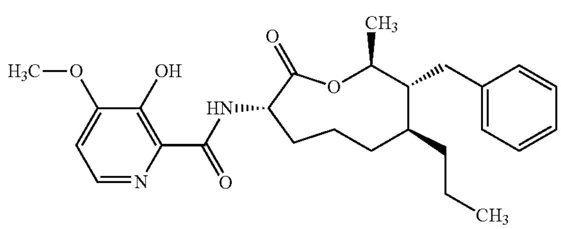 [SMILES: CCC[C@H]1CCC[C@H](NC(=O)c2nccc(OC)c2O)C(=O)O[C@@H](C)[C@@H]1Cc1ccccc1] | Example 5, Step 2 | Colorless Solid |
| 83 | 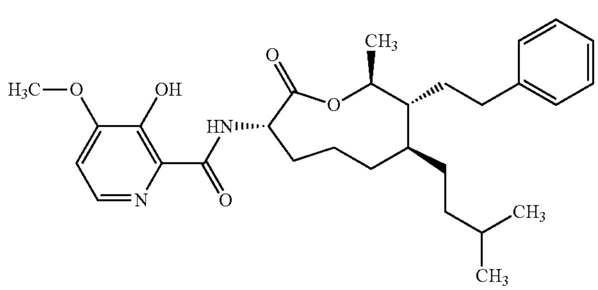 [SMILES: COc1ccnc(C(=O)N[C@H]2CCC[C@H](CCC(C)C)[C@@H](CCc3ccccc3)[C@H](C)OC2=O)c1O] | Example 5, Step 2 | Colorless Solid |

TABLE 1-continued

Compound Structure and Appearance

| *Cmpd. No. | Structure | Prepared According to Example | Appearance |
|---|---|---|---|
| 84 | 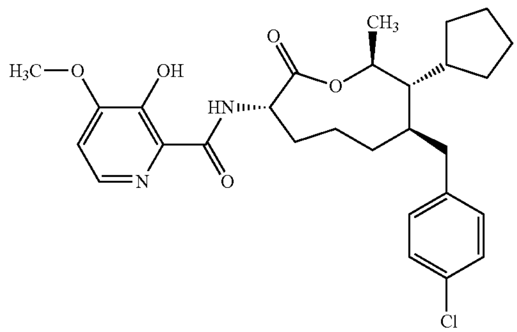 [SMILES: COc1ccnc(C(=O)N[C@H]2CCC[C@H](Cc3ccc(Cl)cc3)[C@@H](C3CCCC3)[C@H](C)OC2=O)c1O] | Example 5, Step 2 | Colorless Oil |
| 85 | 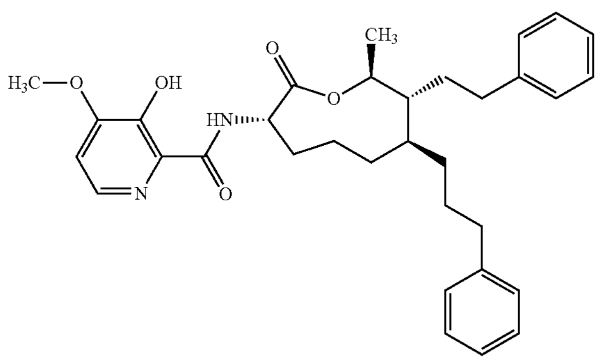 [SMILES: COc1ccnc(C(=O)N[C@H]2CCC[C@H](CCCc3ccccc3)[C@@H](CCc3ccccc3)[C@H](C)OC2=O)c1O] | Example 5, Step 2 | White Foam |
| 86 | 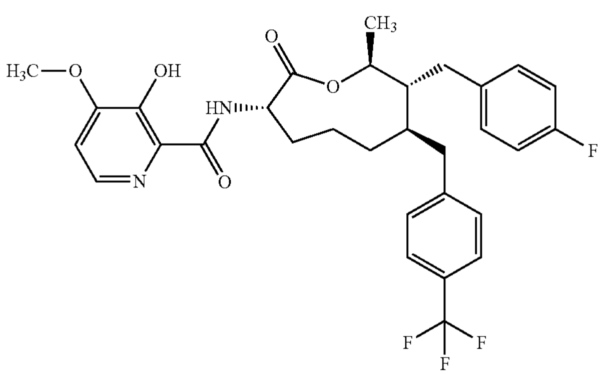 [SMILES: COc1ccnc(C(=O)N[C@H]2CCC[C@H](Cc3ccc(C(F)(F)F)cc3)[C@@H](Cc3ccc(F)cc3)[C@H](C)OC2=O)c1O] | Example 5, Step 2 | White Foam |
| 87 | 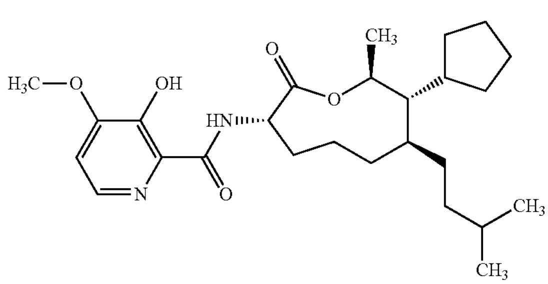 [SMILES: COc1ccnc(C(=O)N[C@H]2CCC[C@H](CCC(C)C)[C@@H](C3CCCC3)[C@H](C)OC2=O)c1O] | Example 5, Step 2 | White Powder |

TABLE 1-continued

Compound Structure and Appearance

| *Cmpd. No. | Structure | Prepared According to Example | Appearance |
|---|---|---|---|
| 88 | 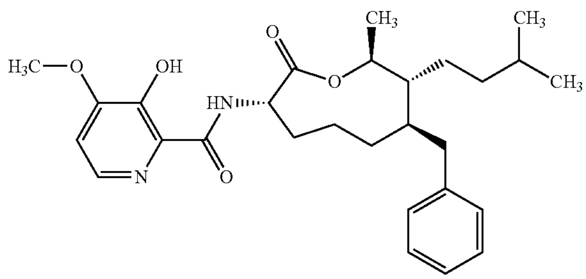 [SMILES: COc1ccnc(C(=O)N[C@H]2CCC[C@H](Cc3ccccc3)[C@@H](CCC(C)C)[C@H](C)OC2=O)c1O] | Example 5, Step 2 | Colorless Oil |
| 89 | 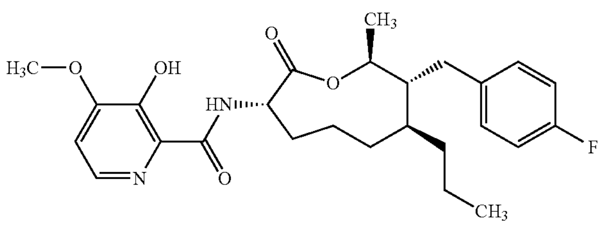 [SMILES: CCC[C@H]1CCC[C@H](NC(=O)c2nccc(OC)c2O)C(=O)O[C@@H](C)[C@@H]1Cc1ccc(F)cc1] | Example 5, Step 2 | Colorless Oil |
| 90 | 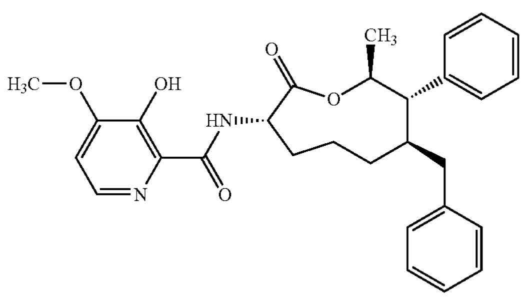 [SMILES: COc1ccnc(C(=O)N[C@H]2CCC[C@H](Cc3ccccc3)[C@@H](c3ccccc3)[C@H](C)OC2=O)c1O] | Example 5, Step 2 | White Foam |
| 91 | 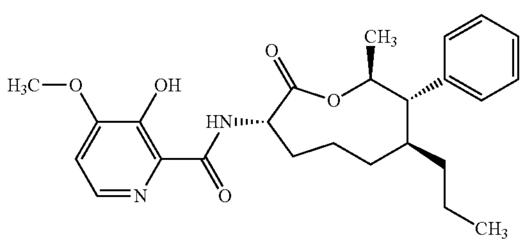 [SMILES: CCC[C@H]1CCC[C@H](NC(=O)c2nccc(OC)c2O)C(=O)O[C@@H](C)[C@@H]1c1ccccc1] | Example 5, Step 2 | White Foam |
| 92 | 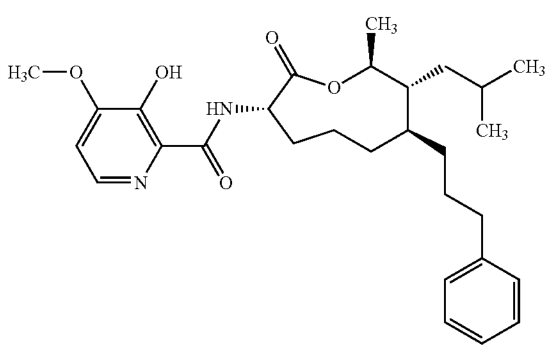 [SMILES: COc1ccnc(C(=O)N[C@H]2CCC[C@H](CCCc3ccccc3)[C@@H](CC(C)C)[C@H](C)OC2=O)c1O] | Example 5, Step 2 | White Foam |

TABLE 1-continued

Compound Structure and Appearance

| *Cmpd. No. | Structure | Prepared According to Example | Appearance |
|---|---|---|---|
| 93 | 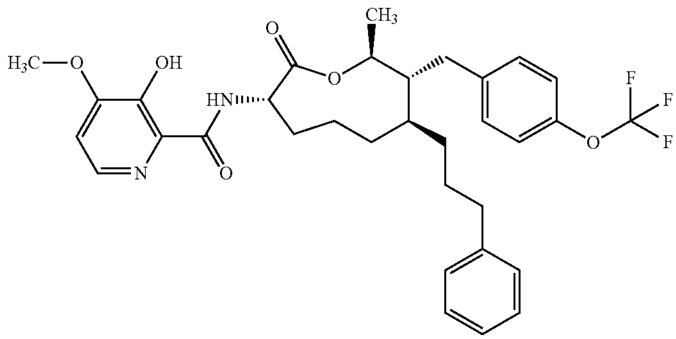 [SMILES: COc1ccnc(C(=O)N[C@H]2CCC[C@H](CCCc3ccccc3)[C@@H](Cc3ccc(OC(F)(F)F)cc3)[C@H](C)OC2=O)c1O] | Example 5, Step 2 | White Solid |
| 94 | 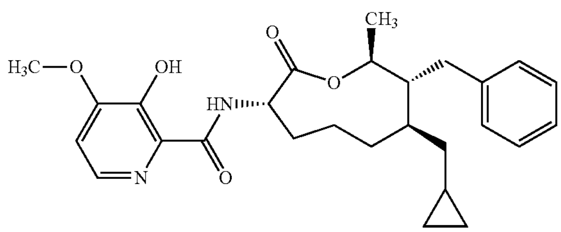 [SMILES: COc1ccnc(C(=O)N[C@H]2CCC[C@H](CC3CC3)[C@@H](Cc3ccccc3)[C@H](C)OC2=O)c1O] | Example 5, Step 2 | White Foam |
| 95 | 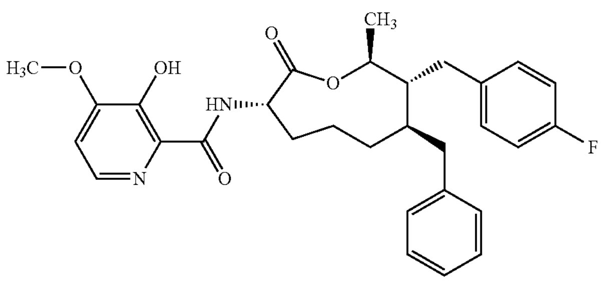 [SMILES: COc1ccnc(C(=O)N[C@H]2CCC[C@H](Cc3ccccc3)[C@@H](Cc3ccc(F)cc3)[C@H](C)OC2=O)c1O] | Example 5, Step 2 | White Foam |
| 96 | 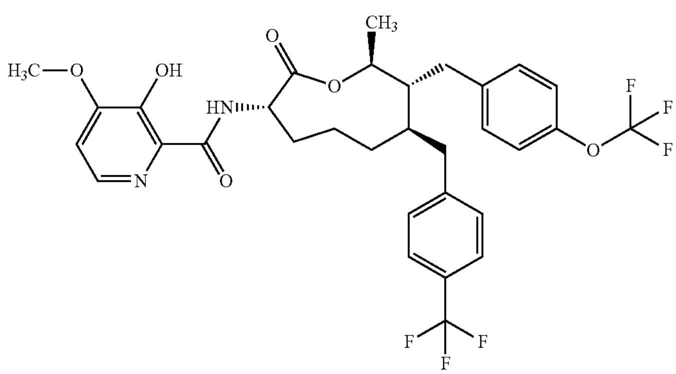 [SMILES: COc1ccnc(C(=O)N[C@H]2CCC[C@H](Cc3ccc(C(F)(F)F)cc3)[C@@H](Cc3ccc(OC(F)(F)F)cc3)[C@H](C)OC2=O)c1O] | Example 5, Step 2 | Colorless Solid |
| 97 | 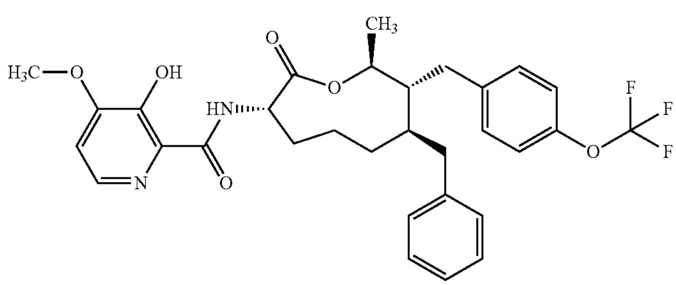 [SMILES: COc1ccnc(C(=O)N[C@H]2CCC[C@H](Cc3ccccc3)[C@@H](Cc3ccc(OC(F)(F)F)cc3)[C@H](C)OC2=O)c1O] | Example 5, Step 2 | Colorless Solid |

TABLE 1-continued

Compound Structure and Appearance

| *Cmpd. No. | Structure | Prepared According to Example | Appearance |
|---|---|---|---|
| 98 | 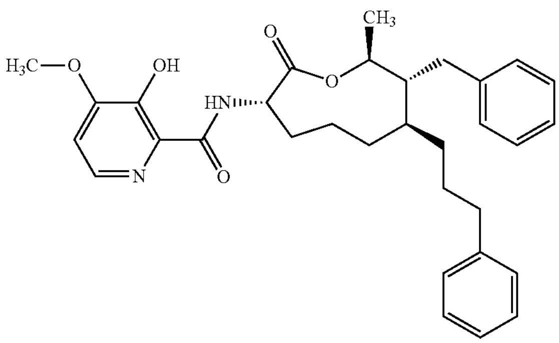 [SMILES: COc1ccnc(C(=O)N[C@H]2CCC[C@H](CCCc3ccccc3)[C@@H](Cc3ccccc3)[C@H](C)OC2=O)c1O] | Example 5, Step 2 | Thick Colorless Oil |
| 99 | 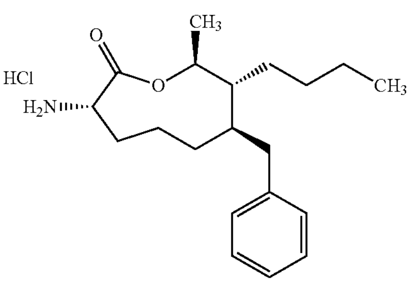 [SMILES: Cl ; CCCC[C@@H]1[C@@H](Cc2ccccc2)CCC[C@H](N)C(=O)O[C@H]1C] | Example 5, Step 1 | White Solid |
| 100 | 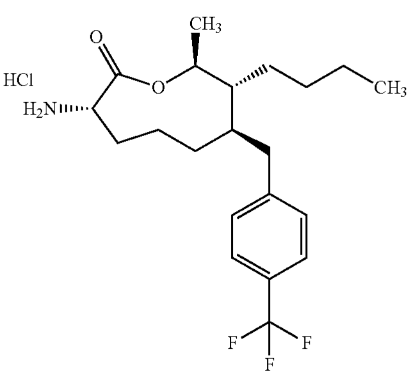 [SMILES: Cl ; CCCC[C@@H]1[C@@H](Cc2ccc(C(F)(F)F)cc2)CCC[C@H](N)C(=O)O[C@H]1C] | Example 5, Step 1 | White Solid |
| 101 | 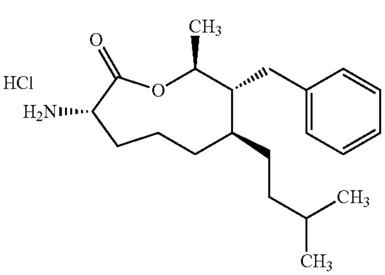 [SMILES: Cl ; CC(C)CC[C@H]1CCC[C@H](N)C(=O)O[C@@H](C)[C@@H]1Cc1ccccc1] | Example 5, Step 1 | White Foam |

TABLE 1-continued

Compound Structure and Appearance

| *Cmpd. No. | Structure | Prepared According to Example | Appearance |
|---|---|---|---|
| 102 | 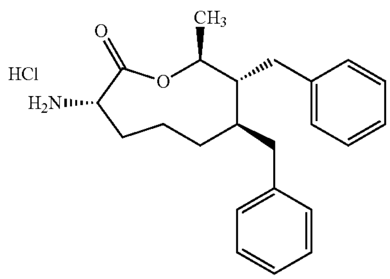 [SMILES: Cl ; C[C@@H]1OC(=O)[C@@H](N)CCC[C@H](Cc2ccccc2)[C@H]1Cc1ccccc1] | Example 5, Step 1 | White Foam |
| 103 | 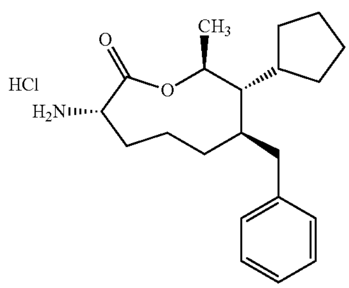 [SMILES: Cl ; C[C@@H]1OC(=O)[C@@H](N)CCC[C@H](Cc2ccccc2)[C@H]1C1CCCC1] | Example 5, Step 1 | White Solid |
| 104 | 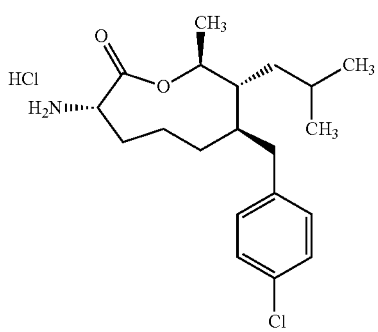 [SMILES: Cl ; CC(C)C[C@@H]1[C@@H](Cc2ccc(Cl)cc2)CCC[C@H](N)C(=O)O[C@H]1C] | Example 5, Step 1 | White Solid |
| 105 | 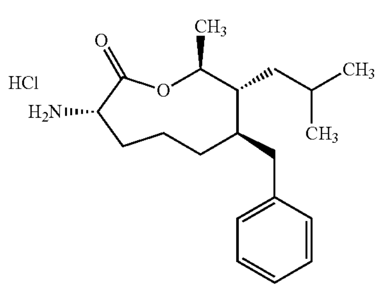 [SMILES: Cl ; CC(C)C[C@@H]1[C@@H](Cc2ccccc2)CCC[C@H](N)C(=O)O[C@H]1C] | Example 5, Step 1 | White Solid |

TABLE 1-continued

Compound Structure and Appearance

| *Cmpd. No. | Structure | Prepared According to Example | Appearance |
|---|---|---|---|
| 106 | 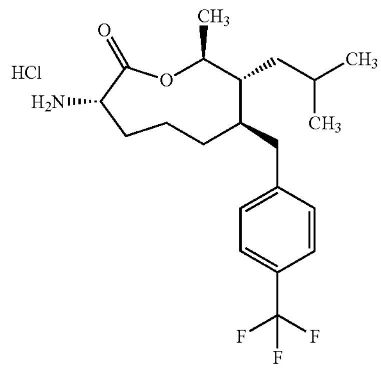 [SMILES: Cl ; CC(C)C[C@@H]1[C@@H](Cc2ccc(C(F)(F)F)cc2)CCC[C@H](N)C(=O)O[C@H]1C] | Example 5, Step 1 | White Foam |
| 107 | 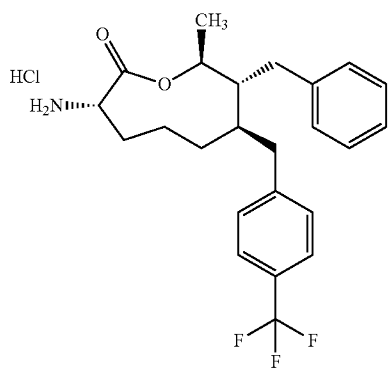 [SMILES: Cl ; C[C@@H]1OC(=O)[C@@H](N)CCC[C@H](Cc2ccc(C(F)(F)F)cc2)[C@H]1Cc1ccccc1] | Example 5, Step 1 | Colorless Oil |
| 108 | 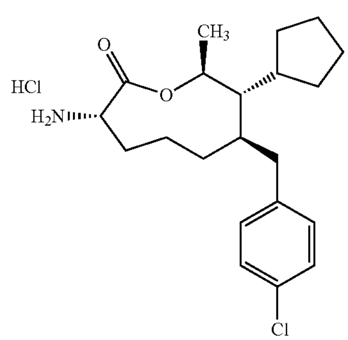 [SMILES: Cl ; C[C@@H]1OC(=O)[C@@H](N)CCC[C@H](Cc2ccc(Cl)cc2)[C@H]1C1CCCC1] | Example 5, Step 1 | White Solid |
| 109 | 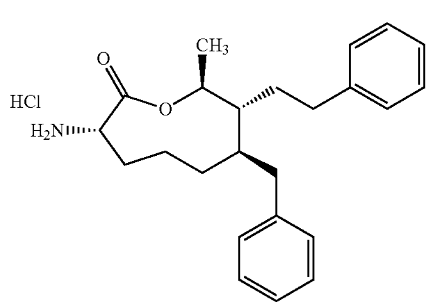 [SMILES: Cl ; C[C@@H]1OC(=O)[C@@H](N)CCC[C@H](Cc2ccccc2)[C@H]1CCc1ccccc1] | Example 5, Step 1 | White Solid |

TABLE 1-continued
Compound Structure and Appearance
| *Cmpd. No. | Structure | Prepared According to Example | Appearance |
|---|---|---|---|
| 110 | 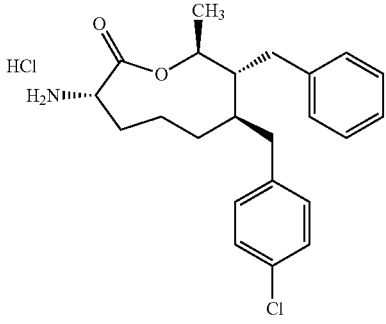 [SMILES: Cl ; C[C@@H]1OC(=O)[C@@H](N)CCC[C@H](Cc2ccc(Cl)cc2)[C@H]1Cc1ccccc1] | Example 5, Step 1 | White Solid |
| 111 | 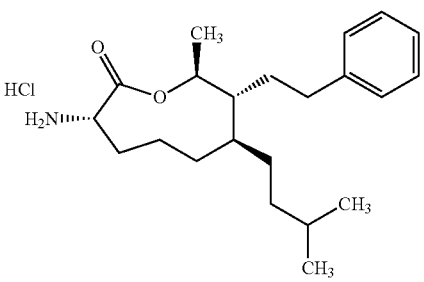 [SMILES: Cl ; CC(C)CC[C@H]1CCC[C@H](N)C(=O)O[C@@H](C)[C@@H]1CCc1ccccc1] | Example 5, Step 1 | Off-White Solid |
| 112 | 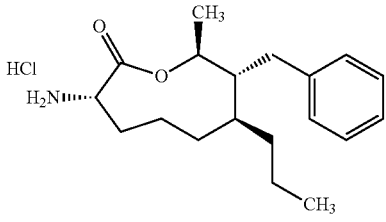 [SMILES: Cl ; CCC[C@H]1CCC[C@H](N)C(=O)O[C@@H](C)[C@@H]1Cc1ccccc1] | Example 5, Step 1 | Off-White Solid |
| 113 | 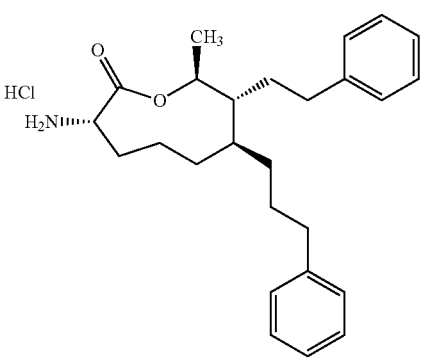 [SMILES: Cl ; C[C@@H]1OC(=O)[C@@H](N)CCC[C@H](CCCc2ccccc2)[C@H]1CCc1ccccc1] | Example 5, Step 1 | Yellow Foam |

TABLE 1-continued
Compound Structure and Appearance
| *Cmpd. No. | Structure | Prepared According to Example | Appearance |
|---|---|---|---|
| 114 | 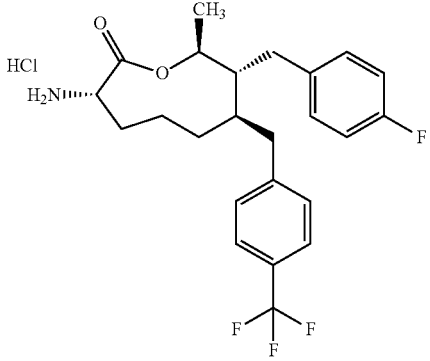 [SMILES: Cl ; C[C@@H]1OC(=O)[C@@H](N)CCC[C@H](Cc2ccc(C(F)(F)F)cc2)[C@H]1Cc1ccc(F)cc1] | Example 5, Step 1 | White Solid |
| 115 | 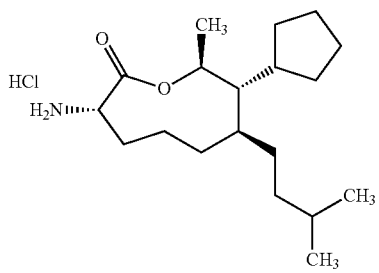 [SMILES: Cl ; CC(C)CC[C@H]1CCC[C@H](N)C(=O)O[C@@H](C)[C@@H]1C1CCCC1] | Example 5, Step 1 | White Solid |
| 116 | 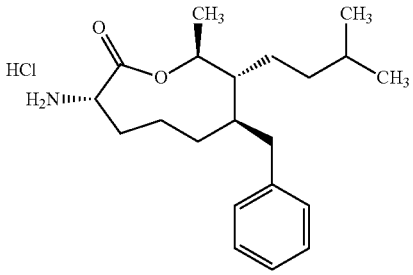 [SMILES: Cl ; CC(C)CC[C@@H]1[C@@H](Cc2ccccc2)CCC[C@H](N)C(=O)O[C@H]1C] | Example 5, Step 1 | White Solid |
| 117 | 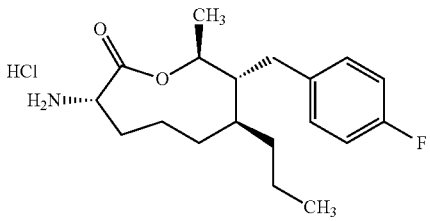 [SMILES: Cl ; CCC[C@H]1CCC[C@H](N)C(=O)O[C@@H](C)[C@@H]1Cc1ccc(F)cc1] | Example 5, Step 1 | White Solid |
| 118 | 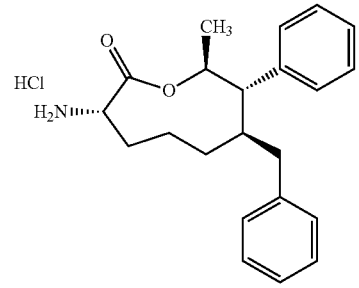 [SMILES: Cl ; C[C@@H]1OC(=O)[C@@H](N)CCC[C@H](Cc2ccccc2)[C@H]1c1ccccc1] | Example 5, Step 1 | White Foam |

TABLE 1-continued

Compound Structure and Appearance

| *Cmpd. No. | Structure | Prepared According to Example | Appearance |
|---|---|---|---|
| 119 | 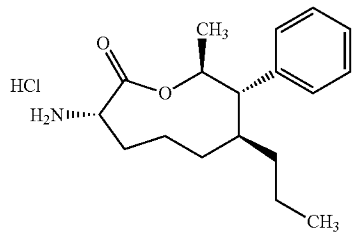 [SMILES: Cl ; CCC[C@H]1CCC[C@H](N)C(=O)O[C@@H](C)[C@@H]1c1ccccc1] | Example 5, Step 1 | White Foam |
| 120 | 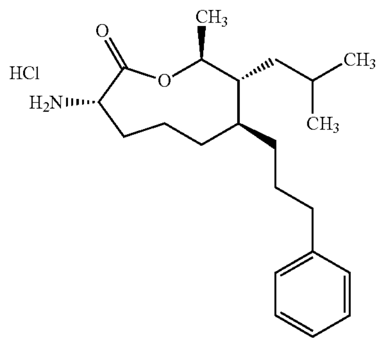 [SMILES: Cl ; CC(C)C[C@@H]1[C@@H](CCCc2ccccc2)CCC[C@H](N)C(=O)O[C@H]1C] | Example 5, Step 1 | White Solid |
| 121 | 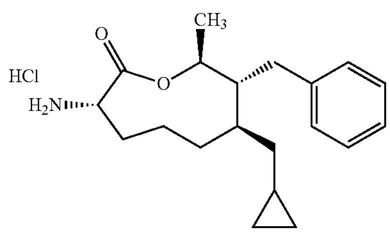 [SMILES: Cl ; C[C@@H]1OC(=O)[C@@H](N)CCC[C@H](CC2CC2)[C@H]1Cc1ccccc1] | Example 5, Step 1 | White Solid |
| 122 | 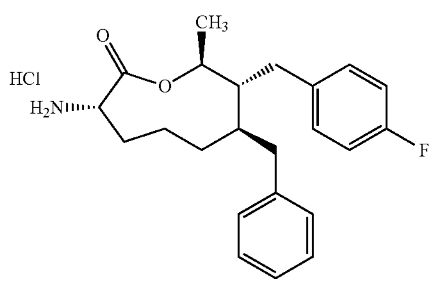 [SMILES: Cl ; C[C@@H]1OC(=O)[C@@H](N)CCC[C@H](Cc2ccccc2)[C@H]1Cc1ccc(F)cc1] | Example 5, Step 1 | White Foam |
| 123 | 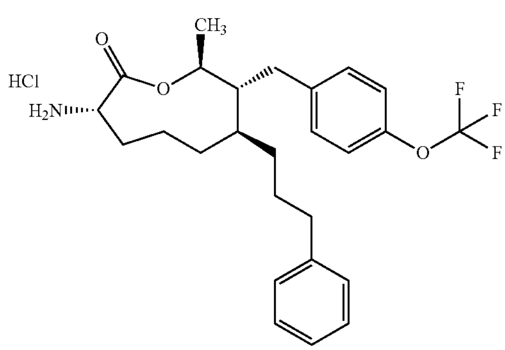 [SMILES: Cl ; C[C@@H]1OC(=O)[C@@H](N)CCC[C@H](CCCc2ccccc2)[C@H]1Cc1ccc(OC(F)(F)F)cc1] | Example 5, Step 1 | White Solid |

TABLE 1-continued

Compound Structure and Appearance

| *Cmpd. No. | Structure | Prepared According to Example | Appearance |
|---|---|---|---|
| 124 | 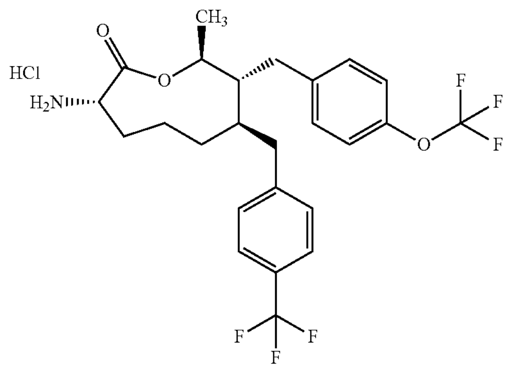 [SMILES: Cl ; C[C@@H]1OC(=O)[C@@H](N)CCC[C@H](Cc2ccc(C(F)(F)F)cc2)[C@H]1Cc1ccc(OC(F)(F)F)cc1] | Example 5, Step 1 | White Solid |
| 125 | 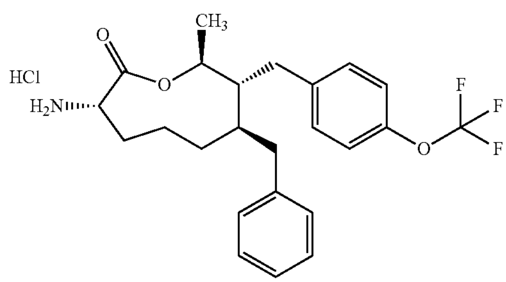 [SMILES: Cl ; C[C@@H]1OC(=O)[C@@H](N)CCC[C@H](Cc2ccccc2)[C@H]1Cc1ccc(OC(F)(F)F)cc1] | Example 5, Step 1 | White Solid |
| 126 | 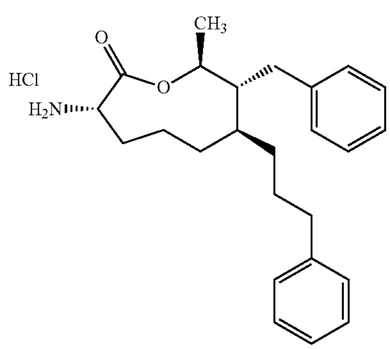 [SMILES: Cl ; C[C@@H]1OC(=O)[C@@H](N)CCC[C@H](CCCc2ccccc2)[C@H]1Cc1ccccc1] | Example 5, Step 1 | White Solid |
| 127 | 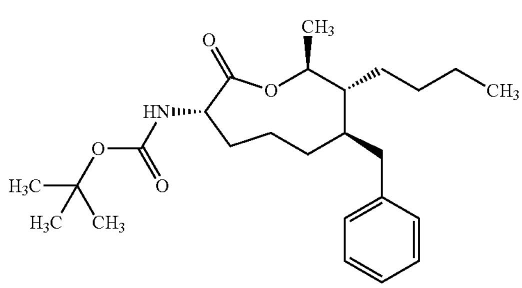 [SMILES: CCCC[C@@H]1[C@@H](Cc2ccccc2)CCC[C@H](NC(=O)OC(C)(C)C)C(=O)O[C@H]1C] | Example 1, Steps 1-3; Example 2, Steps 1a-c, Step 2; Example 3, Steps 1-3; Example 4 | Colorless Oil |

TABLE 1-continued

Compound Structure and Appearance

| *Cmpd. No. | Structure | Prepared According to Example | Appearance |
|---|---|---|---|
| 128 | 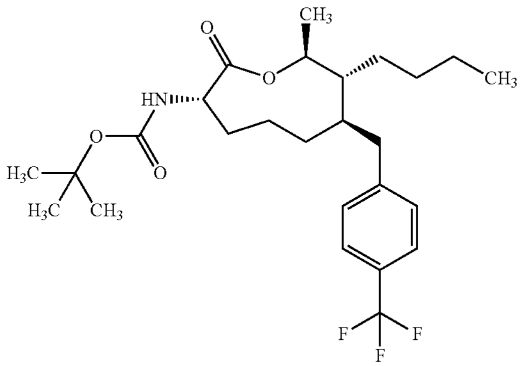 [SMILES: CCCC[C@@H]1[C@@H](Cc2ccc(C(F)(F)F)cc2)CCC[C@H](NC(=O)OC(C)(C)C)C(=O)O[C@H]1C] | Example 1, Steps 1-3; Example 2, Steps 1a-c, Step 2; Example 3, Steps 1-3; Example 4 | Colorless Oil |
| 129 | 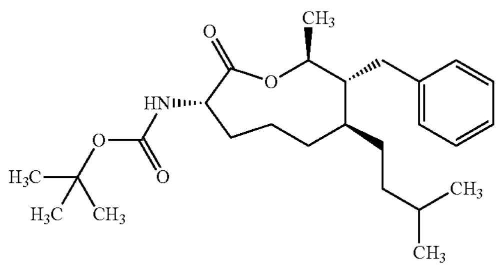 [SMILES: CC(C)CC[C@H]1CCC[C@H](NC(=O)OC(C)(C)C)C(=O)O[C@@H](C)[C@@H]1Cc1ccccc1] | Example 1, Steps 1-3; Example 2, Steps 1a-c, Step 2; Example 3, Steps 1-3; Example 4 | Colorless Oil |
| 130 | 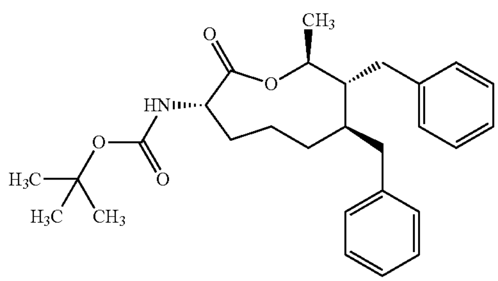 [SMILES: C[C@@H]1OC(=O)[C@@H](NC(=O)OC(C)(C)C)CCC[C@H](Cc2ccccc2)[C@H]1Cc1ccccc1] | Example 1, Steps 1-3; Example 2, Steps 1a-c, Step 2; Example 3, Steps 1-3; Example 4 | Colorless Oil |
| 131 | 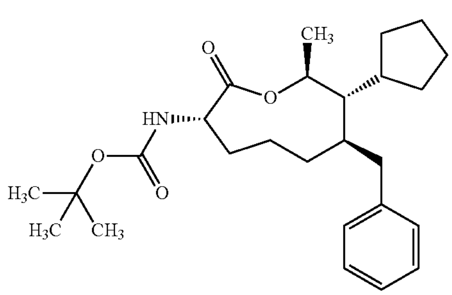 [SMILES: C[C@@H]1OC(=O)[C@@H](NC(=O)OC(C)(C)C)CCC[C@H](Cc2ccccc2)[C@H]1C1CCCC1] | Example 1, Steps 1-3; Example 2, Steps 1a-c, Step 2; Example 3, Steps 1-3; Example 4 | Colorless Oil |

TABLE 1-continued

Compound Structure and Appearance

| *Cmpd. No. | Structure | Prepared According to Example | Appearance |
|---|---|---|---|
| 132 | 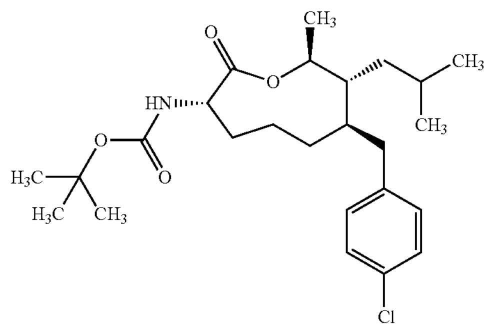 [SMILES: CC(C)C[C@@H]1[C@@H](Cc2ccc(Cl)cc2)CCC[C@H](NC(=O)OC(C)(C)C)C(=O)O[C@H]1C] | Example 1, Steps 1-3; Example 2, Steps 1a-c, Step 2; Example 3, Steps 1-3; Example 4 | Colorless Oil |
| 133 | 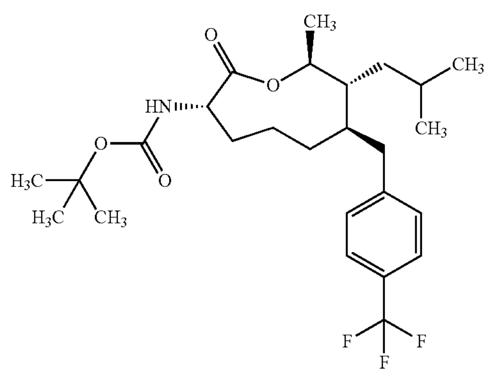 [SMILES: CC(C)C[C@@H]1[C@@H](Cc2ccc(C(F)(F)F)cc2)CCC[C@H](NC(=O)OC(C)(C)C)C(=O)O[C@H]1C] | Example 1, Steps 1-3; Example 2, Steps 1a-c, Step 2; Example 3, Steps 1-3; Example 4 | Colorless Oil |
| 134 | 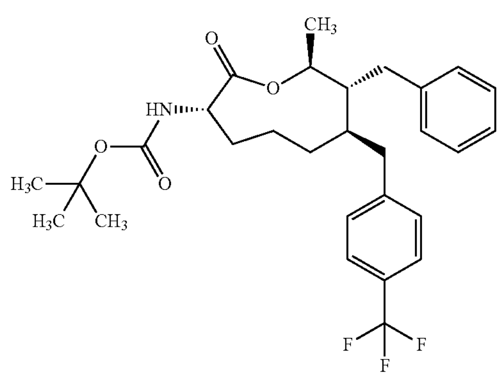 [SMILES: C[C@@H]1OC(=O)[C@@H](NC(=O)OC(C)(C)C)CCC[C@H](Cc2ccc(C(F)(F)F)cc2)[C@H]1Cc1ccccc1] | Example 1, Steps 1-3; Example 2, Steps 1a-c, Step 2; Example 3, Steps 1-3; Example 4 | Colorless Oil |
| 135 | 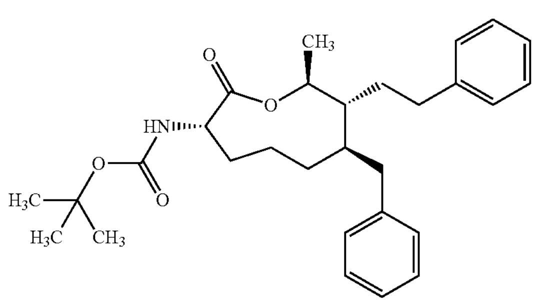 [SMILES: C[C@@H]1OC(=O)[C@@H](NC(=O)OC(C)(C)C)CCC[C@H](Cc2ccccc2)[C@H]1CCc1ccccc1] | Example 1, Steps 1-3; Example 2, Steps 1a-c, Step 2; Example 3, Steps 1-3; Example 4 | Colorless Foam |

TABLE 1-continued

Compound Structure and Appearance

| *Cmpd. No. | Structure | Prepared According to Example | Appearance |
|---|---|---|---|
| 136 | 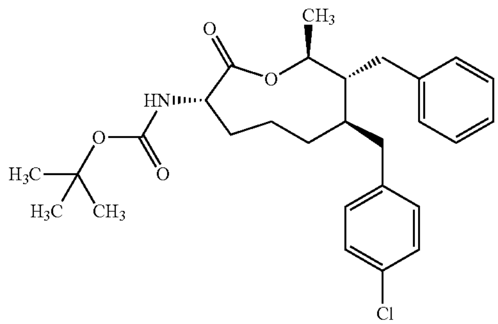 [SMILES: C[C@@H]1OC(=O)[C@@H](NC(=O)OC(C)(C)C)CCC[C@H](Cc2ccc(Cl)cc2)[C@H]1Cc1ccccc1] | Example 1, Steps 1-3; Example 2, Steps 1a-c, Step 2; Example 3, Steps 1-3; Example 4 | Colorless Oil |
| 137 | 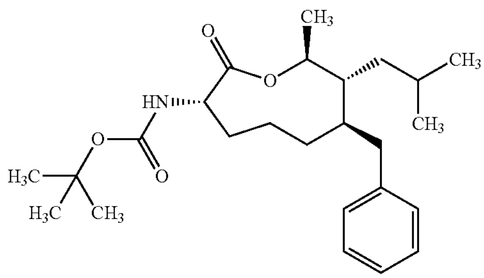 [SMILES: CC(C)C[C@@H]1[C@@H](Cc2ccccc2)CCC[C@H](NC(=O)OC(C)(C)C)C(=O)O[C@H]1C] | Example 1, Steps 1-3; Example 2, Steps 1a-c, Step 2; Example 3, Steps 1-3; Example 4 | Colorless Oil |
| 138 | 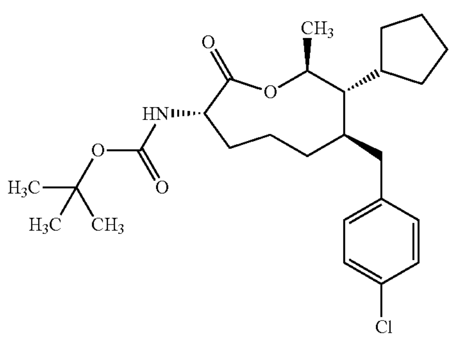 [SMILES: C[C@@H]1OC(=O)[C@@H](NC(=O)OC(C)(C)C)CCC[C@H](Cc2ccc(Cl)cc2)[C@H]1C1CCCC1] | Example 1, Steps 1-3; Example 2, Steps 1a-c, Step 2; Example 3, Steps 1-3; Example 4 | Colorless Oil |
| 139 | 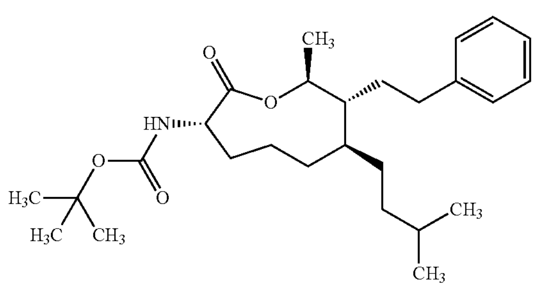 [SMILES: CC(C)CC[C@H]1CCC[C@H](NC(=O)OC(C)(C)C)C(=O)O[C@@H](C)[C@@H]1CCc1ccccc1] | Example 1, Steps 1-3; Example 2, Steps 1a-c, Step 2; Example 3, Steps 1-3; Example 4 | Colorless Oil |
| 140 | 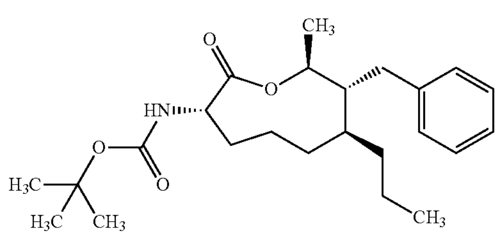 [SMILES: CCC[C@H]1CCC[C@H](NC(=O)OC(C)(C)C)C(=O)O[C@@H](C)[C@@H]1Cc1ccccc1] | Example 1, Steps 1-3; Example 2, Steps 1a-c, Step 2; Example 3, Steps 1-3; Example 4 | White Solid |

TABLE 1-continued

Compound Structure and Appearance

| *Cmpd. No. | Structure | Prepared According to Example | Appearance |
|---|---|---|---|
| 141 | 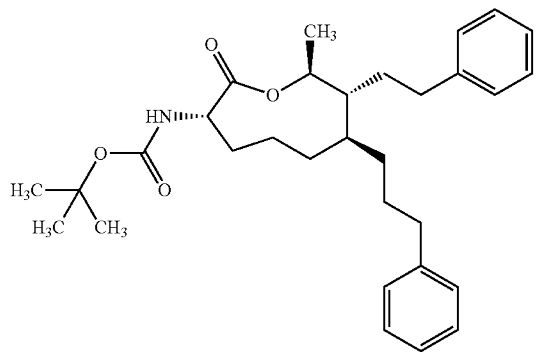 [SMILES: C[C@@H]1OC(=O)[C@@H](NC(=O)OC(C)(C)C)CCC[C@H](CCCc2ccccc2)[C@H]1CCc1ccccc1] | Example 1, Steps 1-3; Example 2, Steps 1a-c, Step 2; Example 3, Steps 1-3; Example 4 | Colorless Oil |
| 142 | 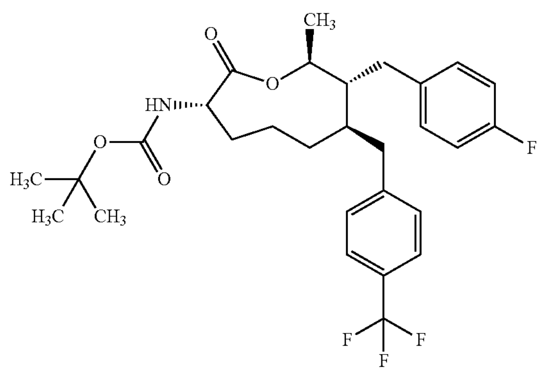 [SMILES: C[C@@H]1OC(=O)[C@@H](NC(=O)OC(C)(C)C)CCC[C@H](Cc2ccc(C(F)(F)F)cc2)[C@H]1Cc1ccc(F)cc1] | Example 1, Steps 1-3; Example 2, Steps 1a-c, Step 2; Example 3, Steps 1-3; Example 4 | Colorless Oil |
| 143 | 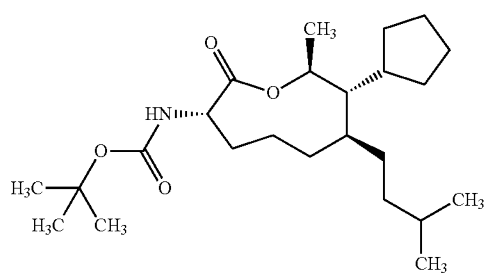 [SMILES: CC(C)CC[C@H]1CCC[C@H](NC(=O)OC(C)(C)C)C(=O)O[C@@H](C)[C@@H]1C1CCCC1] | Example 1, Steps 1-3; Example 2, Steps 1a-c, Step 2; Example 3, Steps 1-3; Example 4 | Colorless Oil |
| 144 | 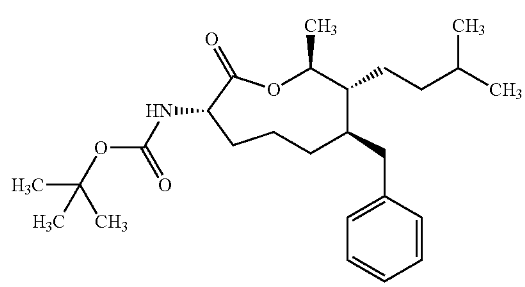 [SMILES: CC(C)CC[C@@H]1[C@@H](Cc2ccccc2)CCC[C@H](NC(=O)OC(C)(C)C)C(=O)O[C@H]1C] | Example 1, Steps 1-3; Example 2, Steps 1a-c, Step 2; Example 3, Steps 1-3; Example 4 | Colorless Oil |
| 145 | 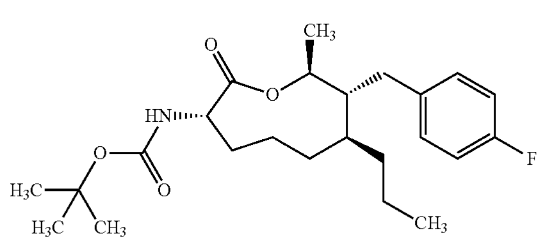 [SMILES: CCC[C@H]1CCC[C@H](NC(=O)OC(C)(C)C)C(=O)O[C@@H](C)[C@@H]1Cc1ccc(F)cc1] | Example 1, Steps 1-3; Example 2, Steps 1a-c, Step 2; Example 3, Steps 1-3; Example 4 | Colorless Oil |

TABLE 1-continued

Compound Structure and Appearance

| *Cmpd. No. | Structure | Prepared According to Example | Appearance |
|---|---|---|---|
| 146 | 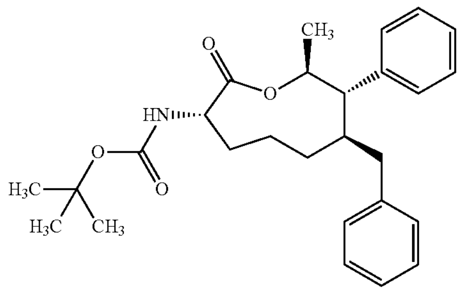 [SMILES: C[C@@H]1OC(=O)[C@@H](NC(=O)OC(C)(C)C)CCC[C@H](Cc2ccccc2)[C@H]1c1ccccc1] | Example 1, Steps 1-3; Example 2, Steps 1a-c, Step 2; Example 3, Steps 1-3; Example 4 | Colorless Oil |
| 147 | 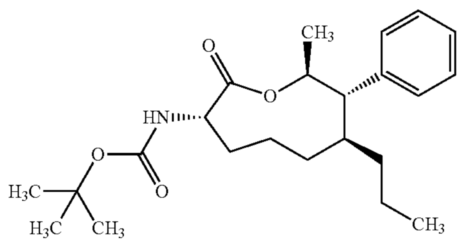 [SMILES: CCC[C@H]1CCC[C@H](NC(=O)OC(C)(C)C)C(=O)O[C@@H](C)[C@@H]1c1ccccc1] | Example 1, Steps 1-3; Example 2, Steps 1a-c, Step 2; Example 3, Steps 1-3; Example 4 | Colorless Oil |
| 148 | 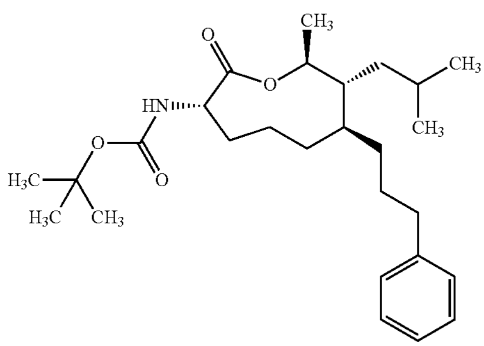 [SMILES: CC(C)C[C@@H]1[C@@H](CCCc2ccccc2)CCC[C@H](NC(=O)OC(C)(C)C)C(=O)O[C@H]1C] | Example 1, Steps 1-3; Example 2, Steps 1a-c, Step 2; Example 3, Steps 1-3; Example 4 | Colorless Oil |
| 149 | 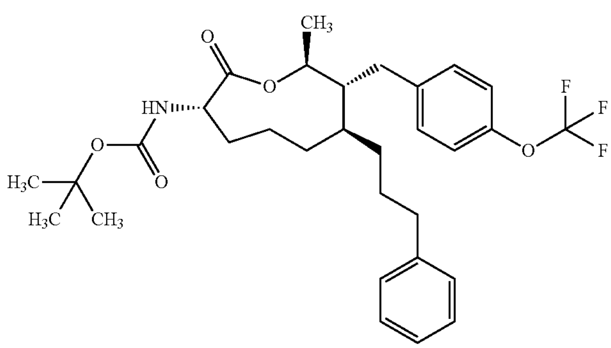 [SMILES: C[C@@H]1OC(=O)[C@@H](NC(=O)OC(C)(C)C)CCC[C@H](CCCc2ccccc2)[C@H]1Cc1ccc(OC(F)(F)F)cc1] | Example 1, Steps 1-3; Example 2, Steps 1a-c, Step 2; Example 3, Steps 1-3; Example 4 | Tacky White Solid |
| 150 | 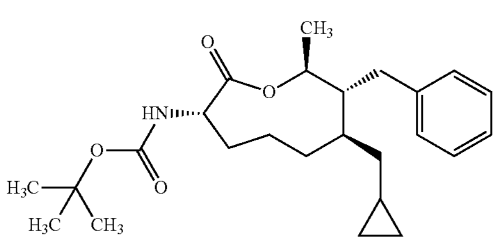 [SMILES: C[C@@H]1OC(=O)[C@@H](NC(=O)OC(C)(C)C)CCC[C@H](CC2CC2)[C@H]1Cc1ccccc1] | Example 1, Steps 1-3; Example 2, Steps 1a-c, Step 2; Example 3, Steps 1-3; Example 4 | Colorless Oil |

TABLE 1-continued

Compound Structure and Appearance

| *Cmpd. No. | Structure | Prepared According to Example | Appearance |
|---|---|---|---|
| 151 | 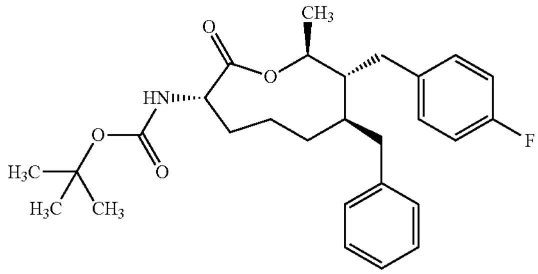 [SMILES: C[C@@H]1OC(=O)[C@@H](NC(=O)OC(C)(C)C)CCC[C@H](Cc2ccccc2)[C@H]1Cc1ccc(F)cc1] | Example 1, Steps 1-3; Example 2, Steps 1a-c, Step 2; Example 3, Steps 1-3; Example 4 | Colorless Oil |
| 152 | 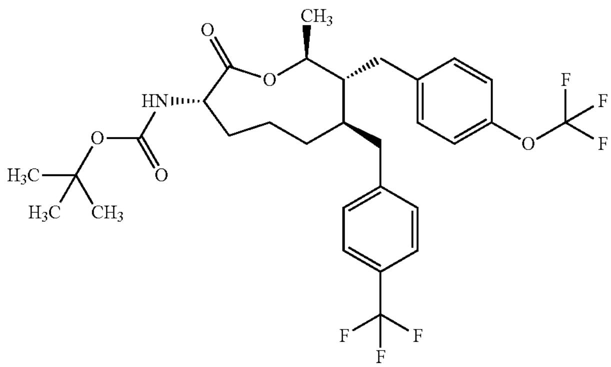 [SMILES: C[C@@H]1OC(=O)[C@@H](NC(=O)OC(C)(C)C)CCC[C@H](Cc2ccc(C(F)(F)F)cc2)[C@H]1Cc1ccc(OC(F)(F)F)cc1] | Example 1, Steps 1-3; Example 2, Steps 1a-c, Step 2; Example 3, Steps 1-3; Example 4 | Colorless Solid |
| 153 | 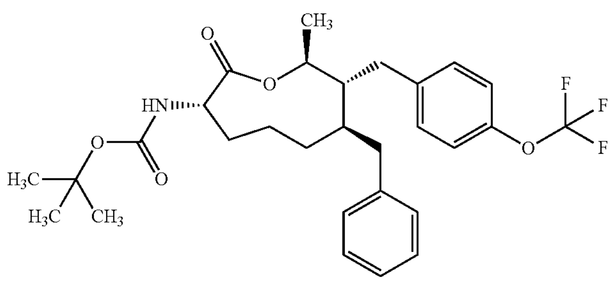 [SMILES: C[C@@H]1OC(=O)[C@@H](NC(=O)OC(C)(C)C)CCC[C@H](Cc2ccccc2)[C@H]1Cc1ccc(OC(F)(F)F)cc1] | Example 1, Steps 1-3; Example 2, Steps 1a-c, Step 2; Example 3, Steps 1-3; Example 4 | Sticky Colorless Solid |
| 154 | 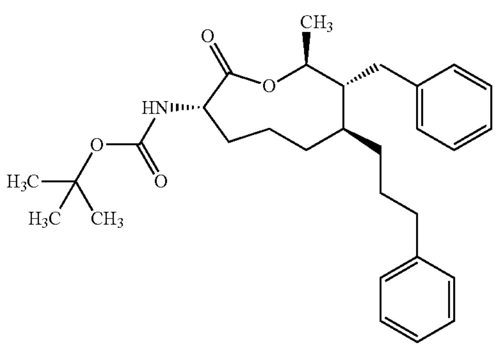 [SMILES: C[C@@H]1OC(=O)[C@@H](NC(=O)OC(C)(C)C)CCC[C@H](CCCc2ccccc2)[C@H]1Cc1ccccc1] | Example 1, Steps 1-3; Example 2, Steps 1a-c, Step 2; Example 3, Steps 1-3; Example 4 | Sticky Colorless Solid |

TABLE 2

Analytical Data

| *Cmpd. No. | MP (° C.) | IR (cm$^{-1}$) | MASS | NMR ($^1$H, $^{13}$C or $^{19}$F) |
|---|---|---|---|---|
| 1 | — | — | HRMS-FAB (m/z) | $^1$H NMR (CDCl$_3$) 8.60-8.43 (m, 1H), 8.31 (d, J = 5.4 Hz, 1H), 7.33-7.11 (m, 5H), 6.98 (d, J = |

TABLE 2-continued

Analytical Data

| *Cmpd. No. | MP (° C.) | IR (cm⁻¹) | MASS | NMR (¹H, ¹³C or ¹⁹F) |
|---|---|---|---|---|
| | | | [M + H]⁺ calcd for C₂₉H₃₉N₂O₆, 511.2811; found, 511.2805 | 5.5 Hz, 1H), 4.82 (dq, J = 9.6, 6.3 Hz, 1H), 4.56 (ddd, J = 11.0, 8.5, 7.3 Hz, 1H), 3.88 (s, 3H), 2.91-2.79 (m, 1H), 2.40 (s, 3H), 2.38-2.23 (m, 2H), 1.79 (ddt, J = 11.0, 8.0, 3.2 Hz, 1H), 1.69-1.11 (m, 11H), 1.35 (d, J = 6.3 Hz, 3H); 0.94 (t, J = 7.2 Hz, 3H), 0.79 (ddd, J = 13.5, 10.9, 7.1 Hz, 1H) <br> ¹³C NMR (CDCl₃) 172.46, 168.90, 162.39, 159.40, 146.71, 141.53, 141.18, 137.44, 128.73, 128.33, 125.86, 109.75, 75.36, 56.27, 51.15, 45.31, 42.60, 37.88, 33.40, 29.35, 27.82, 27.48, 23.51, 20.76, 19.66, 18.55, 14.04 |
| 2 | — | — | HRMS-FAB (m/z) [M + H]⁺ calcd for C₃₀H₄₁N₂O₇, 541.2921; found, 541.2916 | ¹H NMR (CDCl₃) 8.29 (d, J = 8.5 Hz, 1H), 8.27 (d, J = 5.4 Hz, 1H), 7.31-7.12 (m, 5H), 6.93 (d, J = 5.4 Hz, 1H), 5.74 (s, 2H), 4.83 (dq, J = 9.6, 6.3 Hz, 1H), 4.63-4.53 (m, 1H), 3.90 (s, 3H), 2.91-2.80 (m, 1H), 2.41-2.27 (m, 2H), 2.07 (s, 3H), 1.85-1.74 (m, 1H), 1.71-1.13 (m, 11H), 1.36 (d, J = 6.3 Hz, 1H), 0.94 (t, J = 7.2 Hz, 3H), 0.86-0.74 (m, 1H) <br> ¹³C NMR (CDCl₃) 172.58, 170.27, 162.96, 160.23, 145.76, 143.87, 142.61, 141.19, 128.73, 128.32, 125.86, 109.55, 89.53, 75.35, 56.18, 51.41, 45.32, 42.60, 37.88, 33.23, 29.36, 27.82, 27.48, 23.51, 20.89, 19.68, 18.59, 14.04 |
| 3 | — | — | HRMS-FAB (m/z) [M + H]⁺ calcd for C₃₁H₄₀F₃N₂O₇, 609.2806; found, 609.2801 | ¹H NMR (CDCl₃) 8.36-8.17 (m, 2H), 7.65-7.47 (m, 2H), 7.31-7.17 (m, 2H), 6.94 (d, J = 5.4 Hz, 1H), 5.74 (s, 2H), 4.83 (dq, J = 9.7, 6.3 Hz, 1H), 4.63-4.53 (m, 1H), 3.90 (s, 3H), 2.95-2.82 (m, 1H), 2.43 (dd, J = 13.8, 11.3 Hz, 1H), 2.33 (dt, J = 13.5, 6.8 Hz, 1H), 2.06 (s, 3H), 1.86-1.76 (m, 1H), 1.71-1.60 (m, 2H), 1.60-1.10 (m, 11H), 1.37 (d, J = 6.3 Hz, 3H), 0.94 (t, J = 7.1 Hz, 3H), 0.83 (ddd, J = 15.1, 8.2, 2.8 Hz, 1H) <br> ¹⁹F NMR (CDCl₃) −62.3 |
| 4 | — | — | HRMS-FAB (m/z) [M + H]⁺ calcd for C₃₀H₄₁N₂O₆, 525.2963; found, 525.2957 | ¹H NMR (CDCl₃) 8.55 (d, J = 8.6 Hz, 1H), 8.33 (d, J = 5.4 Hz, 1H), 7.36-7.15 (m, 5H), 6.99 (d, J = 5.4 Hz, 1H), 4.87 (dq, J = 9.6, 6.4 Hz, 1H), 4.54 (ddd, J = 10.9, 8.3, 7.1 Hz, 1H), 3.89 (s, 3H), 2.75 (dd, J = 15.4, 3.2 Hz, 1H), 2.56 (dd, J = 15.4, 7.7 Hz, 1H), 2.39 (s, 3H), 2.37-2.29 (m, 1H), 1.99-1.88 (m, 1H), 1.84-1.74 (m, 1H), 1.66-1.51 (m, 2H), 1.51-1.34 (m, 2H), 1.33-1.22 (m, 4H), 1.19 (d, J = 6.4 Hz, 3H), 1.06-0.89 (m, 2H), 0.84 (d, J = 6.6 Hz, 6H) <br> ¹³C NMR (CDCl₃) δ 172.49, 168.91, 162.37, 159.41, 146.71, 141.56, 141.00, 137.44, 128.83, 128.40, 125.97, 109.74, 76.20, 56.27, 51.32, 47.54, 42.28, 37.53, 36.77, 33.38, 29.33, 28.24, 27.87, 23.03, 22.32, 20.75, 18.55 |
| 5 | — | — | HRMS-FAB (m/z) [M + H]⁺ calcd for C₃₂H₃₇N₂O₆, 545.2653; found, 545.2648 | ¹H NMR (CDCl₃) δ 8.61-8.39 (m, 1H), 8.31 (d, J = 5.4 Hz, 1H), 7.38-7.05 (m, 10H), 6.97 (d, J = 5.5 Hz, 1H), 4.93 (dq, J = 9.7, 6.4 Hz, 1H), 4.57 (ddd, J = 10.9, 8.4, 7.1 Hz, 1H), 3.87 (s, 3H), 2.96 (td, J = 15.6, 3.3 Hz, 2H), 2.72 (dd, J = 15.6, 7.5 Hz, 1H), 2.48-2.39 (m, 1H), 2.39 (s, 3H), 2.30 (dt, J = 13.4, 6.8 Hz, 1H), 2.11 (dtd, J = 9.8, 7.1, 3.8 Hz, 1H), 1.81-1.38 (m, 4H), 1.27 (d, J = 6.3 Hz, 3H), 1.24-1.10 (m, 1H), 0.90-0.80 (m, 1H) <br> ¹³C NMR (CDCl₃) δ 172.38, 168.92, 162.41, 159.42, 146.72, 141.52, 140.77, 140.56, 137.46, 128.89, 128.71, 128.57, 128.33, 126.23, 125.94, 109.78, 76.00, 56.29, 51.23, 46.88, 44.26, 37.86, 37.33, 33.41, 27.46, 20.77, 20.73, 18.74 |
| 6 | — | — | HRMS-FAB (m/z) [M + H]⁺ calcd for C₃₃H₃₉N₂O₇, 575.2757; found, 575.2745 | ¹H NMR (CDCl₃) δ 8.29 (d, J = 8.1 Hz, 1H), 8.26 (d, J = 5.3 Hz, 1H), 7.39-7.04 (m, 10H), 6.93 (d, J = 5.4 Hz, 1H), 5.73 (s, 2H), 4.93 (dq, J = 9.7, 6.4 Hz, 1H), 4.58 (dt, J = 11.0, 7.5 Hz, 1H), 3.89 (s, 3H), 3.08-2.88 (m, 2H), 2.73 (dd, J = 15.6, 7.5 Hz, 1H), 2.43 (dd, J = 13.8, 11.6 Hz, 1H), 2.33 (dt, J = 13.5, 6.8 Hz, 1H), 2.12 (tdd, J = 10.0, 5.9, 3.0 Hz, 1H), 2.06 (s, 3H), 1.77-1.39 (m, 4H), 1.28 (d, J = 6.4 Hz, 3H), 1.24-1.09 (m, 1H), 0.89-0.81 (m, 1H) |

TABLE 2-continued

Analytical Data

| *Cmpd. No. | MP (° C.) | IR (cm⁻¹) | MASS | NMR ($^1$H, $^{13}$C or $^{19}$F) |
|---|---|---|---|---|
| | | | | $^{13}$C NMR (CDCl$_3$) δ 172.49, 170.27, 162.96, 160.23, 145.76, 143.88, 142.59, 140.77, 140.55, 128.89, 128.71, 128.56, 128.32, 126.22, 125.93, 109.56, 89.51, 75.97, 56.18, 51.48, 46.86, 44.25, 37.85, 37.32, 33.24, 27.45, 20.89, 20.74, 18.76 |
| 7 | — | — | HRMS-FAB (m/z) [M + H]$^+$ calcd for C$_{35}$H$_{43}$N$_2$O$_7$, 603.3070; found, 603.3067 | $^1$H NMR (CDCl$_3$) δ 8.36 (d, J = 8.1 Hz, 1H), 8.25 (d, J = 5.4 Hz, 1H), 7.35-7.08 (m, 10H), 6.92 (d, J = 5.4 Hz, 1H), 5.81-5.72 (m, 2H), 4.94 (dq, J = 9.7, 6.3 Hz, 1H), 4.58 (ddd, J = 11.0, 8.1, 7.1 Hz, 1H), 3.87 (s, 3H), 3.06-2.90 (m, 2H), 2.72 (dd, J = 15.6, 7.5 Hz, 1H), 2.53 (hept, J = 7.0 Hz, 1H), 2.44 (dd, J = 13.8, 11.6 Hz, 1H), 2.37-2.28 (m, 1H), 2.17-2.07 (m, 1H), 1.82-1.64 (m, 2H), 1.64-1.52 (m, 1H), 1.46 (tdd, J = 14.9, 8.9, 4.4 Hz, 1H), 1.28 (d, J = 6.4 Hz, 3H), 1.25-1.15 (m, 1H), 1.13 (d, J = 7.0 Hz, 6H), 0.90-0.78 (m, 1H) $^{13}$C NMR (CDCl$_3$) δ 176.23, 172.48, 162.94, 160.22, 145.62, 144.10, 142.24, 140.77, 140.57, 128.89, 128.71, 128.56, 128.32, 126.22, 125.93, 109.52, 89.87, 75.95, 56.14, 51.47, 46.87, 44.25, 37.85, 37.33, 33.86, 33.24, 27.45, 20.74, 18.77, 18.69 |
| 8 | — | — | HRMS-FAB (m/z) [M + H]$^+$ calcd for C$_{35}$H$_{43}$N$_2$O$_8$, 619.3019; found, 619.3018 | $^1$H NMR (CDCl$_3$) δ 8.31 (d, J = 8.1 Hz, 1H), 8.26 (d, J = 5.4 Hz, 1H), 7.35-7.07 (m, 10H), 6.93 (d, J = 5.4 Hz, 1H), 5.81 (s, 2H), 4.93 (dq, J = 9.7, 6.3 Hz, 1H), 4.57 (ddd, J = 11.0, 8.1, 7.1 Hz, 1H), 4.09 (s, 2H), 3.88 (s, 3H), 3.58 (q, J = 7.0 Hz, 2H), 3.03-2.89 (m, 2H), 2.73 (dd, J = 15.6, 7.5 Hz, 1H), 2.43 (dd, J = 13.8, 11.6 Hz, 1H), 2.37-2.27 (m, 1H), 2.16-2.06 (m, 1H), 1.79-1.38 (m, 4H), 1.28 (d, J = 6.4 Hz, 3H), 1.22 (t, J = 7.0 Hz, 3H), 1.19-1.11 (m, 1H), 0.89-0.81 (m, 1H) $^{13}$C NMR (CDCl$_3$) δ 172.46, 170.05, 162.91, 160.15, 145.80, 143.85, 142.42, 140.76, 140.55, 128.88, 128.70, 128.56, 128.32, 126.22, 125.93, 109.67, 89.54, 75.99, 67.80, 67.18, 56.22, 51.47, 46.87, 44.23, 37.86, 37.32, 33.24, 27.46, 20.75, 18.76, 15.02 |
| 9 | — | — | HRMS-FAB (m/z) [M + H]$^+$ calcd for C$_{30}$H$_{39}$N$_2$O$_6$, 523.2808; found, 523.2797 | $^1$H NMR (CDCl$_3$) δ 8.55 (s, 1H), 8.32 (d, J = 5.9 Hz, 1H), 7.32-7.15 (m, 5H), 6.99 (d, J = 5.4 Hz, 1H), 4.96 (dq, J = 8.5, 6.3 Hz, 1H), 4.56 (ddd, J = 11.1, 8.3, 6.6 Hz, 1H), 3.89 (s, 3H), 2.85 (dd, J = 14.4, 3.6 Hz, 1H), 2.61 (dd, J = 14.2, 11.2 Hz, 1H), 2.40 (s, 3H), 2.30-2.19 (m, 1H), 2.12-1.98 (m, 2H), 1.89-1.41 (m, 10H), 1.39 (d, J = 6.3 Hz, 3H), 1.37-1.14 (m, 3H), 0.89-0.79 (m, 1H) $^{13}$C NMR (CDCl$_3$) δ 172.46, 168.92, 162.37, 159.40, 146.69, 141.54, 141.08, 137.44, 128.64, 128.28, 125.87, 109.74, 74.67, 56.28, 51.72, 48.73, 42.58, 40.11, 39.46, 33.56, 29.50, 28.75, 27.75, 25.22, 24.48, 21.46, 20.77, 19.59 |
| 10 | — | — | HRMS-FAB (m/z) [M + H]$^+$ calcd for C$_{31}$H$_{41}$N$_2$O$_7$, 553.2914; found, 553.2904 | $^1$H NMR (CDCl$_3$) δ 8.33 (d, J = 8.0 Hz, 1H), 8.27 (d, J = 5.4 Hz, 1H), 7.32-7.17 (m, 5H), 6.94 (d, J = 5.4 Hz, 1H), 5.74 (s, 2H), 4.96 (dq, J = 8.7, 6.3 Hz, 1H), 4.58 (ddd, J = 11.2, 8.0, 6.6 Hz, 1H), 3.90 (s, 3H), 2.86 (dd, J = 14.2, 3.8 Hz, 1H), 2.62 (dd, J = 14.2, 11.2 Hz, 1H), 2.27 (dt, J = 13.4, 6.8 Hz, 1H), 2.13-1.97 (m, 2H), 2.07 (s, 3H), 1.85-1.45 (m, 10H), 1.40 (d, J = 6.2 Hz, 3H), 1.39-1.15 (m, 3H), 0.92-0.78 (m, 1H) $^{13}$C NMR (CDCl$_3$) δ 172.56, 170.27, 162.95, 160.23, 145.76, 143.86, 142.63, 141.08, 128.64, 128.28, 125.87, 109.55, 89.53, 74.66, 56.18, 51.95, 48.67, 42.56, 40.11, 39.45, 33.37, 29.48, 28.71, 27.76, 25.22, 24.46, 21.45, 20.89, 19.61 |
| 11 | — | — | HRMS-FAB (m/z) [M + H]$^+$ calcd for C$_{33}$H$_{45}$N$_2$O$_7$, 581.3227; found, | $^1$H NMR (CDCl$_3$) δ 8.39 (d, J = 8.1 Hz, 1H), 8.26 (d, J = 5.3 Hz, 1H), 7.37-7.13 (m, 5H), 6.93 (d, J = 5.4 Hz, 1H), 5.86-5.67 (m, 2H), 4.97 (dq, J = 8.5, 6.3 Hz, 1H), 4.57 (ddd, J = 11.1, 8.1, 6.6 Hz, 1H), 3.88 (s, 3H), 2.92-2.80 (m, 1H), 2.62 (dd, J = 14.2, 11.3 Hz, 1H), 2.60-2.46 (m, 1H), 2.27 (dt, J = 13.4, 6.8 Hz, 1H), |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | 581.3215 | 2.13-1.98 (m, 2H), 1.83-1.45 (m, 10H), 1.40 (d, J = 6.3 Hz, 3H), 1.38-1.20 (m, 3H), 1.14 (d, J = 7.0 Hz, 6H), 0.91-0.81 (m, 1H) $^{13}$C NMR (CDCl$_3$) δ 176.24, 172.56, 162.92, 160.22, 145.63, 144.10, 142.26, 141.09, 128.64, 128.28, 125.87, 109.49, 89.90, 74.64, 56.13, 51.94, 48.66, 42.56, 40.10, 39.45, 33.86, 33.37, 29.48, 28.71, 27.76, 25.22, 24.46, 21.45, 19.62, 18.69 |
| 12 | — | — | HRMS-FAB (m/z) [M + H]$^+$ calcd for C$_{30}$H$_{40}$ClN$_2$O$_7$, 575.2524; found, 575.2523 | $^1$H NMR (CDCl$_3$) δ 8.30 (d, J = 8.6 Hz, 1H), 8.27 (d, J = 5.4 Hz, 1H), 7.27-7.20 (m, 2H), 7.15-7.03 (m, 2H), 6.94 (d, J = 5.4 Hz, 1H), 5.74 (s, 2H), 4.75 (dq, J = 9.4, 6.4 Hz, 1H), 4.58 (ddd, J = 11.0, 8.1, 7.1 Hz, 1H), 3.90 (s, 3H), 2.93-2.77 (m, 1H), 2.42-2.25 (m, 2H), 2.07 (s, 3H), 1.77-1.49 (m, 5H), 1.44-1.32 (m, 2H), 1.37 (d, J = 6.3 Hz, 3H), 1.24-1.06 (m, 2H), 0.98 (d, J = 6.8 Hz, 3H), 0.96 (d, J = 6.7 Hz, 3H), 0.86-0.77 (m, 1H) $^{13}$C NMR (CDCl$_3$) δ 172.53, 170.26, 162.96, 160.22, 145.75, 143.87, 142.55, 139.52, 131.56, 130.01, 128.43, 109.57, 89.50, 76.69, 56.18, 51.39, 45.92, 43.72, 41.55, 36.81, 33.22, 27.56, 27.28, 24.09, 21.96, 20.88, 19.72, 18.53 |
| 13 | — | — | HRMS-FAB (m/z) [M + H]$^+$ calcd for C$_{29}$H$_{38}$ClN$_2$O$_6$, 545.2418; found, 545.2417 | $^1$H NMR (CDCl$_3$) δ 8.51 (d, J = 8.5 Hz, 1H), 8.31 (d, J = 5.4 Hz, 1H), 7.26-7.20 (m, 2H), 7.13-7.03 (m, 2H), 6.99 (d, J = 5.5 Hz, 1H), 4.74 (dq, J = 9.2, 6.3 Hz, 1H), 4.56 (ddd, J = 10.9, 8.4, 7.1 Hz, 1H), 3.88 (s, 3H), 2.92-2.77 (m, 1H), 2.40 (s, 3H), 2.35-2.24 (m, 2H), 1.80-1.46 (m, 5H), 1.43-1.28 (m, 2H), 1.36 (d, J = 6.5 Hz, 3H), 1.22-1.05 (m, 2H), 0.98 (d, J = 6.7 Hz, 3H), 0.95 (d, J = 6.7 Hz, 3H), 0.85-0.71 (m, 1H) $^{13}$C NMR (CDCl$_3$) δ 172.42, 168.89, 162.39, 159.40, 146.71, 141.48, 139.52, 137.43, 131.57, 130.01, 128.43, 109.77, 76.70, 56.27, 51.13, 45.92, 43.71, 41.54, 36.80, 33.39, 27.56, 27.29, 24.09, 21.97, 20.76, 19.70, 18.49 |
| 14 | 60-64 | — | ESIMS m/z 541 [M + H]$^+$ | $^1$H NMR (CDCl$_3$) δ 8.29 (d, J = 8.1 Hz, 1H), 8.26 (d, J = 5.4 Hz, 1H), 7.32-7.25 (m, 2H), 7.22-7.13 (m, 3H), 6.93 (d, J = 5.4 Hz, 1H), 5.74 (s, 2H), 4.76 (dq, J = 8.9, 6.3 Hz, 1H), 4.58 (dt, J = 11.0, 7.5 Hz, 1H), 3.90 (s, 3H), 2.89 (d, J = 14.0 Hz, 1H), 2.37-2.27 (m, 2H), 2.11-2.02 (m, 3H), 1.80-1.48 (m, 5H), 1.47-1.33 (m, 5H), 1.24-1.09 (m, 2H), 0.98 (d, J = 6.5 Hz, 3H), 0.96 (d, J = 6.6 Hz, 3H), 0.88-0.77 (m, 1H) $^{13}$C NMR (CDCl$_3$) δ 172.57, 170.24, 162.92, 160.20, 145.71, 143.86, 142.59, 141.08, 128.67, 128.28, 125.84, 109.49, 89.52, 76.78, 56.14, 51.40, 45.96, 43.73, 41.54, 37.40, 33.29, 27.57, 27.31, 24.10, 21.94, 20.86, 19.72, 18.54 |
| 15 | 89-91 | (Neat) 3383, 2940, 1739, 1676, 1504, 1370, 1203 | HRMS-ESI (m/z) [M]$^+$ calcd for C$_{34}$H$_{40}$N$_2$O$_7$, 588.2836; found, 588.2839 | $^1$H NMR (CDCl$_3$) δ 8.30 (d, J = 8.6 Hz, 1H), 8.28 (d, J = 5.4 Hz, 1H), 7.35-7.26 (m, 4H), 7.24-7.13 (m, 6H), 6.94 (d, J = 5.4 Hz, 1H), 5.75 (s, 2H), 4.98-4.88 (m, 1H), 4.65-4.56 (m, 1H), 3.91 (s, 3H), 2.90-2.72 (m, 2H), 2.61-2.48 (m, 1H), 2.42-2.28 (m, 2H), 2.07 (s, 3H), 1.96-1.72 (m, 4H), 1.72-1.47 (m, 3H), 1.48 (d, J = 6.3 Hz, 3H), 1.28-1.15 (m, 1H), 0.91-0.77 (m, 1H) |
| 16 | — | (Neat) 3380, 2940, 1738, 1677, 1504, 1210 | HRMS-ESI (m/z) [M]$^+$ calcd for C$_{36}$H$_{44}$N$_2$O$_8$, 632.3098; found, 632.3097 | $^1$H NMR (CDCl$_3$) δ 8.31 (d, J = 8.2 Hz, 1H), 8.27 (d, J = 5.4 Hz, 1H), 7.34-7.26 (m, 4H), 7.25-7.13 (m, 6H), 6.94 (d, J = 5.4 Hz, 1H), 5.83 (s, 2H), 4.98-4.87 (m, 1H), 4.64-4.53 (m, 1H), 4.10 (s, 2H), 3.90 (s, 3H), 3.59 (q, J = 7.0 Hz, 2H), 2.89-2.72 (m, 2H), 2.60-2.48 (m, 1H), 2.42-2.27 (m, 2H), 1.96-1.72 (m, 4H), 1.71-1.48 (m, 3H), 1.48 (d, J = 6.3 Hz, 3H), 1.27-1.16 (m, 1H), 1.23 (t, J = 7.0 Hz, 3H), 0.90-0.79 (m, 1H) |
| 17 | 79-81 | (Neat) 3382, | HRMS-ESI (m/z) | $^1$H NMR (CDCl$_3$) δ 8.36 (d, J = 8.2 Hz, 1H), 8.27 (d, J = 5.3 Hz, 1H), 7.35-7.26 (m, 4H), |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | 2939, 1741, 1676, 1504, 1315, 1210 | [M]$^+$ calcd for C$_{36}$H$_{44}$N$_2$O$_7$, 616.3149; found, 616.3159 | 7.24-7.12 (m, 6H), 6.93 (d, J = 5.4 Hz, 1H), 5.81-5.74 (m, 2H), 4.98-4.88 (m, 1H), 4.65-4.55 (m, 1H), 3.89 (s, 3H), 2.92-2.70 (m, 2H), 2.62-2.48 (m, 2H), 2.42-2.28 (m, 2H), 1.96-1.72 (m, 4H), 1.71-1.47 (m, 3H), 1.48 (d, J = 6.3 Hz, 3H), 1.30-1.17 (m, 1H), 1.15 (d, J = 7.0 Hz, 6H), 0.91-0.79 (m, 1H) |
| 18 | — | (Neat) 3378, 2940, 1737, 1677, 1508, 1369, 1200 | HRMS-ESI (m/z) [M]$^+$ calcd for C$_{33}$H$_{38}$N$_2$O$_6$, 558.2730; found, 558.2732 | $^1$H NMR (CDCl$_3$) δ 8.51 (d, J = 6.8 Hz, 1H), 8.33 (d, J = 5.4 Hz, 1H), 7.34-7.26 (m, 4H), 7.24-7.12 (m, 6H), 6.99 (d, J = 5.5 Hz, 1H), 4.98-4.87 (m, 1H), 4.64-4.53 (m, 1H), 3.90 (s, 3H), 2.89-2.71 (m, 2H), 2.59-2.48 (m, 1H), 2.40 (s, 3H), 2.40-2.25 (m, 2H), 1.95-1.72 (m, 4H), 1.70-1.48 (m, 3H), 1.46 (d, J = 6.3 Hz, 3H), 1.28-1.14 (m, 1H), 0.91-0.77 (m, 1H) |
| 19 | 98-100 | (Neat) 3380, 2938, 2249, 1737, 1675, 1495, 1202 | HRMS-ESI (m/z) [M]$^+$ calcd for C$_{33}$H$_{37}$ClN$_2$O$_7$, 608.2289; found, 608.2293 | $^1$H NMR (CDCl$_3$) δ 8.29 (d, J = 8.4 Hz, 1H), 8.27 (d, J = 5.4 Hz, 1H), 7.36-7.30 (m, 2H), 7.29-7.19 (m, 5H), 7.03-6.98 (m, 2H), 6.93 (d, J = 5.4 Hz, 1H), 5.73 (s, 2H), 4.99-4.87 (m, 1H), 4.64-4.53 (m, 1H), 3.90 (s, 3H), 2.95 (dd, J = 15.6, 3.3 Hz, 1H), 2.91-2.83 (m, 1H), 2.74 (dd, J = 15.7, 7.5 Hz, 1H), 2.46-2.28 (m, 2H), 2.16-2.05 (m, 1H), 2.06 (s, 3H), 1.79-1.62 (m, 2H), 1.59-1.35 (m, 2H), 1.29 (d, J = 6.4 Hz, 3H), 1.27-1.13 (m, 1H), 0.90-0.79 (m, 1H) |
| 20 | — | (Neat) 3380, 2938, 2249, 1736, 1675, 1505, 1207 | HRMS-ESI (m/z) [M]$^+$ calcd for C$_{35}$H$_{41}$ClN$_2$O$_8$, 652.2551; found, 652.2550 | $^1$H NMR (CDCl$_3$) δ 8.31 (d, J = 8.1 Hz, 1H), 8.27 (d, J = 5.4 Hz, 1H), 7.35-7.30 (m, 2H), 7.28-7.18 (m, 5H), 7.04-6.98 (m, 2H), 6.93 (d, J = 5.4 Hz, 1H), 5.81 (s, 2H), 4.99-4.88 (m, 1H), 4.61-4.52 (m, 1H), 4.09 (s, 2H), 3.90 (s, 3H), 3.58 (q, J = 7.0 Hz, 2H), 2.95 (dd, J = 15.6, 3.3 Hz, 1H), 2.92-2.83 (m, 1H), 2.74 (dd, J = 15.6, 7.4 Hz, 1H), 2.46-2.26 (m, 2H), 2.16-2.05 (m, 1H), 1.79-1.35 (m, 4H), 1.29 (d, J = 6.4 Hz, 3H), 1.22 (t, J = 7.0 Hz, 3H), 1.24-1.13 (m, 1H), 0.90-0.78 (m, 1H) |
| 21 | — | (Neat) 3377, 2939, 1736, 1675, 1508, 1370, 1199 | HRMS-ESI (m/z) [M]$^+$ calcd for C$_{32}$H$_{35}$ClN$_2$O$_6$, 578.2184; found, 578.2184 | $^1$H NMR (CDCl$_3$) δ 8.51 (d, J = 8.4 Hz, 1H), 8.33 (d, J = 5.4 Hz, 1H), 7.35-7.29 (m, 2H), 7.28-7.19 (m, 5H), 7.03-6.96 (m, 3H), 4.99-4.87 (m, 1H), 4.62-4.51 (m, 1H), 3.90 (s, 3H), 2.94 (dd, J = 15.6, 3.3 Hz, 1H), 2.91-2.82 (m, 1H), 2.73 (dd, J = 15.6, 7.4 Hz, 1H), 2.39 (s, 3H), 2.45-2.34 (m, 1H), 2.35-2.25 (m, 1H), 2.14-2.04 (m, 1H), 1.77-1.35 (m, 4H), 1.28 (d, J = 6.4 Hz, 3H), 1.23-1.12 (m, 1H), 0.89-0.79 (m, 1H) |
| 22 | — | — | HRMS-FAB (m/z) [M + H]$^+$ calcd for C$_{30}$H$_{38}$F$_3$N$_2$O$_6$, 579.2682; found, 579.2669 | $^1$H NMR (CDCl$_3$) δ 8.51 (d, J = 8.4 Hz, 1H), 8.32 (d, J = 5.4 Hz, 1H), 7.58-7.48 (m, 2H), 7.36-7.21 (m, 2H), 6.99 (d, J = 5.5 Hz, 1H), 4.76 (dq, J = 9.1, 6.3 Hz, 1H), 4.57 (ddd, J = 11.0, 8.3, 7.1 Hz, 1H), 3.89 (s, 3H), 2.92 (d, J = 13.7 Hz, 1H), 2.43-2.36 (m, 1H), 2.40 (s, 3H), 2.30 (dt, J = 13.5, 6.9 Hz, 1H), 1.78-1.48 (m, 5H), 1.44-1.30 (m, 2H), 1.37 (d, J = 6.4 Hz, 3H), 1.24-1.07 (m, 2H), 0.99 (d, J = 6.5 Hz, 3H), 0.96 (d, J = 6.7 Hz, 3H), 0.90-0.81 (m, 1H) $^{19}$F NMR (CDCl$_3$) δ −62.77 |
| 23 | — | — | HRMS-FAB (m/z) [M + H]$^+$ calcd for C$_{31}$H$_{40}$F$_3$N$_2$O$_7$, 609.2787; found, 609.2774 | $^1$H NMR (CDCl$_3$) δ 8.30 (d, J = 8.1 Hz, 1H), 8.27 (d, J = 5.3 Hz, 1H), 7.54 (dd, J = 8.2, 1.0 Hz, 2H), 7.31-7.24 (m, 2H), 6.94 (d, J = 5.4 Hz, 1H), 5.74 (s, 2H), 4.77 (dq, J = 9.0, 6.3 Hz, 1H), 4.66-4.52 (m, 1H), 3.90 (s, 3H), 3.01-2.85 (m, 1H), 2.41 (dd, J = 13.8, 10.9 Hz, 1H), 2.33 (dt, J = 13.5, 6.8 Hz, 1H), 2.07 (s, 3H), 1.79-1.53 (m, 5H), 1.45-1.33 (m, 2H), 1.38 (d, J = 6.4 Hz, 3H), 1.23-1.08 (m, 2H), 0.99 (d, J = 6.6 Hz, 3H), 0.97 (d, J = 6.6 Hz, 3H), 0.91-0.81 (m, 1H) $^{19}$F NMR (CDCl$_3$) δ −62.28 |
| 24 | — | — | HRMS-FAB (m/z) [M + H]$^+$ calcd for C$_{33}$H$_{44}$F$_3$N$_2$O$_7$, | $^1$H NMR (CDCl$_3$) δ 8.36 (d, J = 8.1 Hz, 1H), 8.26 (d, J = 5.4 Hz, 1H), 7.59-7.49 (m, 2H), 7.34-7.23 (m, 2H), 6.94 (d, J = 5.4 Hz, 1H), 5.87-5.73 (m, 2H), 4.77 (dq, J = 8.8, 6.3 Hz, 1H), 4.59 (ddd, J = 11.0, 8.1, 7.1 Hz, 1H), 3.88 |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | 637.3100; found, 637.3089 | (s, 3H), 3.00-2.88 (m, 1H), 2.55 (hept, J = 7.0 Hz, 1H), 2.41 (dd, J = 13.8, 10.9 Hz, 1H), 2.37-2.28 (m, 1H), 1.80-1.47 (m, 5H), 1.45-1.17 (m, 4H), 1.14 (d, J = 7.0 Hz, 6H), 0.99 (d, J = 6.5 Hz, 3H), 0.97 (d, J = 6.7 Hz, 3H), 0.91-0.82 (m, 1H) $^{19}$F NMR (CDCl$_3$) δ −62.28 |
| 25 | — | — | HRMS-FAB (m/z) [M + H]$^+$ calcd for C$_{33}$H$_{36}$F$_3$N$_2$O$_6$, 613.2525; found, 613.2517 | $^1$H NMR (CDCl$_3$) δ 8.51 (d, J = 8.4 Hz, 1H), 8.32 (d, J = 5.4 Hz, 1H), 7.55-7.12 (m, 9H), 6.99 (d, J = 5.5 Hz, 1H), 4.94 (dq, J = 9.7, 6.3 Hz, 1H), 4.57 (ddd, J = 10.9, 8.4, 7.1 Hz, 1H), 3.89 (s, 3H), 2.94 (ddd, J = 12.2, 9.7, 3.2 Hz, 2H), 2.76 (dd, J = 15.6, 7.3 Hz, 1H), 2.48 (dd, J = 13.9, 11.6 Hz, 1H), 2.39 (s, 3H), 2.31 (dt, J = 13.5, 7.0 Hz, 1H), 2.12 (tdd, J = 9.9, 7.2, 3.5 Hz, 1H), 1.83-1.74 (m, 1H), 1.71-1.63 (m, 1H), 1.57-1.47 (m, 1H), 1.43-1.34 (m, 1H), 1.30 (d, J = 6.4 Hz, 3H), 1.23-1.13 (m, 1H), 0.89-0.82 (m, 1H) $^{19}$F NMR (CDCl$_3$) δ −62.29 |
| 26 | — | — | HRMS-FAB (m/z) [M + H]$^+$ calcd for C$_{34}$H$_{38}$F$_3$N$_2$O$_7$, 643.2631; found, 643.2622 | $^1$H NMR (CDCl$_3$) δ 8.30 (d, J = 8.1 Hz, 1H), 8.27 (d, J = 5.4 Hz, 1H), 7.55-7.12 (m, 9H), 6.94 (d, J = 5.4 Hz, 1H), 5.74 (s, 2H), 4.95 (dq, J = 9.6, 6.3 Hz, 1H), 4.59 (ddd, J = 11.0, 8.1, 7.0 Hz, 1H), 3.90 (s, 3H), 3.05-2.86 (m, 2H), 2.77 (dd, J = 15.6, 7.3 Hz, 1H), 2.49 (dd, J = 13.8, 11.7 Hz, 1H), 2.34 (dt, J = 13.5, 6.6 Hz, 1H), 2.17-2.09 (m, 1H), 2.06 (s, 3H), 1.83-1.75 (m, 1H), 1.74-1.66 (m, 1H), 1.60-1.48 (m, 1H), 1.44-1.35 (m, 1H), 1.31 (d, J = 6.4 Hz, 3H), 1.24-1.13 (m, 1H), 0.88-0.83 (m, 1H) $^{19}$F NMR (CDCl$_3$) δ −62.29 |
| 27 | — | — | HRMS-FAB (m/z) [M + H]$^+$ calcd for C$_{36}$H$_{42}$F$_3$N$_2$O$_7$, 671.2944; found, 671.2936 | $^1$H NMR (CDCl$_3$) δ 8.36 (d, J = 8.1 Hz, 1H), 8.26 (d, J = 5.3 Hz, 1H), 7.55-7.14 (m, 9H), 6.93 (d, J = 5.4 Hz, 1H), 5.83-5.72 (m, 2H), 4.95 (dq, J = 9.6, 6.3 Hz, 1H), 4.59 (ddd, J = 11.0, 8.2, 7.1 Hz, 1H), 3.88 (s, 3H), 3.04-2.86 (m, 2H), 2.77 (dd, J = 15.6, 7.3 Hz, 1H), 2.62-2.44 (m, 2H), 2.33 (dt, J = 13.5, 6.9 Hz, 1H), 2.17-2.08 (m, 1H), 1.86-1.75 (m, 1H), 1.74-1.66 (m, 1H), 1.61-1.48 (m, 1H), 1.46-1.33 (m, 1H), 1.31 (d, J = 6.4 Hz, 3H), 1.28-1.20 (m, 1H), 1.14 (d, J = 7.0 Hz, 6H), 0.89-0.83 (m, 1H) $^{19}$F NMR (CDCl$_3$) δ −62.29 |
| 28 | — | — | HRMS-FAB (m/z) [M + H]$^+$ calcd for C$_{30}$H$_{38}$ClN$_2$O$_6$, 557.2418; found, 557.2416 | $^1$H NMR (CDCl$_3$) δ 8.70-8.49 (m, 1H), 8.32 (d, J = 5.4 Hz, 1H), 7.26-7.18 (m, 2H), 7.16-7.07 (m, 2H), 6.99 (d, J = 5.4 Hz, 1H), 4.96 (dq, J = 8.4, 6.3 Hz, 1H), 4.55 (ddd, J = 11.1, 8.3, 6.6 Hz, 1H), 3.89 (s, 3H), 2.86-2.72 (m, 1H), 2.59 (dd, J = 14.3, 11.2 Hz, 1H), 2.40 (s, 3H), 2.25 (dt, J = 13.5, 6.9 Hz, 1H), 2.11-1.92 (m, 2H), 1.86-1.80 (m, 1H), 1.75-1.49 (m, 8H), 1.38 (d, J = 6.3 Hz, 3H), 1.36-1.15 (m, 4H), 0.90-0.83 (m, 1H) $^{13}$C NMR (CDCl$_3$) δ 172.39, 168.90, 162.39, 159.41, 146.71, 141.51, 139.51, 137.44, 131.53, 129.95, 128.40, 109.76, 74.53, 56.28, 51.68, 48.82, 42.59, 40.08, 38.82, 33.52, 29.57, 28.81, 27.63, 25.18, 24.46, 21.48, 20.76, 19.54 |
| 29 | — | — | HRMS-FAB (m/z) [M + H]$^+$ calcd for C$_{31}$H$_{40}$ClN$_2$O$_7$, 587.2524; found, 587.2518 | $^1$H NMR (CDCl$_3$) δ 8.33 (d, J = 8.0 Hz, 1H), 8.27 (d, J = 5.4 Hz, 1H), 7.26-7.22 (m, 2H), 7.16-7.09 (m, 2H), 6.94 (d, J = 5.4 Hz, 1H), 5.74 (s, 2H), 4.97 (dq, J = 8.5, 6.3 Hz, 1H), 4.57 (ddd, J = 11.1, 8.0, 6.6 Hz, 1H), 3.90 (s, 3H), 2.81 (dd, J = 14.3, 3.8 Hz, 1H), 2.61 (dd, J = 14.2, 11.2 Hz, 1H), 2.27 (dt, J = 13.4, 6.8 Hz, 1H), 2.07 (s, 3H), 2.09-1.93 (m, 2H), 1.86-1.78 (m, 1H), 1.77-1.50 (m, 8H), 1.39 (d, J = 6.3 Hz, 3H), 1.37-1.15 (m, 4H), 0.88-0.82 (m, 1H) $^{13}$C NMR (CDCl$_3$) δ 172.50, 170.26, 162.96, 160.23, 145.76, 143.87, 142.59, 139.52, 131.52, 129.96, 128.40, 109.55, 89.52, 74.53, 56.18, |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| 30 | — | — | HRMS-FAB (m/z) [M + H]$^+$ calcd for C$_{33}$H$_{44}$ClN$_2$O$_7$, 615.2837; found, 615.2819 | 51.91, 48.76, 42.57, 40.08, 38.81, 33.33, 29.55, 28.76, 27.64, 25.18, 24.44, 21.47, 20.88, 19.57<br>$^1$H NMR (CDCl$_3$) δ 8.39 (d, J = 8.0 Hz, 1H), 8.26 (d, J = 5.3 Hz, 1H), 7.27-7.19 (m, 2H), 7.16-7.06 (m, 2H), 6.93 (d, J = 5.4 Hz, 1H), 5.89-5.65 (m, 2H), 4.97 (dq, J = 8.5, 6.3 Hz, 1H), 4.57 (ddd, J = 11.1, 8.0, 6.5 Hz, 1H), 3.88 (s, 3H), 2.81 (dd, J = 14.4, 3.8 Hz, 1H), 2.67-2.48 (m, 2H), 2.36-2.21 (m, 1H), 2.11-1.94 (m, 2H), 1.85-1.80 (m, 1H), 1.76-1.53 (m, 8H), 1.39 (d, J = 6.3 Hz, 3H), 1.35-1.23 (m, 4H), 1.14 (d, J = 7.0 Hz, 6H), 0.88-0.82 (m, 1H)<br>$^{13}$C NMR (CDCl$_3$) δ 176.23, 172.50, 162.93, 160.22, 145.62, 144.10, 142.24, 139.52, 131.52, 129.95, 128.40, 109.49, 89.88, 74.51, 56.12, 51.91, 48.78, 42.58, 40.08, 38.81, 33.85, 33.34, 29.55, 28.77, 27.64, 25.18, 24.44, 21.48, 19.57, 18.68 |
| 31 | — | — | HRMS-FAB (m/z) [M + H]$^+$ calcd for C$_{33}$H$_{44}$ClN$_2$O$_8$, 631.2786; found, 631.2786 | $^1$H NMR (CDCl$_3$) δ 8.35 (d, J = 8.0 Hz, 1H), 8.27 (d, J = 5.3 Hz, 1H), 7.27-7.20 (m, 2H), 7.16-7.08 (m, 2H), 6.94 (d, J = 5.4 Hz, 1H), 5.82 (s, 2H), 4.97 (dq, J = 8.5, 6.4 Hz, 1H), 4.56 (ddd, J = 11.1, 8.0, 6.6 Hz, 1H), 4.10 (s, 2H), 3.90 (s, 3H), 3.59 (q, J = 7.0 Hz, 2H), 2.81 (dd, J = 14.2, 3.8 Hz, 1H), 2.61 (dd, J = 14.2, 11.1 Hz, 1H), 2.26 (dt, J = 13.4, 6.8 Hz, 1H), 2.11-1.92 (m, 2H), 1.85-1.79 (m, 1H), 1.77-1.52 (m, 8H), 1.39 (d, J = 6.3 Hz, 3H), 1.37-1.14 (m, 4H), 1.23 (t, J = 7.0 Hz, 1H), 0.91-0.81 (m, 1H)<br>$^{13}$C NMR (CDCl$_3$) δ 172.47, 170.04, 162.90, 160.15, 145.81, 143.83, 142.42, 139.51, 131.52, 129.95, 128.40, 109.66, 89.54, 74.53, 67.79, 67.17, 56.21, 51.91, 48.79, 42.57, 40.07, 38.82, 33.33, 29.55, 28.78, 27.66, 25.18, 24.44, 21.49, 19.57, 15.01 |
| 32 | — | — | ESIMS m/z 617 [M + H]$^+$ | $^1$H NMR (CDCl$_3$) δ 8.33 (d, J = 8.1 Hz, 1H), 8.29 (d, J = 5.4 Hz, 1H), 7.32-7.24 (m, 4H), 7.18 (t, J = 6.7 Hz, 4H), 7.10 (d, J = 8.3 Hz, 2H), 6.94 (d, J = 5.4 Hz, 1H), 5.75 (s, 2H), 4.88 (dt, J = 12.6, 6.3 Hz, 1H), 4.57 (dt, J = 10.8, 7.5 Hz, 1H), 3.91 (s, 3H), 2.62 (ddt, J = 22.4, 15.1, 7.1 Hz, 3H), 2.43 (ddd, J = 13.7, 11.4, 5.9 Hz, 1H), 2.35 (dt, J = 13.6, 6.5 Hz, 1H), 2.07 (s, 3H), 1.90-1.19 (m, 12H), 1.42 (d, J = 6.3 Hz, 3H) 0.94 (dd, J = 14.9, 7.1 Hz, 1H)<br>$^{13}$C NMR (CDCl$_3$) δ 172.68, 170.30, 162.99, 160.25, 145.77, 143.91, 142.64, 142.35, 142.28, 128.46, 128.35, 128.32, 128.19, 125.93, 125.75, 109.55, 89.56, 75.31, 56.19, 51.50, 45.66, 40.11, 35.95, 33.19, 32.40, 32.12, 30.94, 29.16, 28.00, 20.90, 19.76, 18.40 |
| 33 | — | — | ESIMS m/z 587 [M + H]$^+$ | $^1$H NMR (CDCl$_3$) δ 8.55 (d, J = 7.0 Hz, 1H), 8.34 (d, J = 5.4 Hz, 1H), 7.30-7.24 (m, 4H), 7.21-7.15 (m, 4H), 7.14-7.06 (m, 2H), 7.00 (d, J = 5.5 Hz, 1H), 4.88 (m, 1H), 4.55 (dt, J = 10.8, 7.4 Hz, 1H), 3.91 (s, 3H), 2.68-2.50 (m, 3H), 2.47-2.40 (m, 1H), 2.40 (s, 3H), 2.35-2.22 (m, 1H), 1.85-1.38 (m, 11H), 1.40 (d, J = 6.3 Hz, 3H), 1.32-1.22 (m, 1H), 0.93 (dd, J = 15.1, 7.2 Hz, 1H)<br>$^{13}$C NMR (CDCl$_3$) δ 172.56, 168.93, 162.40, 159.42, 146.71, 142.35, 142.29, 141.56, 137.46, 128.46, 128.35, 128.32, 128.19, 125.93, 125.75, 109.74, 75.31, 56.28, 51.24, 45.65, 40.09, 35.93, 33.37, 32.40, 32.11, 30.93, 29.15, 28.00, 20.77, 19.73, 18.35 |
| 34 | — | (Neat) 3381, 2948, 1737, 1676, 1503, 1369, | HRMS-ESI (m/z) [M]$^+$ calcd for C$_{32}$H$_{44}$N$_2$O$_7$, 568.3149; found, | $^1$H NMR (CDCl$_3$) δ 8.33 (d, J = 8.1 Hz, 1H), 8.29 (d, J = 5.4 Hz, 1H), 7.32-7.26 (m, 2H), 7.22-7.13 (m, 3H), 6.95 (d, J = 5.4 Hz, 1H), 5.75 (s, 2H), 4.95-4.84 (m, 1H), 4.64-4.52 (m, 1H), 3.91 (s, 3H), 2.74-2.61 (m, 1H), 2.53-2.42 (m, 1H), 2.42-2.31 (m, 1H), 2.08 (s, 3H), 1.88-1.65 (m, 3H), 1.64-1.33 (m, 6H), 1.43 (d, |

TABLE 2-continued

Analytical Data

| *Cmpd. No. | MP (° C.) | IR (cm⁻¹) | MASS | NMR (¹H, ¹³C or ¹⁹F) |
|---|---|---|---|---|
| | | 1202 | 568.3158 | J = 6.3 Hz, 3H), 1.33-1.02 (m, 4H), 0.98-0.91 (m, 1H), 0.91-0.84 (m, 6H) |
| 35 | — | (Neat) 3380, 2947, 1736, 1676, 1503, 1209 | HRMS-ESI (m/z) [M]⁺ calcd for $C_{34}H_{48}N_2O_8$, 612.3411; found, 612.3412 | ¹H NMR (CDCl₃) δ 8.35 (d, J = 8.1 Hz, 1H), 8.29 (d, J = 5.4 Hz, 1H), 7.32-7.26 (m, 2H), 7.22-7.13 (m, 3H), 6.95 (d, J = 5.4 Hz, 1H), 5.83 (s, 2H), 4.94-4.83 (m, 1H), 4.62-4.51 (m, 1H), 4.10 (s, 2H), 3.91 (s, 3H), 3.60 (q, J = 7.0 Hz, 2H), 2.72-2.62 (m, 1H), 2.53-2.41 (m, 1H), 2.40-2.30 (m, 1H), 1.87-1.64 (m, 3H), 1.64-1.33 (m, 6H), 1.43 (d, J = 6.3 Hz, 3H), 1.33-1.02 (m, 4H), 1.23 (t, J = 7.0 Hz, 3H), 0.98-0.91 (m, 1H), 0.92-0.85 (m, 6H) |
| 36 | — | (Neat) 3381, 2948, 1771, 1736, 1676, 1507, 1197 | HRMS-ESI (m/z) [M]⁺ calcd for $C_{31}H_{42}N_2O_6$, 538.3043; found, 538.3046 | ¹H NMR (CDCl₃) δ 8.54 (d, J = 7.9 Hz, 1H), 8.35 (d, J = 5.5 Hz, 1H), 7.33-7.26 (m, 2H), 7.23-7.11 (m, 3H), 7.00 (d, J = 5.6 Hz, 1H), 4.94-4.82 (m, 1H), 4.62-4.50 (m, 1H), 3.91 (s, 3H), 2.73-2.60 (m, 1H), 2.52-2.40 (m, 1H), 2.40 (s, 3H), 2.38-2.28 (m, 1H), 1.86-1.63 (m, 3H), 1.63-1.32 (m, 6H), 1.42 (d, J = 6.3 Hz, 3H), 1.31-1.02 (m, 4H), 0.98-0.88 (m, 1H), 0.92-0.82 (m, 6H) |
| 37 | — | (Neat) 3370, 2931, 1736, 1676, 1503, 1202 | HRMS-ESI (m/z) [M]⁺ calcd for $C_{29}H_{38}N_2O_7$, 526.2679; found, 526.2680 | ¹H NMR (CDCl₃) δ 8.33 (d, J = 8.1 Hz, 1H), 8.28 (d, J = 5.3 Hz, 1H), 7.32-7.25 (m, 2H), 7.23-7.16 (m, 3H), 6.94 (d, J = 5.4 Hz, 1H), 5.74 (s, 2H), 4.93-4.83 (m, 1H), 4.61-4.51 (m, 1H), 3.90 (s, 3H), 2.77 (dd, J = 15.4, 3.0 Hz, 1H), 2.55 (dd, J = 15.5, 7.9 Hz, 1H), 2.43-2.32 (m, 1H), 2.06 (s, 3H), 1.99-1.88 (m, 1H), 1.86-1.71 (m, 1H), 1.65-1.51 (m, 2H), 1.49-1.27 (m, 5H), 1.19 (d, J = 6.4 Hz, 3H), 1.19-1.06 (m, 1H), 1.00-0.89 (m, 1H), 0.85 (t, J = 7.0 Hz, 3H) |
| 38 | — | (Neat) 3379, 2931, 1771, 1735, 1676, 1507, 1197 | HRMS-ESI (m/z) [M]⁺ calcd for $C_{28}H_{36}N_2O_6$, 496.2573; found, 496.2578 | ¹H NMR (CDCl₃) δ 8.55 (d, J = 6.8 Hz, 1H), 8.34 (d, J = 5.4 Hz, 1H), 7.32-7.26 (m, 2H), 7.22-7.16 (m, 3H), 6.99 (d, J = 5.5 Hz, 1H), 4.93-4.81 (m, 1H), 4.60-4.48 (m, 1H), 3.90 (s, 3H), 2.82-2.72 (m, 1H), 2.55 (dd, J = 15.5, 7.9 Hz, 1H), 2.39 (s, 3H), 2.39-2.29 (m, 1H), 1.98-1.87 (m, 1H), 1.86-1.71 (m, 1H), 1.64-1.51 (m, 2H), 1.48-1.26 (m, 5H), 1.18 (d, J = 6.4 Hz, 3H), 1.19-1.06 (m, 1H), 0.98-0.88 (m, 1H), 0.85 (t, J = 7.0 Hz, 3H) |
| 39 | — | — | ESIMS m/z 661 [M + H]⁺ | ¹H NMR (CDCl₃) δ 8.30 (d, J = 8.1 Hz, 1H), 8.27 (d, J = 5.4 Hz, 1H), 7.51 (d, J = 8.0 Hz, 2H), 7.25-7.16 (m, 4H), 7.02 (apparent triplet (at), J = 8.7 Hz, 2H), 6.94 (d, J = 5.4 Hz, 1H), 5.74 (s, 2H), 4.93 (m, 1H), 4.59 (dt, J = 11.0, 7.4 Hz, 1H), 3.90 (s, 3H), 2.92 (bd, J = 15.2 Hz, 2H), 2.74 (dd, J = 15.6, 7.5 Hz, 1H), 2.50 (dd, J = 13.7, 11.9 Hz, 1H), 2.33 (dt, J = 13.4, 6.8 Hz, 1H), 2.08 (m, 1H), 2.06 (s, 3H), 1.83-1.63 (m, 2H), 1.54 (dq, J = 14.1, 7.2 Hz, 1H), 1.46-1.34 (m, 1H), 1.29 (d, J = 6.4 Hz, 3H), 1.25-1.13 (m, 1H), 0.86 (dd, J = 15.2, 7.2 Hz, 1H) ¹³C NMR (CDCl₃) δ 172.41, 170.27, 162.99, 161.45 (d, J = 241 Hz), 160.24, 145.76, 144.77, 143.90, 142.50, 135.86 (d, J = 3 Hz), 130.55 (d, J = 7 Hz), 128.92, 128.42 (q, J = 3 Hz), 125.31 (q, J = 4 Hz), 124.25 (q, J = 271 Hz), 115.46, (d, J = 22 Hz), 109.58, 89.49, 75.58, 56.18, 51.43, 46.96, 43.87, 37.73, 36.51, 33.10, 27.38, 20.88, 20.72, 18.75 ¹⁹F NMR (CDCl₃) δ −62.33, −116.63 |
| 40 | — | — | ESIMS m/z 631 [M + H]⁺ | ¹H NMR (CDCl₃) δ 8.51 (d, J = 7.1 Hz, 1H), 8.32 (d, J = 5.4 Hz, 1H), 7.51 (d, J = 8.0 Hz, 2H), 7.24-7.12 (m, 4H), 7.08-6.91 (m, 3H), 4.99-4.84 (m, 1H), 4.57 (dt, J = 11.0, 7.3 Hz, 1H), 3.90 (s, 3H), 2.91 (bd, J = 13.1 Hz, 2H), 2.73 (dd, J = 15.6, 7.5 Hz, 1H), 2.49 (dd, J = 13.7, 11.9 Hz, 1H), 2.39 (s, 3H), 2.30 (dt, J = 16.6, 7.8 Hz, 1H), 2.12-2.02 (m, 1H), 1.77 (m, 1H), 1.68-1.60 (m, 1H), 1.52 (dd, J = 13.7, 7.0 Hz, 1H), 1.45-1.31 (m, 1H), 1.27 (d, J = 6.4 Hz, 3H) 1.18 (q, J = 11.8 Hz, 1H), 0.85 (dd, J = 14.6, 7.2 Hz, 1H) ¹³C NMR (CDCl₃) δ 172.30, 168.91, 162.42, 161.44 (d, J = 244 Hz), 159.43, 146.71, 144.76, |

TABLE 2-continued

Analytical Data

| *Cmpd. No. | MP (° C.) | IR (cm⁻¹) | MASS | NMR (¹H, ¹³C or ¹⁹F) |
|---|---|---|---|---|
| | | | | 141.45, 137.47, 135.86 (d, J = 3 Hz), 130.14 (d, J = 8 Hz), 128.91, 128.43 (q, J = 32 Hz), 125.32 (q, J = 3 Hz), 124.24 (q, J = 270 Hz), 115.47, (d, J = 21 Hz), 109.94, 75.59, 56.29, 51.16, 46.97, 43.88, 37.73, 36.52, 33.27, 27.39, 20.75, 20.70, 18.72<br>¹⁹F NMR (CDCl₃) δ −62.33, −116.63 |
| 41 | — | — | ESIMS m/z 689 [M + H]⁺ | ¹H NMR (CDCl₃) δ 8.35 (d, J = 8.1 Hz, 1H), 8.26 (d, J = 5.4 Hz, 1H), 7.51 (d, J = 8.0 Hz, 2H), 7.25-7.13 (m, 4H), 7.02 (t, J = 8.6 Hz, 2H), 6.93 (d, J = 5.4 Hz, 1H), 5.88-5.60 (m, 2H), 4.93 (dd, J = 9.6, 6.4 Hz, 1H), 4.59 (dt, J = 11.0, 7.5 Hz, 1H), 3.88 (s, 3H), 2.92 (d, J = 15.0 Hz, 2H), 2.74 (dd, J = 15.6, 7.5 Hz, 1H), 2.60-2.44 (m, 2H), 2.33 (dt, J = 13.4, 6.8 Hz, 1H), 2.09 (dd, J = 7.3, 3.0 Hz, 1H), 1.86-1.64 (m, 2H), 1.54 (m, 1H), 1.47-1.33 (m, 1H), 1.28 (d, J = 6.4 Hz, 3H), 1.20 (m, 1H), 1.13 (d, J = 7.0 Hz, 6H), 0.91-0.81 (m, 1H)<br>¹³C NMR (CDCl₃) δ 176.24, 172.41, 162.96, 161.44 (d, J = 242 Hz), 160.23, 145.62, 144.78, 144.13, 142.15, 135.87 (d, J = 3 Hz), 130.14 (d, J = 8 Hz), 128.92, 128.42 (q, J = 3 Hz), 125.30 (q, J = 4 Hz), 124.25 (q, J = 271 Hz), 115.46, (d, J = 21 Hz), 109.53, 89.85, 75.56, 56.13, 51.42, 46.97, 43.88, 37.73, 36.52, 33.86, 33.10, 27.38, 20.72, 18.76, 18.68<br>¹⁹F NMR (CDCl₃) δ −62.33, −116.63 |
| 42 | — | — | ESIMS m/z 533 [M + H]⁺ | ¹H NMR (CDCl₃) δ 8.36 (d, J = 8.0 Hz, 1H), 8.28 (d, J = 5.4 Hz, 1H), 6.94 (d, J = 5.4 Hz, 1H), 5.75 (d, J = 1.1 Hz, 2H), 4.95 (p, J = 6.4 Hz, 1H), 4.55 (dt, J = 11.1, 7.3 Hz, 1H), 3.91 (s, 3H), 2.34 (dt, J = 13.5, 6.6 Hz, 1H), 2.07 (s, 3H), 1.97-1.43 (m, 17H), 1.35 (d, J = 6.4 Hz, 3H), 1.38-1.03 (m, 4H), 0.89 (dd, J = 6.6, 2.2 Hz, 6H)<br>¹³C NMR (CDCl₃) δ 172.62, 170.27, 162.94, 160.23, 145.75, 143.87, 142.70, 109.50, 89.57, 74.81, 56.17, 52.05, 49.88, 42.56, 38.42, 37.21, 33.55, 31.43, 30.09, 28.45, 28.38, 27.80, 25.07, 24.34, 22.96, 22.49, 21.48, 20.89, 19.13 |
| 43 | — | — | ESIMS m/z 503 [M + H]⁺ | ¹H NMR (CDCl₃) δ 8.58 (d, J = 5.6 Hz, 1H), 8.33 (d, J = 5.4 Hz, 1H), 6.99 (d, J = 5.5 Hz, 1H), 4.95 (p, J = 6.4 Hz, 1H), 4.54 (m, 1H), 3.90 (s, 3H), 2.40 (s, 3H), 2.31 (dt, J = 13.5, 6.3 Hz, 1H), 1.97 (m, 2H), 1.76 (m, 1H), 1.69-1.44 (m, 14H), 1.36-1.03 (m, 4H), 1.33 (d, J = 6.4 Hz, 3H), 0.88 (dd, J = 6.6, 2.8 Hz, 6H)<br>¹³C NMR (CDCl₃) δ 172.52, 168.93, 162.36, 159.40, 146.69, 141.61, 137.43, 109.70, 74.80, 56.27, 51.82, 49.96, 42.57, 38.41, 37.22, 33.72, 31.42, 30.11, 28.45, 27.77, 25.07, 24.36, 22.95, 22.48, 21.49, 20.76, 19.08 |
| 44 | — | — | ESIMS m/z 561 [M + H]⁺ | ¹H NMR (CDCl₃) δ 8.42 (d, J = 8.0 Hz, 1H), 8.27 (d, J = 5.4 Hz, 1H), 6.93 (d, J = 5.4 Hz, 1H), 5.86-5.63 (m, 2H), 4.95 (m, 1H), 4.56 (m, 1H), 3.89 (s, 3H), 2.55 (p, J = 7.0 Hz, 1H), 2.34 (dt, J = 13.6, 6.6 Hz, 1H), 2.01-1.42 (m, 17H), 1.37-1.03 (m, 4H), 1.35 (d, J = 6.4 Hz, 3H), 1.14 (d, J = 7.0 Hz, 6H), 0.89 (dd, J = 6.6, 2.1 Hz, 6H)<br>¹³C NMR (CDCl₃) δ 176.24, 172.62, 162.91, 160.21, 145.62, 144.10, 142.35, 109.44, 89.94, 74.79, 56.11, 52.05, 49.89, 42.56, 38.43, 37.22, 33.86, 33.55, 31.42, 30.09, 28.45, 28.39, 27.79, 25.07, 24.35, 22.96, 22.50, 21.49, 19.13, 18.69 |
| 45 | — | — | HRMS-FAB (m/z) [M + H]⁺ calcd for C₃₀H₄₁N₂O₆, 525.2964; found, 525.2966 | ¹H NMR (CDCl₃) δ 8.50 (d, J = 8.2 Hz, 1H), 8.31 (d, J = 5.4 Hz, 1H), 7.35-7.23 (m, 2H), 7.23-7.09 (m, 3H), 6.98 (d, J = 5.5 Hz, 1H), 4.82 (dq, J = 9.7, 6.3 Hz, 1H), 4.56 (ddd, J = 11.0, 8.4, 7.2 Hz, 1H), 3.88 (s, 3H), 2.98-2.76 (m, 1H), 2.40 (s, 3H), 2.38-2.22 (m, 2H), 1.85-1.75 (m, 1H), 1.72-1.43 (m, 7H), 1.35 (d, J = 6.3 Hz, 3H), 1.33-1.25 (m, 1H), 1.23-1.06 (m, 2H), 0.93 (d, J = 6.6 Hz, 6H), 0.83-0.73 (m, 1H) |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | | $^{13}$C NMR (CDCl$_3$) δ 172.44, 168.89, 162.40, 159.41, 146.70, 141.54, 141.18, 137.44, 128.73, 128.34, 125.87, 109.75, 75.23, 56.27, 51.16, 45.32, 42.41, 37.93, 34.51, 33.40, 28.87, 27.52, 27.20, 22.75, 22.47, 20.77, 19.66, 18.58 |
| 46 | — | — | HRMS-FAB (m/z) [M + H]$^+$ calcd for C$_{28}$H$_{36}$FN$_2$O$_6$, 515.2557; found, 515.2552 | $^1$H NMR (CDCl$_3$) δ 8.55 (d, J = 8.5 Hz, 1H), 8.33 (d, J = 5.4 Hz, 1H), 7.21-7.08 (m, 2H), 7.06-6.86 (m, 3H), 4.85 (dq, J = 9.6, 6.4 Hz, 1H), 4.54 (ddd, J = 10.9, 8.3, 7.1 Hz, 1H), 3.89 (s, 3H), 2.80-2.64 (m, 1H), 2.53 (dd, J = 15.5, 7.8 Hz, 1H), 2.39 (s, 3H), 2.38-2.30 (m, 1H), 1.93-1.81 (m, 1H), 1.81-1.71 (m, 1H), 1.63-1.51 (m, 2H), 1.48-1.25 (m, 5H), 1.17 (d, J = 6.4 Hz, 3H), 1.15-1.07 (m, 1H), 0.96-0.89 (m, 1H), 0.85 (t, J = 7.1 Hz, 3H) $^{19}$F NMR (CDCl$_3$) δ −117.36 |
| 47 | — | — | HRMS-FAB (m/z) [M + H]$^+$ calcd for C$_{31}$H$_{43}$N$_2$O$_7$, 555.3070; found, 555.3074 | $^1$H NMR (CDCl$_3$) δ 8.29 (d, J = 8.1 Hz, 1H), 8.26 (d, J = 5.4 Hz, 1H), 7.37-7.25 (m, 2H), 7.23-7.12 (m, 3H), 6.93 (d, J = 5.4 Hz, 1H), 5.74 (s, 2H), 4.82 (dq, J = 9.7, 6.3 Hz, 1H), 4.58 (ddd, J = 11.0, 8.2, 7.2 Hz, 1H), 3.89 (s, 3H), 2.90-2.74 (m, 1H), 2.43-2.25 (m, 2H), 2.06 (s, 3H), 1.86-1.76 (m, 1H), 1.72-1.44 (m, 7H), 1.36 (d, J = 6.3 Hz, 3H), 1.33-1.23 (m, 1H), 1.22-1.08 (m, 2H), 0.93 (d, J = 6.6 Hz, 6H), 0.83-0.75 (m, 1H) $^{13}$C NMR (CDCl$_3$) δ 172.55, 170.24, 162.96, 160.22, 145.75, 143.86, 142.61, 141.18, 128.73, 128.33, 125.86, 109.55, 89.51, 75.20, 56.18, 51.41, 45.32, 42.39, 37.93, 34.49, 33.21, 28.86, 27.51, 27.20, 22.74, 22.46, 20.88, 19.67, 18.61 |
| 48 | — | — | HRMS-FAB (m/z) [M + H]$^+$ calcd for C$_{29}$H$_{38}$FN$_2$O$_7$, 545.2663; found, 545.2660 | $^1$H NMR (CDCl$_3$) δ 8.34 (d, J = 8.0 Hz, 1H), 8.28 (d, J = 5.3 Hz, 1H), 7.21-7.09 (m, 2H), 7.06-6.89 (m, 3H), 5.74 (s, 2H), 4.86 (dq, J = 9.6, 6.4 Hz, 1H), 4.56 (ddd, J = 10.9, 8.1, 7.1 Hz, 1H), 3.90 (s, 3H), 2.81-2.67 (m, 1H), 2.54 (dd, J = 15.5, 7.8 Hz, 1H), 2.37 (dddd, J = 13.4, 7.9, 5.7, 2.1 Hz, 1H), 2.06 (s, 3H), 1.95-1.85 (m, 1H), 1.84-1.73 (m, 1H), 1.68-1.53 (m, 2H), 1.51-1.27 (m, 5H), 1.19 (d, J = 6.4 Hz, 3H), 1.17-1.10 (m, 1H), 0.96-0.90 (m, 1H), 0.86 (t, J = 7.1 Hz, 3H) $^{19}$F NMR (CDCl$_3$) δ −117.37 |
| 49 | — | — | HRMS-FAB (m/z) [M + H]$^+$ calcd for C$_{32}$H$_{45}$N$_2$O$_6$, 553.3277; found, 553.3275 | $^1$H NMR (CDCl$_3$) δ 8.44 (d, J = 6.4 Hz, 1H), 8.30 (d, J = 5.4 Hz, 1H), 7.34-7.23 (m, 2H), 7.21-7.11 (m, 3H), 6.96 (d, J = 5.5 Hz, 1H), 4.81 (dq, J = 9.7, 6.3 Hz, 1H), 4.57 (ddd, J = 10.9, 8.5, 7.2 Hz, 1H), 3.86 (s, 3H), 2.95 (hept, J = 7.0 Hz, 1H), 2.87-2.78 (m, 1H), 2.40-2.24 (m, 2H), 1.84-1.76 (m, 1H), 1.69-1.46 (m, 7H), 1.36 (d, J = 7.1 Hz, 6H), 1.34 (d, J = 5.5 Hz, 3H), 1.32-1.26 (m, 1H), 1.22-1.08 (m, 2H), 0.93 (d, J = 6.6 Hz, 6H), 0.82-0.73 (m, 1H) $^{13}$C NMR (CDCl$_3$) δ 174.68, 172.51, 162.38, 159.37, 146.61, 141.95, 141.19, 137.59, 128.73, 128.33, 125.86, 109.59, 75.16, 56.27, 51.11, 45.33, 42.42, 37.94, 34.50, 33.95, 33.43, 28.87, 27.50, 27.21, 22.75, 22.47, 19.65, 18.84, 18.59 |
| 50 | — | — | HRMS-FAB (m/z) [M + H]$^+$ calcd for C$_{33}$H$_{47}$N$_2$O$_7$, 583.3383; found, 583.3379 | $^1$H NMR (CDCl$_3$) δ 8.35 (d, J = 8.1 Hz, 1H), 8.26 (d, J = 5.3 Hz, 1H), 7.32-7.25 (m, 2H), 7.21-7.12 (m, 3H), 6.92 (d, J = 5.4 Hz, 1H), 5.85-5.64 (m, 2H), 4.82 (dq, J = 9.7, 6.3 Hz, 1H), 4.58 (ddd, J = 11.0, 8.1, 7.1 Hz, 1H), 3.88 (s, 3H), 3.00-2.79 (m, 1H), 2.54 (hept, J = 7.0 Hz, 1H), 2.40-2.26 (m, 2H), 1.81 (ddt, J = 10.8, 7.4, 3.6 Hz, 1H), 1.71-1.47 (m, 7H), 1.36 (d, J = 6.3 Hz, 3H), 1.33-1.20 (m, 3H), 1.14 (d, J = 7.0 Hz, 6H), 0.93 (d, J = 6.6 Hz, 6H), 0.84-0.75 (m, 1H) $^{13}$C NMR (CDCl$_3$) δ 176.22, 172.55, 162.94, 160.22, 145.61, 144.10, 142.27, 141.19, 128.73, 128.33, 125.86, 109.48, 89.90, 75.19, 56.12, 51.41, 45.33, 42.40, 37.94, 34.50, 33.86, 33.23, 28.86, 27.51, 27.21, 22.74, 22.46, 19.67, 18.68, 18.62 |

TABLE 2-continued

Analytical Data

| *Cmpd. No. | MP (° C.) | IR (cm⁻¹) | MASS | NMR (¹H, ¹³C or ¹⁹F) |
|---|---|---|---|---|
| 51 | — | — | HRMS-FAB (m/z) [M + H]⁺ calcd for C$_{33}$H$_{47}$N$_2$O$_8$, 599.3332; found, 599.3335 | ¹H NMR (CDCl$_3$) δ 8.31 (d, J = 8.1 Hz, 1H), 8.26 (d, J = 5.3 Hz, 1H), 7.34-7.24 (m, 2H), 7.23-7.11 (m, 3H), 6.94 (d, J = 5.4 Hz, 1H), 5.82 (s, 2H), 4.82 (dq, J = 9.7, 6.3 Hz, 1H), 4.65-4.49 (m, 1H), 4.09 (s, 2H), 3.89 (s, 3H), 3.59 (q, J = 7.0 Hz, 2H), 2.91-2.76 (m, 1H), 2.41-2.24 (m, 2H), 1.81 (ddt, J = 12.1, 7.9, 2.2 Hz, 1H), 1.72-1.45 (m, 7H), 1.36 (d, J = 6.2 Hz, 3H), 1.33-1.25 (m, 1H), 1.23 (t, J = 7.0 Hz, 3H), 1.19-1.06 (m, 2H), 0.93 (d, J = 6.6 Hz, 6H), 0.84-0.75 (m, 1H) ¹³C NMR (CDCl$_3$) δ 172.52, 170.04, 162.91, 160.15, 145.80, 143.82, 142.45, 141.17, 128.72, 128.33, 125.86, 109.66, 89.53, 75.22, 67.79, 67.16, 56.21, 51.39, 45.32, 42.38, 37.93, 34.49, 33.20, 28.86, 27.51, 27.19, 22.74, 22.46, 19.67, 18.60, 15.02 |
| 52 | — | — | ESIMS m/z 561 [M + H]⁺ | ¹H NMR (CDCl$_3$) δ 8.32 (d, J = 8.2 Hz, 1H), 8.28 (d, J = 5.4 Hz, 1H), 7.36 (at, J = 7.3 Hz, 2H), 7.31-7.15 (m, 5H), 7.12 (dd, J = 8.4, 6.1 Hz, 1H), 6.94 (d, J = 5.4 Hz, 1H), 6.90 (d, J = 6.9 Hz, 2H), 5.75 (s, 2H), 5.21 (m, 1H), 4.67 (dt, J = 10.9, 7.6 Hz, 1H), 3.90 (s, 3H), 2.78 (t, J = 9.9 Hz, 1H), 2.53 (bd, J = 12.6 Hz, 1H), 2.39 (dt, J = 13.1, 6.5 Hz, 1H), 2.26 (m, 1H), 2.16 (bd, J = 10.3 Hz, 1H), 2.07 (s, 3H), 1.75 (m, 1H), 1.61 (m, 2H), 1.29 (q, J = 10.8 Hz, 1H), 1.11 (m, 1H), 0.97 (d, J = 6.4 Hz, 3H) ¹³C NMR (CDCl$_3$) δ 172.71, 170.28, 163.00, 160.25, 145.76, 143.91, 142.57, 142.22, 140.82, 128.75, 128.60, 128.17, 127.00, 125.78, 109.58, 89.53, 75.36, 56.19, 55.19, 51.41, 46.80, 37.54, 33.35, 27.25, 20.89, 20.62, 18.23 |
| 53 | — | — | ESIMS m/z 531 [M + H]⁺ | ¹H NMR (CDCl$_3$) δ 8.53 (d, J = 7.1 Hz, 1H), 8.33 (d, J = 5.4 Hz, 1H), 7.36 (at, J = 7.4 Hz, 2H), 7.30-7.14 (m, 5H), 7.11 (at, J = 7.3 Hz, 1H), 6.99 (d, J = 5.5 Hz, 1H), 6.89 (d, J = 8.2 Hz, 2H), 5.20 (m, 1H), 4.65 (dt, J = 10.8, 7.6 Hz, 1H), 3.89 (s, 3H), 2.76 (t, J = 9.9 Hz, 1H), 2.52 (d, J = 13.2 Hz, 1H), 2.40 (s, 3H), 2.37 (m, 1H), 2.26 (m, 1H), 2.14 (m, 1H), 1.74 (m, 1H), 1.60 (m, 2H), 1.26 (q, J = 10.8 Hz, 1H), 1.10 (m, 1H), 0.95 (d, J = 6.4 Hz, 3H) ¹³C NMR (CDCl$_3$) δ 172.58, 168.92, 162.44, 159.43, 146.72, 142.21, 141.50, 140.82, 137.47, 128.75, 128.59, 128.17, 127.00, 125.78, 109.78, 75.37, 56.29, 55.17, 51.14, 46.80, 37.53, 33.53, 27.25, 20.77, 20.60, 18.19 |
| 54 | — | — | ESIMS m/z 513 [M + H]⁺ | ¹H NMR (CDCl$_3$) δ 8.36 (d, J = 8.1 Hz, 1H), 8.30 (d, J = 5.4 Hz, 1H), 7.30 (at, J = 7.3 Hz, 2H), 7.22 (at, J = 7.3 Hz, 1H), 7.16-7.10 (m, 2H), 6.95 (d, J = 5.4 Hz, 1H), 5.75 (s, 2H), 5.17 (m, 1H), 4.65 (m, 1H), 3.91 (s, 3H), 2.61 (t, J = 9.9 Hz, 1H), 2.43 (dt, J = 13.3, 6.8 Hz, 1H), 2.08 (s, 3H), 1.94-1.78 (m, 2H), 1.75-1.53 (m, 2H), 1.38 (q, J = 11.8 Hz, 1H), 1.31-0.93 (m, 5H), 0.91 (d, J = 6.4 Hz, 3H), 0.69 (t, J = 7.2 Hz, 3H) ¹³C NMR (CDCl$_3$) δ 172.84, 170.29, 162.99, 160.25, 145.76, 143.93, 142.63, 129.01, 128.47, 126.65, 109.56, 89.56, 75.61, 56.19, 55.53, 51.50, 43.47, 33.49, 33.34, 27.98, 20.89, 20.54, 20.06, 18.15, 14.01 |
| 55 | — | — | ESIMS m/z 483 [M + H]⁺ | ¹H NMR (CDCl$_3$) δ 8.64-8.50 (bs, 1H), 8.35 (d, J = 5.4 Hz, 1H), 7.29 (at, J = 7.3 Hz, 2H), 7.22 (at, J = 7.3 Hz, 1H), 7.12 (m, 2H), 7.01 (d, J = 5.5 Hz, 1H), 5.16 (m, 1H), 4.63 (dt, J = 10.7, 7.6 Hz, 1H), 3.91 (s, 3H), 2.59 (t, J = 9.9 Hz, 1H), 2.39 (m, 1H), 2.40 (s, 3H), 1.95-1.78 (m, 2H), 1.71-1.52 (m, 2H), 1.4-0.93 (m, 6H), 0.90 (d, J = 6.4 Hz, 3H), 0.68 (t, J = 7.2 Hz, 3H) ¹³C NMR (CDCl$_3$) δ 172.72, 168.94, 162.44, 159.43, 146.73, 142.62, 141.55, 137.47, 129.05, 128.47, 126.65, 109.77, 75.63, 56.29, 55.51, 51.25, 43.46, 33.49, 27.98, 20.77, 20.51, 20.06, 18.10, 14.00 |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| 56 | — | — | HRMS-FAB (m/z) [M + H]$^+$ calcd for C$_{31}$H$_{43}$N$_2$O$_6$, 539.3121; found, 539.3123 | $^1$H NMR (CDCl$_3$) δ 8.54 (d, J = 8.2 Hz, 1H), 8.33 (d, J = 5.4 Hz, 1H), 7.34-7.23 (m, 2H), 7.23-7.10 (m, 3H), 6.99 (d, J = 5.4 Hz, 1H), 4.70 (dq, J = 9.5, 6.4 Hz, 1H), 4.52 (ddd, J = 10.8, 8.4, 7.2 Hz, 1H), 3.89 (s, 3H), 2.69-2.49 (m, 2H), 2.39 (s, 3H), 2.36-2.24 (m, 1H), 1.80-1.68 (m, 2H), 1.65-1.53 (m, 1H), 1.54-1.33 (m, 5H), 1.30 (d, J = 6.4 Hz, 3H), 1.27-1.15 (m, 4H), 0.92-0.78 (m, 8H) $^{13}$C NMR (CDCl$_3$) δ 172.59, 168.91, 162.37, 159.41, 146.70, 142.42, 141.58, 137.44, 128.39, 128.26, 125.71, 109.73, 77.03, 56.27, 51.26, 44.13, 43.23, 41.40, 35.93, 33.46, 30.43, 29.26, 27.91, 27.39, 24.02, 21.88, 20.76, 19.72, 18.34 |
| 57 | — | — | ESIMS m/z 657 [M + H]$^+$ | $^1$H NMR (CDCl$_3$) δ 8.55 (d, J = 8.3 Hz, 1H), 8.33 (d, J = 5.4 Hz, 1H), 7.32-7.23 (m, 2H), 7.21-7.10 (m, 7H), 6.99 (d, J = 5.4 Hz, 1H), 4.86 (dq, J = 9.6, 6.4 Hz, 1H), 4.53 (dt, J = 10.9, 7.6 Hz, 1H), 3.89 (s, 3H), 2.68 (dd, J = 15.5, 3.5 Hz, 1H), 2.62-2.45 (m, 3H), 2.39 (s, 3H), 2.33 (dt, J = 13.5, 6.6 Hz, 1H), 2.06-1.66 (m, 4H), 1.64-0.68 (m, 10H) $^{13}$C NMR (CDCl$_3$) δ 172.38, 168.85, 162.34, 159.37, 147.44 (q, J = 1.7 Hz), 146.66, 142.23, 141.46, 139.54, 137.41, 129.97, 128.26, 125.75, 120.87, 125.24-115.10 (m), 109.71, 75.70, 56.22, 51.23, 47.48, 41.75, 36.71, 35.98, 33.29, 31.16, 29.67, 29.25, 27.82, 20.70, 18.47 $^{19}$F NMR (CDCl$_3$) δ −57.90 |
| 58 | — | — | ESIMS m/z 683 [M − H]$^-$ | $^1$H NMR (CDCl$_3$) δ 8.49 (d, J = 8.4 Hz, 1H), 8.32 (d, J = 5.4 Hz, 1H), 7.32-7.24 (m, 2H), 7.22-7.10 (m, 7H), 6.97 (d, J = 5.5 Hz, 1H), 4.86 (dq, J = 9.5, 6.3 Hz, 1H), 4.55 (dt, J = 10.8, 7.5 Hz, 1H), 3.87 (s, 3H), 2.95 (hept, J = 7.0 Hz, 1H), 2.68 (dd, J = 15.5, 3.5 Hz, 1H), 2.63-2.45 (m, 3H), 2.39-2.29 (m, 1H), 2.08-0.67 (m, 20H) $^{13}$C NMR (CDCl$_3$) δ 174.64, 172.44, 162.32, 159.33, 147.42 (q, J = 1.6 Hz), 146.55, 142.22, 141.86, 139.55, 137.56, 129.97, 128.25, 125.73, 120.86, 124.60-116.51 (m), 109.54, 75.63, 56.21, 51.17, 47.48, 41.75, 36.69, 35.97, 33.89, 33.30, 31.16, 29.66, 29.25, 27.78, 20.67, 18.76, 18.47 $^{19}$F NMR (CDCl$_3$) δ −57.89 |
| 59 | — | — | ESIMS m/z 687 [M + H]$^+$ | $^1$H NMR (CDCl$_3$) δ 8.33 (d, J = 8.0 Hz, 1H), 8.27 (d, J = 5.3 Hz, 1H), 7.30-7.24 (m, 2H), 7.20-7.10 (m, 7H), 6.94 (d, J = 5.4 Hz, 1H), 5.74 (s, 2H), 4.86 (dq, J = 9.5, 6.3 Hz, 1H), 4.55 (dt, J = 10.8, 7.5 Hz, 1H), 2.68 (dd, J = 15.5, 3.5 Hz, 1H), 2.61-2.46 (m, 3H), 2.40-2.31 (m, 1H), 2.06 (s, 3H), 1.95-1.85 (m, 1H), 1.85-1.66 (m, 2H), 1.65-0.68 (m, 14H) $^{13}$C NMR (CDCl$_3$) δ 172.47, 170.20, 162.90, 160.18, 147.41 (q, J = 1.6 Hz), 145.69, 143.86, 142.50, 142.22, 139.53, 129.96, 128.25, 125.73, 120.86, 124.37-116.45 (m), 109.50, 89.46, 75.67, 56.11, 51.47, 47.46, 41.73, 36.67, 35.97, 33.10, 31.15, 29.65, 29.25, 27.79, 20.81, 20.69 $^{19}$F NMR (CDCl$_3$) δ −57.90 |
| 60 | — | — | HRMS-FAB (m/z) [M + H]$^+$ calcd for C$_{29}$H$_{37}$N$_2$O$_6$, 509.2651; found, 509.2643 | $^1$H NMR (CDCl$_3$) δ 8.69-8.48 (m, 1H), 8.33 (d, J = 5.4 Hz, 1H), 7.35-7.23 (m, 2H), 7.23-7.11 (m, 3H), 6.99 (d, J = 5.5 Hz, 1H), 4.89 (dq, J = 9.7, 6.4 Hz, 1H), 4.55 (ddd, J = 10.9, 8.3, 7.1 Hz, 1H), 3.89 (s, 3H), 2.71 (dd, J = 15.6, 3.1 Hz, 1H), 2.58-2.49 (m, 1H), 2.39 (s, 3H), 2.37-2.32 (m, 1H), 2.04-1.93 (m, 1H), 1.93-1.85 (m, 1H), 1.66-1.58 (m, 2H), 1.57-1.46 (m, 2H), 1.37-1.28 (m, 1H), 1.19 (d, J = 6.3 Hz, 3H), 1.08-0.98 (m, 2H), 0.73-0.58 (m, 1H), 0.51-0.39 (m, 1H), 0.39-0.28 (m, 1H), 0.09-0.00 (m, 1H), −0.07--0.19 (m, 1H) |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | | $^{13}$C NMR (CDCl$_3$) δ 172.45, 168.91, 162.38, 159.41, 146.71, 141.55, 140.84, 137.44, 128.81, 128.39, 126.00, 109.76, 76.19, 56.28, 51.30, 46.80, 42.69, 37.34, 36.62, 33.51, 28.38, 20.76, 20.72, 18.91, 9.19, 5.66, 3.75 |
| 61 | — | — | HRMS-FAB (m/z) [M + H]$^+$ calcd for C$_{30}$H$_{39}$N$_2$O$_7$, 539.2757; found, 539.2760 | $^1$H NMR (CDCl$_3$) δ 8.34 (d, J = 8.0 Hz, 1H), 8.28 (d, J = 5.4 Hz, 1H), 7.33-7.24 (m, 2H), 7.23-7.10 (m, 3H), 6.94 (d, J = 5.4 Hz, 1H), 5.74 (s, 2H), 4.89 (dq, J = 9.7, 6.4 Hz, 1H), 4.57 (ddd, J = 10.9, 8.0, 7.1 Hz, 1H), 3.90 (s, 3H), 2.71 (dd, J = 15.5, 3.1 Hz, 1H), 2.53 (dd, J = 15.5, 7.8 Hz, 1H), 2.46-2.34 (m, 1H), 2.06 (s, 3H), 2.04-1.86 (m, 2H), 1.71-1.57 (m, 2H), 1.59-1.48 (m, 2H), 1.38-1.29 (m, 1H), 1.20 (d, J = 6.3 Hz, 3H), 1.09-0.98 (m, 2H), 0.75-0.57 (m, 1H), 0.52-0.40 (m, 1H), 0.40-0.28 (m, 1H), 0.08--0.01 (m, 1H), -0.08--0.19 (m, 1H) $^{13}$C NMR (CDCl$_3$) δ 172.56, 170.26, 162.95, 160.23, 145.76, 143.89, 142.63, 140.84, 128.81, 128.38, 125.99, 109.55, 89.54, 76.17, 56.18, 51.56, 46.79, 42.69, 37.33, 36.61, 33.34, 28.37, 20.88, 20.73, 18.95, 9.18, 5.66, 3.74 |
| 62 | — | — | HRMS-FAB (m/z) [M + H]$^+$ calcd for C$_{32}$H$_{36}$FN$_2$O$_6$, 563.2557; found, 563.2554 | $^1$H NMR (CDCl$_3$) δ 8.51 (d, J = 8.4 Hz, 1H), 8.31 (d, J = 5.4 Hz, 1H), 7.33-7.15 (m, 5H), 7.12-7.06 (m, 2H), 7.06-6.94 (m, 3H), 4.91 (dq, J = 9.7, 6.4 Hz, 1H), 4.57 (ddd, J = 11.0, 8.3, 7.1 Hz, 1H), 3.88 (s, 3H), 3.03-2.81 (m, 2H), 2.77-2.65 (m, 1H), 2.39 (s, 3H), 2.34-2.25 (m, 1H), 2.05 (tdd, J = 9.8, 7.5, 3.1 Hz, 1H), 1.82-1.70 (m, 1H), 1.70-1.61 (m, 1H), 1.61-1.52 (m, 1H), 1.52-1.41 (m, 1H), 1.33-1.24 (m, 1H), 1.25 (d, J = 6.4 Hz, 3H), 1.22-1.10 (m, 1H), 0.88-0.76 (m, 1H) $^{19}$F NMR (CDCl$_3$) δ -116.90 |
| 63 | — | — | HRMS-FAB (m/z) [M + H]$^+$ calcd for C$_{33}$H$_{38}$FN$_2$O$_7$, 593.2663; found, 593.2662 | $^1$H NMR (CDCl$_3$) δ 8.29 (d, J = 8.1 Hz, 1H), 8.26 (d, J = 5.4 Hz, 1H), 7.32-7.14 (m, 5H), 7.14-7.06 (m, 2H), 7.06-6.97 (m, 2H), 6.93 (d, J = 5.4 Hz, 1H), 5.73 (s, 2H), 4.92 (dq, J = 9.7, 6.4 Hz, 1H), 4.58 (ddd, J = 11.0, 8.1, 7.0 Hz, 1H), 3.89 (s, 3H), 3.04-2.86 (m, 2H), 2.70 (dd, J = 15.6, 7.7 Hz, 1H), 2.44 (dd, J = 13.8, 11.6 Hz, 1H), 2.38-2.27 (m, 1H), 2.12-2.02 (m, 1H), 2.06 (s, 3H), 1.82-1.63 (m, 2H), 1.63-1.52 (m, 1H), 1.53-1.39 (m, 1H), 1.27 (d, J = 6.5 Hz, 3H), 1.24-1.14 (m, 1H), 0.96-0.76 (m, 1H) $^{19}$F NMR (CDCl$_3$) δ -116.92 |
| 64 | — | — | HRMS-FAB (m/z) [M + H]$^+$ calcd for C$_{35}$H$_{42}$FN$_2$O$_7$, 621.2976; found, 621.2975 | $^1$H NMR (CDCl$_3$) δ 8.35 (d, J = 8.1 Hz, 1H), 8.25 (d, J = 5.3 Hz, 1H), 7.33-7.13 (m, 5H), 7.13-7.06 (m, 2H), 7.06-6.98 (m, 2H), 6.92 (d, J = 5.4 Hz, 1H), 5.87-5.67 (m, 2H), 4.92 (dq, J = 9.7, 6.4 Hz, 1H), 4.58 (ddd, J = 11.0, 8.1, 7.1 Hz, 1H), 3.87 (s, 3H), 3.02-2.87 (m, 2H), 2.70 (dd, J = 15.7, 7.6 Hz, 1H), 2.54 (hept, J = 7.0 Hz, 1H), 2.44 (dd, J = 13.8, 11.6 Hz, 1H), 2.38-2.27 (m, 1H), 2.07 (tdd, J = 9.8, 7.5, 3.0 Hz, 1H), 1.80-1.64 (m, 2H), 1.64-1.51 (m, 1H), 1.47 (dddd, J = 18.3, 9.2, 4.5, 2.9 Hz, 1H), 1.26 (d, J = 6.3 Hz, 3H), 1.25-1.16 (m, 1H), 1.13 (d, J = 7.0 Hz, 6H), 0.88-0.79 (m, 1H) $^{19}$F NMR (CDCl$_3$) δ -116.91 |
| 65 | — | (Neat) 3391, 2940, 1741, 1678, 1508, 1326, 1260 | HRMS-ESI (m/z) [M]$^+$ calcd for C$_{35}$H$_{36}$F$_6$N$_2$O$_8$, 726.2376; found, 726.2383 | $^1$H NMR (CDCl$_3$) δ 8.30 (d, J = 8.2 Hz, 1H), 8.27 (d, J = 5.3 Hz, 1H), 7.55-7.49 (m, 2H), 7.32-7.26 (m, 2H), 7.22-7.15 (m, 4H), 6.94 (d, J = 5.4 Hz, 1H), 5.74 (s, 2H), 5.00-4.88 (m, 1H), 4.65-4.53 (m, 1H), 3.91 (s, 3H), 3.01-2.87 (m, 2H), 2.76 (dd, J = 15.7, 7.6 Hz, 1H), 2.58-2.47 (m, 1H), 2.40-2.29 (m, 1H), 2.16-2.05 (m, 1H), 2.06 (s, 3H), 1.83-1.64 (m, 2H), 1.64-1.48 (m, 1H), 1.47-1.35 (m, 1H), 1.28 (d, J = 6.4 Hz, 3H), 1.28-1.15 (m, 1H), 0.94-0.81 (m, 1H) $^{19}$F NMR (CDCl$_3$) δ -57.95, -62.35 |
| 66 | — | (Neat) 3379, 2940, | HRMS-ESI (m/z) [M]$^+$ | $^1$H NMR (CDCl$_3$) δ 8.31 (d, J = 8.1 Hz, 1H), 8.27 (d, J = 5.4 Hz, 1H), 7.54-7.49 (m, 2H), 7.31-7.26 (m, 2H), 7.21-7.16 (m, 4H), 6.94 (d, |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | 1738, 1677, 1508, 1325, 1259 | calcd for C$_{37}$H$_{40}$F$_6$N$_2$O$_9$, 770.2638; found, 770.2644 | J = 5.4 Hz, 1H), 5.82 (s, 2H), 4.99-4.89 (m, 1H), 4.62-4.52 (m, 1H), 4.09 (s, 2H), 3.90 (s, 3H), 3.58 (q, J = 7.0 Hz, 2H), 3.00-2.88 (m, 2H), 2.76 (dd, J = 15.7, 7.5 Hz, 1H), 2.56-2.47 (m, 1H), 2.38-2.28 (m, 1H), 2.17-2.06 (m, 1H), 1.83-1.64 (m, 2H), 1.62-1.48 (m, 1H), 1.48-1.34 (m, 1H), 1.28 (d, J = 6.4 Hz, 3H), 1.22 (t, J = 7.0 Hz, 3H), 1.24-1.15 (m, 1H), 0.93-0.81 (m, 1H) $^{19}$F NMR (CDCl$_3$) δ −57.95, −62.35 |
| 67 | — | (Neat) 3379, 2941, 1772, 1738, 1678, 1508, 1325, 1259 | HRMS-ESI (m/z) [M]$^+$ calcd for C$_{34}$H$_{34}$F$_6$N$_2$O$_7$, 696.2270; found, 696.2275 | $^1$H NMR (CDCl$_3$) δ 8.51 (d, J = 8.3 Hz, 1H), 8.33 (d, J = 5.4 Hz, 1H), 7.54-7.48 (m, 2H), 7.32-7.26 (m, 2H), 7.22-7.14 (m, 4H), 6.99 (d, J = 5.5 Hz, 1H), 4.99-4.88 (m, 1H), 4.63-4.52 (m, 1H), 3.90 (s, 3H), 3.01-2.86 (m, 2H), 2.76 (dd, J = 15.7, 7.6 Hz, 1H), 2.57-2.46 (m, 1H), 2.39 (s, 3H), 2.36-2.26 (m, 1H), 2.15-2.05 (m, 1H), 1.83-1.62 (m, 2H), 1.61-1.47 (m, 1H), 1.47-1.34 (m, 1H), 1.27 (d, J = 5.8 Hz, 3H), 1.26-1.11 (m, 1H), 0.93-0.80 (m, 1H) $^{19}$F NMR (CDCl$_3$) δ −57.94, −62.35 |
| 68 | — | (Neat) 3379, 2940, 1738, 1677, 1507, 1258, 1202 | HRMS-ESI (m/z) [M]$^+$ calcd for C$_{34}$H$_{37}$F$_3$N$_2$O$_8$, 658.2502; found, 658.2501 | $^1$H NMR (CDCl$_3$) δ 8.29 (d, J = 8.7 Hz, 1H), 8.27 (d, J = 5.4 Hz, 1H), 7.32-7.23 (m, 4H), 7.22-7.15 (m, 3H), 7.11-7.06 (m, 2H), 6.93 (d, J = 5.4 Hz, 1H), 5.73 (s, 2H), 4.99-4.87 (m, 1H), 4.64-4.53 (m, 1H), 3.90 (s, 3H), 3.03-2.88 (m, 2H), 2.73 (dd, J = 15.7, 7.7 Hz, 1H), 2.51-2.40 (m, 1H), 2.40-2.27 (m, 1H), 2.14-2.04 (m, 1H), 2.06 (s, 3H), 1.82-1.40 (m, 4H), 1.29-1.14 (m, 4H), 0.91-0.80 (m, 1H) $^{19}$F NMR (CDCl$_3$) δ −57.93 |
| 69 | — | (Neat) 3382, 2939, 1737, 1677, 1507, 1258, 1206 | HRMS-ESI (m/z) [M]$^+$ calcd for C$_{36}$H$_{41}$F$_3$N$_2$O$_9$, 702.2764; found, 702.2774 | $^1$H NMR (CDCl$_3$) δ 8.31 (d, J = 8.1 Hz, 1H), 8.26 (d, J = 5.4 Hz, 1H), 7.32-7.23 (m, 4H), 7.23-7.14 (m, 3H), 7.12-7.05 (m, 2H), 6.93 (d, J = 5.5 Hz, 1H), 5.82 (s, 2H), 4.99-4.87 (m, 1H), 4.62-4.52 (m, 1H), 4.09 (s, 2H), 3.90 (s, 3H), 3.58 (q, J = 7.0 Hz, 2H), 3.02-2.88 (m, 2H), 2.73 (dd, J = 15.8, 7.7 Hz, 1H), 2.51-2.41 (m, 1H), 2.38-2.27 (m, 1H), 2.16-2.05 (m, 1H), 1.82-1.40 (m, 4H), 1.31-1.15 (m, 4H), 1.22 (t, J = 7.0 Hz, 3H), 0.91-0.80 (m, 1H) $^{19}$F NMR (CDCl$_3$) δ −57.93 |
| 70 | — | (Neat) 3377, 2935, 1736, 1676, 1497, 1371, 1202 | HRMS-ESI (m/z) [M]$^+$ calcd for C$_{35}$H$_{42}$N$_2$O$_7$, 602.2992; found, 602.2995 | $^1$H NMR (CDCl$_3$) δ 8.33 (d, J = 8.0 Hz, 1H), 8.28 (d, J = 5.4 Hz, 1H), 7.30-7.24 (m, 4H), 7.22-7.12 (m, 6H), 6.94 (d, J = 5.4 Hz, 1H), 5.74 (s, 2H), 4.93-4.82 (m, 1H), 4.60-4.49 (m, 1H), 3.90 (s, 3H), 2.73 (dd, J = 15.4, 3.3 Hz, 1H), 2.63-2.44 (m, 3H), 2.42-2.29 (m, 1H), 2.06 (s, 3H), 1.99-1.86 (m, 1H), 1.85-1.64 (m, 2H), 1.64-1.24 (m, 7H), 1.21 (d, J = 6.4 Hz, 3H), 1.00-0.88 (m, 1H) |
| 71 | — | — | HRMS-FAB (m/z) [M + H]$^+$ calcd for C$_{27}$H$_{37}$N$_2$O$_5$, 469.2702; found, 469.2701 | $^1$H NMR (CDCl$_3$) δ 12.16 (s, 1H), 8.47 (d, J = 8.2 Hz, 1H), 7.97 (d, J = 5.2 Hz, 1H), 7.35-7.25 (m, 2H), 7.23-7.09 (m, 3H), 6.85 (d, J = 5.2 Hz, 1H), 4.85 (dq, J = 9.6, 6.3 Hz, 1H), 4.56 (dt, J = 11.0, 7.7 Hz, 1H), 3.92 (s, 3H), 2.94-2.78 (m, 1H), 2.41-2.25 (m, 2H), 1.81 (tq, J = 10.6, 3.3 Hz, 1H), 1.71-1.14 (m, 11H), 1.37 (d, J = 6.3 Hz, 3H), 0.95 (t, J = 7.1 Hz, 3H), 0.85-0.74 (m, 1H) $^{13}$C NMR (CDCl$_3$) δ 171.95, 168.64, 155.31, 148.70, 141.09, 140.48, 130.49, 128.71, 128.35, 125.90, 109.43, 75.65, 56.05, 51.09, 45.33, 42.53, 37.89, 33.11, 29.35, 27.82, 27.46, 23.50, 19.70, 18.53, 14.04 |
| 72 | — | — | HRMS-FAB (m/z) [M + H]$^+$ calcd for C$_{28}$H$_{36}$F$_3$N$_2$O$_5$, 537.2576; found, 537.2588 | $^1$H NMR (CDCl$_3$) δ 12.13 (s, 1H), 8.47 (d, J = 8.2 Hz, 1H), 7.97 (d, J = 5.2 Hz, 1H), 7.54 (d, J = 8.0 Hz, 2H), 7.37-7.18 (m, 2H), 6.85 (d, J = 5.2 Hz, 1H), 4.85 (dq, J = 9.7, 6.3 Hz, 1H), 4.56 (ddd, J = 11.0, 8.3, 7.2 Hz, 1H), 3.93 (s, 3H), 2.96-2.81 (m, 1H), 2.43 (dd, J = 13.9, 11.3 Hz, 1H), 2.32 (dt, J = 13.5, 7.0 Hz, 1H), 1.90-1.77 (m, 1H), 1.75-1.15 (m, 11H), 1.38 (d, J = 6.3 Hz, 1H), 0.95 (t, J = 7.1 Hz, 3H), 0.90-0.77 (m, 1H) |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | | $^{13}$C NMR (CDCl$_3$) δ 171.86, 168.69, 155.35, 148.74, 145.30, 140.48, 130.48, 128.99, 128.35 (q, J = 32.2 Hz), 125.29 (q, J = 3.8 Hz), 124.30 (q, J = 255 Hz), 109.47, 75.49, 56.03, 51.05, 45.40, 42.47, 37.81, 33.02, 29.38, 27.86, 27.48, 23.44, 19.64, 18.55, 13.96 |
| 73 | — | — | HRMS-FAB (m/z) [M + H]$^+$ calcd for C$_{28}$H$_{39}$N$_2$O$_5$, 483.2859; found, 483.2847 | $^1$H NMR (CDCl$_3$) δ 12.15 (d, J = 0.6 Hz, 1H), 8.51 (d, J = 8.2 Hz, 1H), 7.98 (d, J = 5.2 Hz, 1H), 7.45-7.11 (m, 5H), 6.86 (dd, J = 5.3, 0.7 Hz, 1H), 4.90 (dq, J = 9.6, 6.4 Hz, 1H), 4.54 (ddd, J = 10.9, 8.2, 7.1 Hz, 1H), 3.93 (s, 3H), 2.76 (dd, J = 15.4, 3.2 Hz, 1H), 2.57 (dd, J = 15.4, 7.8 Hz, 1H), 2.42-2.27 (m, 1H), 2.03-1.89 (m, 1H), 1.88-1.73 (m, 1H), 1.67-1.54 (m, 2H), 1.53-1.24 (m, 6H), 1.21 (d, J = 6.4 Hz, 3H), 1.07-0.91 (m, 2H), 0.85 (d, J = 6.6 Hz, 6H) $^{13}$C NMR (CDCl$_3$) δ 171.98, 168.62, 155.32, 148.70, 140.92, 140.49, 130.51, 128.82, 128.42, 126.02, 109.42, 76.48, 56.06, 51.24, 47.53, 42.26, 37.51, 36.76, 33.12, 29.33, 28.25, 27.83, 23.04, 22.32, 20.78, 18.54 |
| 74 | — | — | HRMS-FAB (m/z) [M + H]$^+$ calcd for C$_{30}$H$_{35}$N$_2$O$_5$, 503.2546; found, 503.2537 | $^1$H NMR (CDCl$_3$) δ 12.13 (d, J = 0.6 Hz, 1H), 8.47 (d, J = 8.2 Hz, 1H), 7.98 (d, J = 5.2 Hz, 1H), 7.41-7.04 (m, 10H), 6.85 (d, J = 5.3, 0.7 Hz, 1H), 4.96 (dq, J = 9.7, 6.4 Hz, 1H), 4.56 (ddd, J = 11.0, 8.2, 7.1 Hz, 1H), 3.93 (s, 3H), 2.98 (td, J = 14.1, 12.7, 3.0 Hz, 2H), 2.73 (dd, J = 15.6, 7.6 Hz, 1H), 2.43 (dd, J = 13.8, 11.6 Hz, 1H), 2.36-2.27 (m, 1H), 2.17-1.98 (m, 1H), 1.84-1.66 (m, 2H), 1.67-1.55 (m, 1H), 1.55-1.40 (m, 1H), 1.29 (d, J = 6.4 Hz, 3H), 1.27-1.18 (m, 1H), 0.91-0.82 (m, 1H) $^{13}$C NMR (CDCl$_3$) δ 171.87, 168.63, 155.33, 148.71, 140.68, 140.49, 140.48, 130.49, 128.87, 128.69, 128.58, 128.34, 126.26, 125.97, 109.43, 76.26, 56.06, 51.14, 46.88, 44.18, 37.85, 37.31, 33.15, 27.43, 20.75, 18.70 |
| 75 | — | — | HRMS-FAB (m/z) [M + H]$^+$ calcd for C$_{28}$H$_{37}$N$_2$O$_5$, 481.2702; found, 481.2687 | $^1$H NMR (CDCl$_3$) δ 12.16 (s, 1H), 8.51 (d, J = 8.2 Hz, 1H), 7.98 (d, J = 5.2 Hz, 1H), 7.38-7.14 (m, 5H), 6.85 (d, J = 5.2 Hz, 1H), 4.99 (dq, J = 8.5, 6.3 Hz, 1H), 4.55 (ddd, J = 11.2, 8.1, 6.6 Hz, 1H), 3.93 (s, 3H), 2.87 (dd, J = 14.3, 3.7 Hz, 1H), 2.61 (dd, J = 14.2, 11.3 Hz, 1H), 2.26 (dt, J = 13.2, 6.7 Hz, 1H), 2.16-1.96 (m, 3H), 1.91-1.44 (m, 11H), 1.41 (d, J = 6.4 Hz, 3H), 1.39-1.20 (m, 2H), 0.92-0.78 (m, 1H) $^{13}$C NMR (CDCl$_3$) δ 171.96, 168.62, 155.31, 148.69, 140.99, 140.49, 130.51, 128.63, 128.31, 125.92, 109.42, 74.95, 56.06, 51.62, 48.71, 42.55, 40.07, 39.46, 33.26, 29.47, 28.76, 27.76, 25.22, 24.48, 21.48, 19.57 |
| 76 | — | — | HRMS-FAB (m/z) [M + H]$^+$ calcd for C$_{27}$H$_{36}$ClN$_2$O$_5$, 503.2312; found, 503.2311 | $^1$H NMR (CDCl$_3$) δ 12.13 (s, 1H), 8.47 (d, J = 8.2 Hz, 1H), 7.98 (d, J = 5.2 Hz, 1H), 7.32-7.18 (m, 2H), 7.16-7.03 (m, 2H), 6.86 (d, J = 5.2 Hz, 1H), 4.78 (dq, J = 9.4, 6.4 Hz, 1H), 4.55 (ddd, J = 11.0, 8.2, 7.1 Hz, 1H), 3.93 (s, 3H), 2.92-2.78 (m, 1H), 2.34-2.27 (m, 2H), 1.77-1.47 (m, 4H), 1.44-1.32 (m, 2H), 1.38 (d, J = 6.3 Hz, 3H), 1.29-1.06 (m, 2H), 0.98 (d, J = 6.5 Hz, 3H), 0.96 (d, J = 6.7 Hz, 3H), 0.90-0.80 (m, 2H) $^{13}$C NMR (CDCl$_3$) δ 171.92, 168.64, 155.33, 148.70, 140.50, 139.43, 131.64, 130.47, 130.00, 128.47, 109.43, 76.99, 56.06, 51.07, 45.86, 43.73, 41.53, 36.82, 33.13, 27.58, 27.26, 24.08, 21.96, 19.73, 18.48 |
| 77 | 73-76 | — | ESIMS m/z 469 [M + H]$^+$ | $^1$H NMR (CDCl$_3$) δ 12.15 (d, J = 0.6 Hz, 1H), 8.46 (d, J = 8.2 Hz, 1H), 7.97 (d, J = 5.2 Hz, 1H), 7.31-7.26 (m, 2H), 7.22-7.14 (m, 3H), 6.85 (d, J = 5.2 Hz, 1H), 4.78 (dq, J = 8.8, 6.4 Hz, 1H), 4.56 (ddd, J = 11.0, 8.3, 7.2 Hz, 1H), 3.93 (s, 3H), 2.90 (d, J = 13.8 Hz, 1H), 2.40-2.25 (m, 2H), 1.80-1.51 (m, 5H), 1.50-1.34 (m, 5H), 1.30-1.11 (m, 2H), 0.99 (d, J = 6.6 Hz, 3H), 0.96 (d, J = 6.6 Hz, 3H), 0.88-0.79 (m, 1H) |

TABLE 2-continued

Analytical Data

| *Cmpd. No. | MP (° C.) | IR (cm⁻¹) | MASS | NMR (¹H, ¹³C or ¹⁹F) |
|---|---|---|---|---|
| | | | | $^{13}$C NMR (CDCl$_3$) δ 171.93, 168.59, 155.27, 148.65, 140.96, 140.43, 130.45, 128.64, 128.30, 125.88, 109.37, 77.05, 56.01, 51.06, 45.86, 43.72, 41.49, 37.39, 33.15, 27.56, 27.27, 24.07, 21.91, 19.72, 18.47 |
| 78 | — | (Neat) 3369, 2939, 1736, 1649, 1529, 1451, 1264 | HRMS-ESI (m/z) [M]⁺ calcd for C$_{31}$H$_{36}$N$_2$O$_5$, 516.2624; found, 516.2640 | $^1$H NMR (CDCl$_3$) δ 12.15 (s, 1H), 8.47 (d, J = 8.2 Hz, 1H), 7.99 (d, J = 5.2 Hz, 1H), 7.35-7.27 (m, 4H), 7.25-7.12 (m, 6H), 6.86 (d, J = 5.2 Hz, 1H), 5.0-4.89 (m, 1H), 4.63-4.52 (m, 1H), 3.94 (s, 3H), 2.90-2.72 (m, 2H), 2.60-2.49 (m, 1H), 2.40-2.27 (m, 2H), 1.97-1.73 (m, 4H), 1.73-1.50 (m, 3H), 1.49 (d, J = 6.3 Hz, 3H), 1.33-1.21 (m, 1H), 0.91-0.79 (m, 1H) |
| 79 | — | (Neat) 3368, 2938, 1736, 1649, 1528, 1481, 1264 | HRMS-ESI (m/z) [M]⁺ calcd for C$_{30}$H$_{33}$ClN$_2$O$_5$, 536.2078; found, 536.2079 | $^1$H NMR (CDCl$_3$) δ 12.12 (s, 1H), 8.47 (d, J = 8.2 Hz, 1H), 7.98 (d, J = 5.2 Hz, 1H), 7.36-7.29 (m, 2H), 7.28-7.19 (m, 5H), 7.03-6.98 (m, 2H), 6.85 (d, J = 5.2 Hz, 1H), 5.01-4.90 (m, 1H), 4.61-4.51 (m, 1H), 3.93 (s, 3H), 2.95 (dd, J = 15.6, 3.3 Hz, 1H), 2.92-2.84 (m, 1H), 2.74 (dd, J = 15.6, 7.4 Hz, 1H), 2.40 (dd, J = 13.9, 11.7 Hz, 1H), 2.37-2.26 (m, 1H), 2.17-2.06 (m, 1H), 1.80-1.64 (m, 2H), 1.61-1.37 (m, 2H), 1.30 (d, J = 6.4 Hz, 3H), 1.27-1.18 (m, 1H), 0.91-0.79 (m, 1H) |
| 80 | — | — | HRMS-FAB (m/z) [M + H]⁺ calcd for C$_{28}$H$_{36}$F$_3$N$_2$O$_5$, 537.2576; found, 537.2566 | $^1$H NMR (CDCl$_3$) δ 12.15 (s, 1H), 8.48 (d, J = 8.2 Hz, 1H), 7.97 (d, J = 5.2 Hz, 1H), 7.54 (d, J = 8.0 Hz, 2H), 7.36-7.18 (m, 2H), 6.86 (d, J = 5.2 Hz, 1H), 4.78 (dq, J = 9.2, 6.4 Hz, 1H), 4.57 (ddd, J = 11.0, 8.3, 7.2 Hz, 1H), 3.93 (s, 3H), 3.01-2.85 (m, 1H), 2.41 (dd, J = 13.8, 10.9 Hz, 1H), 2.32 (dt, J = 13.5, 6.8 Hz, 1H), 1.81-1.48 (m, 5H), 1.47-1.31 (m, 2H), 1.39 (d, J = 6.4 Hz, 3H), 1.31-1.18 (m, 1H), 1.13 (dd, J = 14.8, 10.1 Hz, 1H), 1.00 (d, J = 6.5 Hz, 3H), 0.97 (d, J = 6.5 Hz, 3H), 0.92-0.80 (m, 1H) $^{19}$F NMR (CDCl$_3$) δ −62.26 |
| 81 | — | — | HRMS-FAB (m/z) [M + H]⁺ calcd for C$_{31}$H$_{34}$F$_3$N$_2$O$_5$, 571.2420; found, 571.2405 | $^1$H NMR (CDCl$_3$) δ 12.14 (s, 1H), 8.48 (d, J = 8.1 Hz, 1H), 7.97 (d, J = 5.2 Hz, 1H), 7.56-7.14 (m, 9H), 6.85 (d, J = 5.3 Hz, 1H), 4.96 (dq, J = 9.7, 6.3 Hz, 1H), 4.57 (dt, J = 11.0, 7.6 Hz, 1H), 3.92 (s, 3H), 3.03-2.87 (m, 2H), 2.77 (dd, J = 15.6, 7.3 Hz, 1H), 2.48 (dd, J = 13.9, 11.7 Hz, 1H), 2.32 (dt, J = 13.5, 6.9 Hz, 1H), 2.20-2.07 (m, 1H), 1.86-1.73 (m, 1H), 1.75-1.65 (m, 1H), 1.62-1.48 (m, 1H), 1.46-1.37 (m, 1H), 1.32 (d, J = 6.3 Hz, 3H), 1.31-1.17 (m, 2H) $^{19}$F NMR (CDCl$_3$) δ −62.25 |
| 82 | — | (Neat) 3368, 2930, 1735, 1649, 1496, 1449, 1263 | HRMS-ESI (m/z) [M]⁺ calcd for C$_{26}$H$_{34}$N$_2$O$_5$, 454.2468; found, 454.2476 | $^1$H NMR (CDCl$_3$) δ 12.14 (d, J = 0.6 Hz, 1H), 8.51 (d, J = 8.2 Hz, 1H), 7.99 (d, J = 5.2 Hz, 1H), 7.32-7.26 (m, 2H), 7.23-7.16 (m, 3H), 6.86 (dd, J = 5.3, 0.6 Hz, 1H), 4.95-4.85 (m, 1H), 4.54 (ddd, J = 11.0, 8.2, 7.1 Hz, 1H), 3.94 (s, 3H), 2.78 (dd, J = 15.5, 3.2 Hz, 1H), 2.56 (dd, J = 15.5, 7.9 Hz, 1H), 2.42-2.29 (m, 1H), 2.01-1.89 (m, 1H), 1.88-1.72 (m, 1H), 1.66-1.57 (m, 2H), 1.48-1.27 (m, 5H), 1.21 (d, J = 6.4 Hz, 3H), 1.19-1.07 (m, 1H), 0.99-0.89 (m, 1H), 0.86 (t, J = 6.8 Hz, 3H) |
| 83 | — | (Neat) 3368, 2947, 1735, 1649, 1450, 1280 | HRMS-ESI (m/z) [M]⁺ calcd for C$_{29}$H$_{40}$N$_2$O$_5$, 496.2937; found, 496.2946 | $^1$H NMR (CDCl$_3$) δ 12.16 (s, 1H), 8.51 (d, J = 8.2 Hz, 1H), 8.00 (d, J = 5.2 Hz, 1H), 7.33-7.26 (m, 2H), 7.23-7.13 (m, 3H), 6.87 (dd, J = 5.1 Hz, 1H), 4.97-4.86 (m, 1H), 4.61-4.51 (m, 1H), 3.94 (s, 3H), 2.68 (ddd, J = 13.6, 11.5, 5.3 Hz, 1H), 2.47 (ddd, J = 13.6, 11.4, 5.8 Hz, 1H), 2.42-2.29 (m, 1H), 1.90-1.65 (m, 3H), 1.64-1.31 (m, 6H), 1.44 (d, J = 6.3 Hz, 3H), 1.30-1.02 (m, 4H), 0.98-0.93 (m, 1H), 0.93-0.84 (m, 6H) |
| 84 | — | — | HRMS-FAB (m/z) [M + H]⁺ calcd for C$_{28}$H$_{36}$ClN$_2$O$_5$, 515.2313; found, | $^1$H NMR (CDCl$_3$) δ 12.14 (d, J = 0.6 Hz, 1H), 8.51 (d, J = 8.1 Hz, 1H), 7.98 (d, J = 5.2 Hz, 1H), 7.38-7.19 (m, 2H), 7.19-7.04 (m, 2H), 6.86 (d, J = 5.2 Hz, 1H), 4.99 (dq, J = 8.5, 6.4 Hz, 1H), 4.55 (ddd, J = 11.2, 8.1, 6.6 Hz, 1H), 3.94 (s, 3H), 2.83 (dd, J = 14.4, 3.8 Hz, 1H), 2.60 (dd, J = 14.3, 11.3 Hz, 1H), 2.26 (dt, J = 13.5, 6.8 Hz, |

TABLE 2-continued

Analytical Data

| *Cmpd. No. | MP (° C.) | IR (cm⁻¹) | MASS | NMR ($^1$H, $^{13}$C or $^{19}$F) |
|---|---|---|---|---|
| | | | 515.2306 | 1H), 2.09-1.78 (m, 3H), 1.78-1.44 (m, 9H), 1.41 (d, J = 6.4 Hz, 3H), 1.37-1.20 (m, 3H), 0.91-0.79 (m, 1H) $^{13}$C NMR (CDCl$_3$) δ 171.90, 168.63, 155.33, 148.70, 140.50, 139.42, 131.59, 130.50, 129.94, 128.44, 109.42, 74.83, 56.06, 51.59, 48.80, 42.56, 40.05, 38.83, 33.24, 29.55, 28.81, 27.65, 25.18, 24.45, 21.50, 19.52 |
| 85 | — | — | ESIMS m/z 545 [M + H]⁺ | $^1$H NMR (CDCl$_3$) δ 12.15 (s, 1H), 8.51 (d, J = 8.2 Hz, 1H), 7.99 (d, J = 5.2 Hz, 1H), 7.31-7.24 (m, 4H), 7.23-7.14 (m, 4H), 7.09 (d, J = 6.9 Hz, 2H), 6.86 (d, J = 5.2 Hz, 1H), 4.90 (dq, J = 12.6, 6.2 Hz, 1H), 4.54 (dt, J = 10.8, 7.5 Hz, 1H), 3.93 (s, 3H), 2.71-2.50 (m, 3H), 2.48-2.39 (m, 1H), 2.33 (dd, J = 13.1, 6.0 Hz, 1H), 1.99-1.19 (m, 12 H), 1.43 (d, J = 6.3 Hz, 3H), 0.95 (dd, J = 15.4, 6.9 Hz, 1H) $^{13}$C NMR (CDCl$_3$) δ 172.06, 168.66, 155.35, 148.73, 142.31, 142.21, 140.51, 130.51, 128.48, 128.36, 128.34, 128.20, 125.97, 125.78, 109.45, 75.62, 56.08, 51.17, 45.65, 40.09, 35.94, 33.08, 32.41, 32.11, 30.91, 29.14, 27.96, 19.78, 18.35 |
| 86 | — | — | ESIMS m/z 589 [M + H]⁺ | $^1$H NMR (CDCl$_3$) δ 12.10 (s, 1H), 8.47 (d, J = 8.2 Hz, 1H), 7.98 (d, J = 5.2 Hz, 1H), 7.52 (d, J = 8.0 Hz, 2H), 7.25-7.14 (m, 4H), 7.03 (at, J = 8.7 Hz, 2H), 6.86 (d, J = 5.2 Hz, 1H), 4.95 (dq, J = 9.7, 6.4 Hz, 1H), 4.57 (dt, J = 11.0, 7.3 Hz, 1H), 3.93 (s, 3H), 2.93 (d, J = 15.2 Hz, 2H), 2.74 (dd, J = 15.7, 7.5 Hz, 1H), 2.50 (dd, J = 13.7, 11.9 Hz, 1H), 2.32 (dt, J = 13.4, 6.8 Hz, 1H), 2.15-2.05 (m, 1H), 1.96-1.36 (m, 5H), 1.30 (d, J = 6.4 Hz, 3H), 0.87 (dd, J = 14.9, 7.5 Hz, 1H) $^{13}$C NMR (CDCl$_3$) δ 171.80, 168.66, 161.46 (d, J = 243 Hz), 155.35, 148.72, 144.66, 140.52, 135.79 (d, J = 3 Hz), 130.41, 130.14 (d, J = 7 Hz), 128.9, 128.48 (q, J = 32 Hz), 125.35 (q, J = 3 Hz), 124.23 (q, J = 270 Hz), 115.50, (d, J = 21 Hz), 109.47, 75.87, 56.07, 51.09 46.97, 43.82, 37.73, 36.51, 33.01, 27.36, 20.73, 18.7 $^{19}$F NMR (CDCl$_3$) δ −62.35, −116.54 |
| 87 | — | — | ESIMS m/z 461 [M + H]⁺ | $^1$H NMR (CDCl$_3$) δ 12.17 (s, 1H), 8.54 (d, J = 8.1 Hz, 1H), 7.99 (d, J = 5.2 Hz, 1H), 6.86 (d, J = 5.2 Hz, 1H), 4.98 (p, J = 6.4 Hz, 1H), 4.53 (m, 1H), 3.94 (s, 3H), 2.33 (m, 1H), 1.91 (m, 2H), 1.77 (m, 1H), 1.71-1.06 (m, 18H), 1.36 (d, J = 6.4 Hz, 3H), 0.89 (dd, J = 6.6, 2.3 Hz, 6H) $^{13}$C NMR (CDCl$_3$) δ 172.00, 168.61, 155.31, 148.69, 140.47, 130.57, 109.39, 75.09, 56.05, 51.72, 49.91, 42.56, 38.42, 37.21, 33.44, 31.41, 30.09, 28.45, 27.75, 25.06, 24.35, 22.95, 22.49, 21.50, 19.07 |
| 88 | — | — | HRMS-FAB (m/z) [M + H]⁺ calcd for C$_{28}$H$_{39}$N$_2$O$_5$, 483.2859; found, 483.2865 | $^1$H NMR (CDCl$_3$) δ 12.16 (d, J = 0.6 Hz, 1H), 8.46 (d, J = 8.2 Hz, 1H), 7.98 (d, J = 5.2 Hz, 1H), 7.32-7.25 (m, 2H), 7.23-7.12 (m, 3H), 6.85 (dd, J = 5.3, 0.7 Hz, 1H), 4.84 (dq, J = 9.8, 6.3 Hz, 1H), 4.56 (ddd, J = 11.0, 8.2, 7.2 Hz, 1H), 3.93 (s, 3H), 2.93-2.80 (m, 1H), 2.41-2.25 (m, 2H), 1.82 (tt, J = 10.8, 3.4 Hz, 1H), 1.74-1.42 (m, 7H), 1.37 (d, J = 6.3 Hz, 3H), 1.35-1.02 (m, 3H), 0.93 (d, J = 6.6 Hz, 6H), 0.84-0.71 (m, 1H) $^{13}$C NMR (CDCl$_3$) δ 171.93, 168.63, 155.31, 148.70, 141.09, 140.47, 130.49, 128.71, 128.36, 125.90, 109.41, 75.52, 56.05, 51.08, 45.32, 42.31, 37.93, 34.48, 33.11, 28.86, 27.47, 27.18, 22.73, 22.45, 19.68, 18.54 |
| 89 | — | — | HRMS-FAB (m/z) [M + H]⁺ calcd for C$_{26}$H$_{34}$FN$_2$O$_5$, 473.2452; found, 473.2451 | $^1$H NMR (CDCl$_3$) δ 12.13 (d, J = 0.6 Hz, 1H), 8.51 (d, J = 8.2 Hz, 1H), 7.99 (d, J = 5.2 Hz, 1H), 7.19-7.08 (m, 2H), 7.06-6.94 (m, 2H), 6.86 (d, J = 5.4 Hz, 1H), 4.88 (dq, J = 9.6, 6.4 Hz, 1H), 4.54 (ddd, J = 11.0, 8.2, 7.1 Hz, 1H), 3.94 (s, 3H), 2.80-2.67 (m, 1H), 2.54 (dd, J = 15.5, 7.9 Hz, 1H), 2.42-2.30 (m, 1H), 1.95-1.74 (m, 2H), 1.65-1.57 (m, 2H), 1.51-1.30 (m, 5H), 1.20 (d, J = 6.3 Hz, 3H), 1.13 (ddd, J = 12.8, |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | | 10.0, 5.5 Hz, 1H), 0.99-0.91 (m, 1H), 0.86 (t, J = 7.1 Hz, 3H)<br>$^{19}$F NMR (CDCl$_3$) δ −117.29 |
| 90 | — | — | ESIMS m/z 489 [M + H]$^+$ | $^1$H NMR (CDCl$_3$) δ 12.14 (s, 1H), 8.49 (d, J = 8.2 Hz, 1H), 7.99 (d, J = 5.2 Hz, 1H), 7.36 (at, J = 7.4 Hz, 2H), 7.32-7.15 (m, 5H), 7.12 (at, J = 7.3 Hz, 1H), 6.90 (d, J = 6.9 Hz, 2H), 6.86 (d, J = 5.2 Hz, 1H), 5.28-5.17 (m, 1H), 4.71-4.60 (m, 1H), 3.94 (s, 3H), 2.79 (t, J = 9.9 Hz, 1H), 2.54 (d, J = 12.6 Hz, 1H), 2.38 (dt, J = 13.0, 6.5 Hz, 1H), 2.26 (t, J = 12.0 Hz, 1H), 2.16 (m, 1H), 1.77 (td, J = 13.7, 12.8, 5.5 Hz, 1H), 1.70-1.51 (m, 2H), 1.34 (q, J = 11.4 Hz, 1H), 1.11 (m, 1H), 0.98 (d, J = 6.4 Hz, 3H)<br>$^{13}$C NMR (CDCl$_3$) δ 172.09, 168.68, 155.35, 148.73, 142.08, 140.73, 140.51, 130.47, 128.80, 128.59, 128.20, 127.07, 125.83, 109.46, 75.66, 56.07, 55.18, 51.08, 46.73, 37.55, 33.25, 27.21, 20.64, 18.17 |
| 91 | — | — | ESIMS m/z 441 [M + H]$^+$ | $^1$H NMR (CDCl$_3$) δ 12.16 (s, 1H), 8.54 (d, J = 8.1 Hz, 1H), 8.01 (d, J = 5.2 Hz, 1H), 7.30 (at, J = 7.3 Hz, 2H), 7.26-7.19 (m, 1H), 7.15-7.09 (m, 2H), 6.87 (d, J = 5.2 Hz, 1H), 5.19 (m, 1H), 4.63 (dt, J = 10.8, 7.6 Hz, 1H), 3.94 (s, 3H), 2.62 (t, J = 9.9 Hz, 1H), 2.41 (dt, J = 13.4, 6.7 Hz, 1H), 1.99-1.79 (m, 2H), 1.76-1.54 (m, 2H), 1.43 (q, J = 11.9, 11.4 Hz, 1H), 1.37-0.94 (m, 5H), 0.92 (d, J = 6.4 Hz, 3H), 0.69 (t, J = 7.2 Hz, 3H)<br>$^{13}$C NMR (CDCl$_3$) δ 172.21, 168.67, 155.34, 148.72, 142.48, 140.51, 130.50, 129.01, 128.50, 126.71, 109.45, 75.90, 56.07, 55.51, 51.17, 43.42, 33.48, 33.22, 27.93, 20.55, 20.05, 18.10, 14.00 |
| 92 | — | — | HRMS-FAB (m/z) [M + H]$^+$ calcd for C$_{29}$H$_{41}$N$_2$O$_5$, 497.3015; found, 497.3019 | $^1$H NMR (CDCl$_3$) δ 12.16 (s, 1H), 8.51 (d, J = 8.2 Hz, 1H), 7.98 (d, J = 5.2 Hz, 1H), 7.39-7.21 (m, 2H), 7.22-7.10 (m, 3H), 6.85 (d, J = 5.2 Hz, 1H), 4.73 (dq, J = 9.6, 6.4 Hz, 1H), 4.52 (ddd, J = 10.9, 8.2, 7.1 Hz, 1H), 3.92 (s, 3H), 2.76-2.49 (m, 2H), 2.43-2.25 (m, 1H), 1.83-1.68 (m, 2H), 1.66-1.36 (m, 6H), 1.32 (d, J = 6.5 Hz, 3H), 1.29-1.12 (m, 4H), 0.91-0.80 (m, 8H)<br>$^{13}$C NMR (CDCl$_3$) δ 172.07, 168.63, 155.31, 148.70, 142.37, 140.49, 130.51, 128.39, 128.27, 125.73, 109.42, 77.30, 56.05, 51.18, 44.12, 43.21, 41.38, 35.93, 33.16, 30.42, 29.25, 27.84, 27.41, 24.01, 21.85, 19.75, 18.33 |
| 93 | 49-53 | — | ESIMS m/z 615 [M + H]$^+$ | $^1$H NMR (CDCl$_3$) δ 12.14 (d, J = 0.6 Hz, 1H), 8.51 (d, J = 8.1 Hz, 1H), 7.98 (d, J = 5.2 Hz, 1H), 7.32-7.24 (m, 2H), 7.22-7.11 (m, 7H), 6.85 (d, J = 5.2 Hz, 1H), 4.88 (dq, J = 9.5, 6.3 Hz, 1H), 4.53 (dt, J = 10.9, 7.6 Hz, 1H), 2.69 (dd, J = 15.5, 3.5 Hz, 1H), 2.63-2.46 (m, 3H), 2.40-2.30 (m, 1H), 1.97-1.67 (m, 3H), 1.65-1.49 (m, 2H), 1.48-1.15 (m, 10H), 1.02-0.82 (m, 2H)<br>$^{13}$C NMR (CDCl$_3$) δ 171.85, 168.58, 155.26, 148.64, 147.43, 142.18, 140.44, 139.46, 130.39, 129.95, 128.25, 125.74, 124.63-116.27 (m), 120.88, 109.38, 75.96, 55.98, 51.13, 47.45, 41.71, 36.65, 35.95, 32.99, 31.12, 29.23, 27.73, 20.69, 18.43<br>$^{19}$F NMR (CDCl$_3$) δ −57.88 |
| 94 | — | — | HRMS-FAB (m/z) [M + H]$^+$ calcd for C$_{27}$H$_{35}$N$_2$O$_5$, 467.2546; found, 467.2545 | $^1$H NMR (CDCl$_3$) δ 12.15 (d, J = 0.6 Hz, 1H), 8.52 (d, J = 8.2 Hz, 1H), 7.99 (d, J = 5.2 Hz, 1H), 7.33-7.24 (m, 2H), 7.23-7.11 (m, 3H), 6.86 (dd, J = 5.3, 0.7 Hz, 1H), 4.91 (dq, J = 9.7, 6.4 Hz, 1H), 4.55 (ddd, J = 10.9, 8.2, 7.1 Hz, 1H), 3.94 (s, 3H), 2.72 (dd, J = 15.4, 3.3 Hz, 1H), 2.54 (dd, J = 15.5, 7.8 Hz, 1H), 2.44-2.31 (m, 1H), 2.09-1.86 (m, 2H), 1.72-1.61 (m, 2H), 1.59-1.45 (m, 2H), 1.46-1.32 (m, 1H), 1.21 (d, J = 6.3 Hz, 3H), 1.11-0.96 (m, 2H), 0.74-0.59 (m, 1H), 0.54-0.40 (m, 1H), 0.41-0.27 (m, 1H), 0.09-0.00 (m, 1H), −0.07−−0.20 (m, 1H) |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | | $^{13}$C NMR (CDCl$_3$) δ 171.94, 168.62, 155.32, 148.70, 140.78, 140.49, 130.52, 128.80, 128.42, 126.04, 109.42, 76.48, 56.06, 51.22, 46.80, 42.68, 37.33, 36.61, 33.26, 28.33, 20.75, 18.90, 9.18, 5.68, 3.75 |
| 95 | — | — | HRMS-FAB (m/z) [M + H]$^+$ calcd for C$_{30}$H$_{34}$FN$_2$O$_5$, 521.2452; found, 521.2452 | $^1$H NMR (CDCl$_3$) δ 12.12 (d, J = 0.6 Hz, 1H), 8.46 (d, J = 8.2 Hz, 1H), 7.98 (d, J = 5.2 Hz, 1H), 7.33-7.15 (m, 5H), 7.14-7.06 (m, 2H), 7.06-6.96 (m, 2H), 6.85 (d, J = 5.2 Hz, 1H), 4.94 (dq, J = 9.6, 6.4 Hz, 1H), 4.56 (ddd, J = 11.0, 8.2, 7.1 Hz, 1H), 3.93 (s, 3H), 3.05-2.84 (m, 2H), 2.71 (dd, J = 15.7, 7.6 Hz, 1H), 2.44 (dd, J = 13.8, 11.6 Hz, 1H), 2.38-2.25 (m, 1H), 2.08 (tdd, J = 9.8, 7.5, 3.1 Hz, 1H), 1.83-1.65 (m, 2H), 1.59 (dt, J = 13.0, 7.9 Hz, 1H), 1.48 (dddd, J = 15.0, 10.0, 8.4, 4.4 Hz, 1H), 1.32-1.17 (m, 4H), 0.92-0.80 (m, 1H) $^{19}$F NMR (CDCl$_3$) δ -116.85 |
| 96 | 76-78 | (Neat) 3371, 2941, 1739, 1650, 1529, 1325, 1260 | HRMS-ESI (m/z) [M]$^+$ calcd for C$_{32}$H$_{32}$F$_6$N$_2$O$_6$, 654.2165; found, 654.2171 | $^1$H NMR (CDCl$_3$) δ 12.09 (s, 1H), 8.46 (d, J = 8.2 Hz, 1H), 7.99 (d, J = 5.2 Hz, 1H), 7.55-7.49 (m, 2H), 7.32-7.26 (m, 2H), 7.22-7.15 (m, 4H), 6.86 (d, J = 5.1 Hz, 1H), 5.02-4.90 (m, 1H), 4.62-4.51 (m, 1H), 3.94 (s, 3H), 3.01-2.89 (m, 2H), 2.77 (dd, J = 15.7, 7.5 Hz, 1H), 2.52 (dd, J = 13.9, 11.6 Hz, 1H), 2.38-2.27 (m, 1H), 2.19-2.07 (m, 1H), 1.85-1.66 (m, 2H), 1.64-1.50 (m, 1H), 1.50-1.35 (m, 1H), 1.31-1.19 (m, 1H), 1.29 (d, J = 6.4 Hz, 3H), 0.94-0.82 (m, 1H) $^{19}$F NMR (CDCl$_3$) δ -57.95, -62.37 |
| 97 | 76-78 | (Neat) 3363, 2937, 1738, 1650, 1529, 1450, 1261 | HRMS-ESI (m/z) [M]$^+$ calcd for C$_{31}$H$_{33}$F$_3$N$_2$O$_6$, 586.2291; found, 586.2296 | $^1$H NMR (CDCl$_3$) δ 12.11 (s, 1H), 8.46 (d, J = 8.2 Hz, 1H), 7.98 (d, J = 5.2 Hz, 1H), 7.31-7.24 (m, 4H), 7.22-7.16 (m, 3H), 7.12-7.06 (m, 2H), 6.86 (d, J = 5.3 Hz, 1H), 5.02-4.89 (m, 1H), 4.62-4.51 (m, 1H), 3.94 (s, 3H), 3.05-2.88 (m, 2H), 2.74 (dd, J = 15.8, 7.7 Hz, 1H), 2.46 (dd, J = 13.8, 11.5 Hz, 1H), 2.38-2.26 (m, 1H), 2.18-2.05 (m, 1H), 1.85-1.39 (m, 4H), 1.31-1.20 (m, 1H), 1.27 (d, J = 6.3 Hz, 3H), 0.93-0.80 (m, 1H) $^{19}$F NMR (CDCl$_3$) δ -57.93 |
| 98 | — | (Neat) 3371, 2935, 1735, 1649, 1528, 1451, 1264 | HRMS-ESI (m/z) [M]$^+$ calcd for C$_{32}$H$_{38}$N$_2$O$_5$, 530.2781; found, 530.2787 | $^1$H NMR (CDCl$_3$) δ 12.13 (s, 1H), 8.50 (d, J = 8.2 Hz, 1H), 7.99 (d, J = 5.2 Hz, 1H), 7.32-7.24 (m, 4H), 7.23-7.12 (m, 6H), 6.86 (d, J = 5.2 Hz, 1H), 4.96-4.84 (m, 1H), 4.59-4.46 (m, 1H), 3.94 (s, 3H), 2.74 (dd, J = 15.5, 3.4 Hz, 1H), 2.63-2.45 (m, 3H), 2.40-2.27 (m, 1H), 2.00-1.88 (m, 1H), 1.87-1.24 (m, 9H), 1.23 (d, J = 6.4 Hz, 3H), 1.00-0.90 (m, 1H) |
| 99 | — | — | ESIMS m/z 318 [M + H]$^+$ | $^1$H NMR (CD$_3$OD) δ 7.33-7.06 (m, 5H), 4.87 (m, 1H), 3.89 (dd, J = 11.0, 7.3 Hz, 1H), 2.91-2.80 (m, 1H), 2.34 (dd, J = 13.7, 11.2 Hz, 1H), 2.29-2.15 (m, 1H), 1.85-1.74 (m, 1H), 1.71-1.16 (m, 11H), 1.39 (d, J = 6.3 Hz, 3H), 0.96 (t, J = 7.2 Hz, 3H), 0.80-0.62 (m, 1H) $^{13}$C NMR (CD$_3$OD) δ 171.18, 142.28, 129.81, 129.48, 127.06, 77.92, 52.65, 46.69, 43.98, 38.91, 31.67, 30.32, 29.03, 28.62, 24.50, 20.00, 19.11, 14.41 |
| 100 | — | — | ESIMS m/z 386 [M + H]$^+$ | $^1$H NMR (CD$_3$OD) δ 7.65-7.55 (m, 2H), 7.38 (d, J = 8.0 Hz, 2H), 4.91-4.84 (m, 1H), 3.88 (dd, J = 11.0, 7.4 Hz, 1H), 2.96 (d, J = 13.5 Hz, 1H), 2.48 (dd, J = 13.9, 11.3 Hz, 1H), 2.21 (dt, J = 13.3, 6.7 Hz, 1H), 1.97-1.80 (m, 1H), 1.77-1.54 (m, 5H), 1.54-1.15 (m, 6H), 1.41 (d, J = 6.3 Hz, 3H), 0.96 (t, J = 7.2 Hz, 3H), 0.79 (dd, J = 15.6, 8.0 Hz, 1H) $^{19}$F NMR (CD$_3$OD) δ -59.91 |
| 101 | — | — | ESIMS m/z 332 [M + H]$^+$ | $^1$H NMR (CD$_3$OD) δ 7.34-7.14 (m, 5H), 4.93-4.86 (m, 1H), 3.95-3.83 (m, 1H), 2.68 (qd, J = 15.3, 5.5 Hz, 2H), 2.28 (ddt, J = 13.9, 7.4, 3.0 Hz, 1H), 2.00-1.79 (m, 2H), 1.63 (dq, J = 9.6, 4.5 Hz, 2H), 1.51-1.35 (m, 4H), 1.36-1.26 (m, 2H), 1.24 (d, J = 6.3 Hz, 3H), 1.03 (ddt, J = 12.9, |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | | 10.3, 5.0 Hz, 1H), 0.94-0.88 (m, 1H), 0.85 (dd, J = 6.5, 1.1 Hz, 6H)<br>$^{13}$C NMR (CD$_3$OD) δ 171.16, 142.20, 130.01, 129.53, 127.18, 78.63, 52.83, 48.95, 43.42, 38.34, 37.91, 31.69, 30.57, 29.48, 28.89, 23.47, 22.76, 21.12, 19.22 |
| 102 | — | — | ESIMS m/z 352 [M + H]$^+$ | $^1$H NMR (CD$_3$OD) δ 7.37-7.04 (m, 10H), 4.96 (dq, J = 9.8, 6.4 Hz, 1H), 3.89 (dd, J = 11.1, 7.2 Hz, 1H), 3.05-2.89 (m, 2H), 2.79 (dd, J = 15.5, 7.5 Hz, 1H), 2.42 (dd, J = 13.8, 11.6 Hz, 1H), 2.21 (dt, J = 13.5, 6.8 Hz, 1H), 2.13 (tdd, J = 9.9, 7.4, 3.4 Hz, 1H), 1.88-1.55 (m, 3H), 1.53-1.39 (m, 1H), 1.34-1.25 (m, 1H), 1.30 (d, J = 6.4 Hz, 3H), 0.84-0.69 (m, 1H)<br>$^{13}$C NMR (CD$_3$OD) δ 171.10, 142.01, 130.10, 129.81, 129.62, 129.39, 127.30, 127.05, 78.61, 52.70, 48.20, 45.28, 38.80, 37.93, 31.65, 28.50, 21.05, 19.27 |
| 103 | — | — | ESIMS m/z 330 [M + H]$^+$ | — |
| 104 | — | — | — | |
| 105 | 221-224 | — | ESIMS m/z 318 [M + H]$^+$ | $^1$H NMR (CD$_3$OD) δ 7.31-7.22 (m, 2H), 7.21-7.12 (m, 3H), 4.80 (dq, J = 9.1, 6.4 Hz, 1H), 3.90 (dd, J = 11.0, 7.4 Hz, 1H), 2.97-2.86 (m, 1H), 2.33 (dd, J = 13.8, 11.0 Hz, 1H), 2.24 (dt, J = 13.6, 6.7 Hz, 1H), 1.83-1.52 (m, 5H), 1.50-1.36 (m, 5H), 1.35-1.24 (m, 1H), 1.24-1.15 (m, 1H), 1.02-0.97 (m, 6H), 0.78 (dd, J = 15.6, 7.7 Hz, 1H)<br>$^{13}$C NMR (CD$_3$OD) δ 171.14, 142.12, 129.73, 129.41, 127.02, 79.32, 52.63, 47.06, 45.01, 42.26, 38.45, 31.69, 28.81, 28.38, 24.32, 22.34, 20.06, 19.04 |
| 106 | — | — | ESIMS m/z 386 [M + H]$^+$ | $^1$H NMR (CD$_3$OD) δ 7.61-7.36 (m, 4H), 4.85-4.79 (m, 1H), 3.90 (dd, J = 11.0, 7.4 Hz, 1H), 2.99 (d, J = 13.8 Hz, 1H), 2.52-2.40 (m, 1H), 2.26-2.17 (m, 1H), 1.83-1.55 (m, 5H), 1.52-1.16 (m, 4H), 1.42 (d, J = 6.4 Hz, 1H), 1.00 (t, J = 6.8 Hz, 6H), 0.82 (dd, J = 15.3, 7.9 Hz, 1H)<br>$^{19}$F NMR (CD$_3$OD) δ −63.84 |
| 107 | — | — | ESIMS m/z 420 [M + H]$^+$ | $^1$H NMR (CD$_3$OD) δ 7.71-7.06 (m, 9H), 4.98 (dq, J = 9.7, 6.4 Hz, 1H), 3.98-3.82 (m, 1H), 2.99 (dt, J = 15.7, 3.6 Hz, 2H), 2.83 (dd, J = 15.5, 7.3 Hz, 1H), 2.53 (dd, J = 13.9, 11.7 Hz, 1H), 2.27-2.11 (m, 2H), 1.87 (ddt, J = 12.3, 8.4, 3.9 Hz, 1H), 1.81-1.70 (m, 1H), 1.61 (dq, J = 14.6, 8.1, 7.7 Hz, 1H), 1.48-1.24 (m, 2H), 1.32 (d, J = 6.3 Hz, 1H), 0.82 (dd, J = 15.6, 8.0 Hz, 1H)<br>$^{19}$F NMR (CD$_3$OD) δ −63.86 |
| 108 | — | — | ESIMS m/z 365 [M + H]$^+$ | $^1$H NMR (CD$_3$OD) δ 7.31-7.24 (m, 2H), 7.24-7.18 (m, 2H), 5.14-4.99 (m, 1H), 3.89 (dd, J = 11.2, 6.8 Hz, 1H), 2.86 (dd, J = 14.2, 4.1 Hz, 1H), 2.65 (dd, J = 14.3, 11.2 Hz, 1H), 2.24-1.99 (m, 3H), 1.94-1.80 (m, 1H), 1.80-1.47 (m, 9H), 1.44 (d, J = 6.4 Hz, 3H), 1.43-1.22 (m, 3H), 0.86 (dd, J = 14.3, 6.9 Hz, 1H) |
| 109 | — | — | ESIMS m/z 366.3 [M + H]$^+$ | $^1$H NMR (CD$_3$OD) δ 7.34-7.26 (m, 4H), 7.26-7.15 (m, 6H), 5.04-4.95 (m, 1H), 3.89 (dd, J = 11.0, 7.4 Hz, 1H), 2.92-2.75 (m, 2H), 2.65-2.54 (m, 1H), 2.34 (dd, J = 13.8, 11.1 Hz, 1H), 2.28-2.17 (m, 1H), 2.0-1.74 (m, 4H), 1.74-1.50 (m, 3H), 1.53 (d, J = 6.3 Hz, 3H), 1.39-1.25 (m, 1H), 0.88-0.76 (m, 1H) |
| 110 | — | — | ESIMS m/z 386.3 [M + H]$^+$ | $^1$H NMR (CD$_3$OD) δ 7.38-7.30 (m, 4H), 7.29-7.20 (m, 3H), 7.16-7.10 (m, 2H), 5.05-4.93 (m, 1H), 3.88 (dd, J = 11.1, 7.3 Hz, 1H), 2.99 (dd, J = 15.5, 3.7 Hz, 1H), 2.94 (dd, J = 14.0, 2.6 Hz, 1H), 2.82 (dd, J = 15.5, 7.4 Hz, 1H), 2.48-2.40 (m, 1H), 2.26-2.10 (m, 2H), 1.87-1.55 (m, 3H), 1.53-1.39 (m, 1H), 1.37-1.25 (m, 1H), 1.33 (d, J = 6.3 Hz, 3H), 0.88-0.76 (m, 1H) |
| 111 | — | — | ESIMS m/z 346.3 | $^1$H NMR (CDCl$_3$) δ 8.74 (bs, 3H), 7.31-7.26 (m, 2H), 7.21-7.16 (m, 1H), 7.15-7.09 (m, |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | [M + H]$^+$ | 2H), 4.96-4.81 (m, 1H), 4.07-3.94 (m, 1H), 2.70-2.49 (m, 2H), 2.49-2.36 (m, 1H), 1.91-1.61 (m, 3H), 1.61-1.31 (m, 6H), 1.44 (d, J = 6.2 Hz, 3H), 1.27-0.99 (m, 4H), 0.93-0.86 (m, 1H), 0.87 (d, J = 6.7 Hz, 3H), 0.85 (d, J = 6.6 Hz, 3H) |
| 112 | — | — | ESIMS m/z 304.3 [M + H]$^+$ | $^1$H NMR (CDCl$_3$) δ 8.70 (bs, 3H), 7.31-7.23 (m, 2H), 7.22-7.12 (m, 3H), 4.91-4.78 (m, 1H), 4.0-3.88 (m, 1H), 2.74 (dd, J = 15.6, 2.3 Hz, 1H), 2.57-2.44 (m, 2H), 1.93-1.46 (m, 7H), 1.44-1.22 (m, 3H), 1.17 (d, J = 6.4 Hz, 3H), 1.16-1.05 (m, 1H), 0.84 (t, J = 6.8 Hz, 3H) |
| 113 | — | — | ESIMS m/z 394 [M + H]$^+$ | $^1$H NMR (DMSO-d$_6$) δ 8.38 (bs, 3H), 7.33-7.23 (m, 4H), 7.22-7.14 (m, 4H), 7.13-7.08 (m, 2H), 4.81 (dq, J = 12.4, 6.2 Hz, 1H), 3.85 (t, J = 8.3 Hz, 1H), 2.68-2.52 (m, 3H), 2.40 (td, J = 12.7, 5.3 Hz, 1H), 2.18-2.08 (m, 1H), 1.85-1.21 (m, HH), 1.38 (d, J = 6.3 Hz, 3H), 1.10 (m, 1H), 0.73 (dd, J = 14.3, 8.0 Hz, 1H) |
| 114 | — | — | ESIMS m/z 438 [M + H]$^+$ | $^1$H NMR (DMSO-d$_6$) δ 8.03 (s, 3H), 7.63 (d, J = 8.0 Hz, 2H), 7.38 (m, J = 4H), 7.16 (t, J = 8.8 Hz, 2H), 4.85 (m, 1H), 3.84 (dd, J = 11.4, 7.8 Hz, 1H), 2.98-2.85 (m, 2H), 2.79 (dd, J = 15.4, 6.7 Hz, 1H), 2.49 (m, 1H, obscured by DMSO solvent peak), 2.06 (m, 2H), 1.75 (m, 1H), 1.66-1.44 (m, 2H), 1.44-1.15 (m, 2H), 1.20 (d, J = 6.4 Hz, 3H), 0.64 (dd, J = 15.5, 5.9 Hz, 1H) $^{19}$F NMR (DMSO-d$_6$) δ −60.70, −117.22 |
| 115 | — | — | | $^1$H NMR (DMSO-d$_6$) δ 8.36 (s, 3H), 4.85 (ap, J = 6.3 Hz, 1H), 3.87 (dd, J = 11.0, 6.9 Hz, 1H), 2.13 (dt, J = 11.9, 6.6 Hz, 1H), 1.86 (m, 2H), 1.72 (dt, J = 10.8, 6.1 Hz, 1H), 1.65-1.03 (m, 17 H), 1.33 (d, J = 6.4 Hz, 3H), 0.86 (dd, J = 6.6, 2.2 Hz, 6H), 0.70 (dd, J = 14.5, 5.2 Hz, 1H) $^{13}$C NMR (DMSO-d$_6$) δ 170.05, 74.74, 51.20, 49.15, 41.89, 37.49, 36.49, 30.83, 30.35, 29.63, 27.83, 27.60, 27.23, 24.60, 23.89, 22.77, 22.30, 21.17, 18.08 |
| 116 | — | — | ESIMS m/z 332 [M + H]$^+$ | $^1$H NMR (CD$_3$OD) δ 7.31-7.24 (m, 2H), 7.17 (dd, J = 7.6, 5.7 Hz, 3H), 4.86-4.80 (m, 1H), 3.88 (dd, J = 11.0, 7.4 Hz, 1H), 2.92-2.82 (m, 1H), 2.36 (dd, J = 13.7, 11.1 Hz, 1H), 2.26-2.15 (m, 1H), 1.88-1.76 (m, 1H), 1.75-1.45 (m, 7H), 1.40 (d, J = 6.3 Hz, 3H), 1.36-1.23 (m, 2H), 1.16 (ddt, J = 13.5, 11.9, 5.5 Hz, 1H), 0.95 (dd, J = 6.6, 1.2 Hz, 6H), 0.75 (dd, J = 15.5, 7.4 Hz, 1H) |
| 117 | — | — | ESIMS m/z 322 [M + H]$^+$ | $^1$H NMR (CD$_3$OD) δ 7.30-7.18 (m, 2H), 7.09-6.96 (m, 2H), 4.95-4.89 (m, 1H), 3.87 (dd, J = 11.0, 7.3 Hz, 1H), 2.78-2.58 (m, 2H), 2.33-2.17 (m, 1H), 1.96-1.79 (m, 2H), 1.69-1.61 (m, 2H), 1.51-1.32 (m, 5H), 1.23 (d, J = 6.4 Hz, 3H), 1.20-1.10 (m, 1H), 0.92-0.83 (m, 1H), 0.87 (t, J = 7.1 Hz, 3H) |
| 118 | — | — | ESIMS m/z 338 [M + H]$^+$ | $^1$H NMR (DMSO-d$_6$) δ 8.30 (bs, 3H), 7.49-7.35 (m, 4H), 7.30 (dt, J = 8.4, 4.2 Hz, 1H), 7.20 (t, J = 7.3 Hz, 2H), 7.12 (t, J = 7.3 Hz, 1H), 6.87 (d, J = 7.0 Hz, 2H), 5.24 (dd, J = 9.5, 6.4 Hz, 1H), 4.04-3.86 (m, 1H), 2.80 (t, J = 9.7 Hz, 1H), 2.32 (d, J = 11.2 Hz, 1H), 2.28-2.11 (m, 3H), 1.60 (m, 2H), 1.44 (m, 1H), 1.31 (m, 1H), 0.95-0.88 (m, 1H), 0.89 (d, J = 6.3 Hz, 3H) |
| 119 | — | — | ESIMS m/z 290 [M + H]$^+$ | $^1$H NMR (DMSO-d$_6$) δ 8.38 (bs, 3H), 7.37-7.28 (m, 2H), 7.28-7.17 (m, 3H), 5.18 (m, 1H), 3.92 (dd, J = 10.6, 7.4 Hz, 1H), 2.60 (t, J = 9.8 Hz, 1H), 2.19 (m, 1H), 1.90-1.76 (m, 2H), 1.55 (m, 2H), 01.45-0.87 (m, 6H), 0.84 (d, J = 6.3 Hz, 3H), 0.63 (t, J = 7.1 Hz, 3H) |
| 120 | — | — | ESIMS m/z 346 [M + H]$^+$ | $^1$H NMR (CDCl$_3$) δ 8.62 (s, 3H), 7.34-7.10 (m, 5H), 4.83-4.50 (m, 1H), 4.16-3.88 (m, 1H), 2.71-2.41 (m, 3H), 1.86-1.61 (m, 3H), 1.60-1.24 (m, 9H), 1.22-1.09 (m, 3H), 0.95-0.70 (m, 8H) $^{13}$C NMR (CDCl$_3$) δ 170.15, 142.26, 128.39, 128.29, 125.74, 78.06, 52.12, 43.96, 43.06, |

TABLE 2-continued

Analytical Data

| *Cmpd. No. | MP (° C.) | IR (cm⁻¹) | MASS | NMR (¹H, ¹³C or ¹⁹F) |
|---|---|---|---|---|
| 121 | — | — | ESIMS m/z 316 [M + H]⁺ | 41.31, 35.83, 30.88, 30.29, 29.07, 27.74, 27.35, 24.01, 21.81, 19.70, 17.92<br>¹H NMR (CD₃OD) δ 7.52-7.40 (m, 2H), 7.41-7.33 (m, 3H), 5.17-5.07 (m, 1H), 4.05 (dd, J = 11.1, 7.3 Hz, 1H), 2.90 (dd, J = 15.4, 3.8 Hz, 1H), 2.80 (dd, J = 15.4, 7.4 Hz, 1H), 2.52-2.38 (m, 1H), 2.30-2.18 (m, 1H), 2.15-2.01 (m, 1H), 1.97-1.80 (m, 2H), 1.80-1.56 (m, 3H), 1.42 (d, J = 6.4 Hz, 3H), 1.23 (dd, J = 11.5, 8.2 Hz, 1H), 1.14 (dd, J = 15.3, 7.6 Hz, 1H), 0.94-0.78 (m, 1H), 0.69-0.59 (m, 1H), 0.59-0.47 (m, 1H), 0.28-0.17 (m, 1H), 0.07 (tt, J = 8.5, 4.4 Hz, 1H) |
| 122 | — | — | ESIMS m/z 370 [M + H]⁺ | ¹H NMR (CD₃OD) δ 7.54-7.48 (m, 2H), 7.46-7.38 (m, 2H), 7.39-7.28 (m, 3H), 7.28-7.20 (m, 2H), 5.23-5.10 (m, 1H), 4.14-4.01 (m, 1H), 3.18-3.08 (m, 2H), 2.97 (dd, J = 15.7, 7.5 Hz, 1H), 2.71-2.55 (m, 1H), 2.39 (dt, J = 13.6, 6.9 Hz, 1H), 2.34-2.20 (m, 1H), 2.04-1.74 (m, 3H), 1.66 (dtd, J = 14.4, 9.3, 4.4 Hz, 1H), 1.55-1.41 (m, 4H), 0.97 (dd, J = 15.6, 7.7 Hz, 1H) |
| 123 | 227-232 | — | ESIMS m/z 464 [M + H]⁺ | ¹H NMR (CD₃OD) δ 7.29-7.06 (m, 9H), 4.93-4.82 (m, 1H), 3.86 (dd, J = 10.9, 7.2 Hz, 1H), 2.72-2.42 (m, 4H), 2.31-2.17 (m, 1H), 1.98-1.65 (m, 3H), 1.63-1.51 (m, 2H), 1.50-1.16 (m, 8H), 0.96-0.81 (m, 1H)<br>¹⁹F NMR (CD₃OD) δ −55.55 |
| 124 | 215-217 | — | ESIMS m/z 504.4 [M + H]⁺ | ¹H NMR (CDCl₃) δ 8.69 (bs, 3H), 7.53-7.45 (m, 2H), 7.25-7.08 (m, 6H), 4.93-4.81 (m, 1H), 3.98-3.84 (m, 1H), 2.96-2.84 (m, 2H), 2.70 (dd, J = 15.8, 7.4 Hz, 1H), 2.50-2.37 (m, 2H), 2.09-1.97 (m, 1H), 1.80-1.31 (m, 5H), 1.22 (d, J = 6.1 Hz, 3H), 0.83-0.69 (m, 1H) |
| 125 | 196-198 | — | ESIMS m/z 436.4 [M + H]⁺ | ¹H NMR (CDCl₃) δ 8.64 (bs, 3H), 7.32-7.12 (m, 7H), 7.07-6.99 (m, 2H), 4.92-4.79 (m, 1H), 3.97-3.85 (m, 1H), 2.97-2.81 (m, 2H), 2.66 (dd, J = 15.7, 7.6 Hz, 1H), 2.52-2.31 (m, 2H), 2.08-1.94 (m, 1H), 1.81-1.39 (m, 5H), 1.19 (d, J = 6.5 Hz, 3H), 0.79-0.66 (m, 1H) |
| 126 | — | — | ESIMS m/z 380.4 [M + H]⁺ | ¹H NMR (CDCl₃) δ 8.69 (bs, 3H), 7.31-7.22 (m, 4H), 7.22-7.04 (m, 6H), 4.95-4.74 (m, 1H), 3.99-3.80 (m, 1H), 2.75-2.64 (m, 1H), 2.62-2.38 (m, 4H), 1.95-1.22 (m, 10H), 1.18 (d, J = 5.7 Hz, 3H), 0.91-0.78 (m, 1H) |
| 127 | — | — | ESIMS m/z 418 [M + H]⁺ | ¹H NMR (CDCl₃) δ 7.36-7.06 (m, 5H), 5.07 (d, J = 8.3 Hz, 1H), 4.78 (dq, J = 12.4, 6.1 Hz, 1H), 4.15 (dt, J = 10.8, 7.7 Hz, 1H), 2.92-2.75 (m, 1H), 2.30 (dd, J = 13.7, 11.3 Hz, 1H), 2.17 (dt, J = 13.3, 6.5 Hz, 1H), 1.83-1.69 (m, 1H), 1.68-1.12 (m, 10H), 1.43 (s, 9H), 1.34 (d, J = 6.3 Hz, 3H), 1.10-0.97 (m, 1H), 0.93 (t, J = 7.2 Hz, 3H), 0.76-0.67 (m, 1H)<br>¹³C NMR (CDCl₃) δ 173.10, 154.96, 141.16, 128.70, 128.31, 125.85, 79.62, 75.19, 52.48, 45.31, 42.53, 37.88, 33.75, 29.35, 28.34, 27.81, 27.48, 23.50, 19.71, 18.48, 14.04 |
| 128 | — | — | ESIMS m/z 486 [M + H]⁺ | ¹H NMR (CDCl₃) δ 7.53 (d, J = 8.0 Hz, 2H), 7.24 (d, J = 8.0 Hz, 2H), 5.06 (d, J = 8.3 Hz, 1H), 4.79 (dq, J = 9.9, 6.3 Hz, 1H), 4.16 (dt, J = 10.9, 7.7 Hz, 1H), 2.97-2.76 (m, 1H), 2.39 (dd, J = 13.8, 11.3 Hz, 1H), 2.19 (dt, J = 13.5, 6.8 Hz, 1H), 1.85-1.73 (m, 1H), 1.70-1.14 (m, 10H), 1.43 (s, 9H), 1.35 (d, J = 6.3 Hz, 3H), 1.03 (q, J = 11.8 Hz, 1H), 0.94 (t, J = 7.1 Hz, 3H), 0.81-0.68 (m, 1H)<br>¹⁹F NMR (CDCl₃) δ −62.31 |
| 129 | — | — | ESIMS m/z 454 [M + Na]⁺ | ¹H NMR (CDCl₃) δ 7.34-7.14 (m, 5H), 5.10 (d, J = 8.3 Hz, 1H), 4.83 (dq, J = 9.6, 6.4 Hz, 1H), 4.19-4.08 (m, 1H), 2.74 (dd, J = 15.4, 3.2 Hz, 1H), 2.55 (dd, J = 15.5, 7.7 Hz, 1H), 2.29-2.16 (m, 1H), 1.97-1.87 (m, 1H), 1.80-1.69 (m, 1H), 1.55-1.38 (m, 4H), 1.43 (s, 9H), 1.37-1.21 (m, 3H), 1.19 (d, J = 6.4 Hz, 3H), 1.17-1.08 (m, 1H), 1.06-0.96 (m, 1H), 0.91-0.85 (m, 1H), 0.84 (d, 6H) |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| 130 | — | — | ESIMS m/z 474 [M + Na]$^+$ | $^{13}$C NMR (CDCl$_3$) δ 173.10, 154.94, 140.96, 128.82, 128.39, 125.97, 79.66, 76.05, 52.62, 47.51, 42.18, 37.47, 36.75, 33.78, 29.29, 28.35, 28.23, 23.04, 22.31, 20.79, 18.48 $^1$H NMR (CDCl$_3$) δ 7.37-7.01 (m, 10H), 5.06 (d, J = 8.3 Hz, 1H), 4.89 (dq, J = 9.6, 6.4 Hz, 1H), 4.15 (dt, J = 11.8, 7.9 Hz, 1H), 3.01-2.87 (m, 2H), 2.70 (dd, J = 15.6, 7.5 Hz, 1H), 2.39 (dd, J = 13.8, 11.6 Hz, 1H), 2.18 (dt, J = 13.5, 6.8 Hz, 1H), 2.08 (tdd, J = 9.9, 7.4, 3.1 Hz, 1H), 1.73 (dtd, J = 14.7, 7.1, 3.3 Hz, 1H), 1.67-1.47 (m, 2H), 1.42 (s, 9H), 1.41-1.33 (m, 1H), 1.26 (d, J = 6.3 Hz, 3H), 1.02 (q, J = 11.9 Hz, 1H), 0.75 (ddd, J = 16.1, 8.9, 2.9 Hz, 1H) |
| 131 | — | — | ESIMS m/z 452 [M + Na]$^+$ | $^{13}$C NMR (CDCl$_3$) δ 173.01, 154.96, 140.78, 140.54, 128.90, 128.71, 128.57, 128.32, 126.24, 125.94, 79.70, 75.84, 52.55, 46.86, 44.13, 37.84, 37.27, 33.78, 28.37, 27.48, 20.79, 18.66 $^1$H NMR (CDCl$_3$) δ 7.31-7.12 (m, 5H), 5.12 (d, J = 8.2 Hz, 1H), 4.91 (dq, J = 8.8, 6.3 Hz, 1H), 4.14 (ddd, J = 11.1, 8.3, 6.6 Hz, 1H), 2.83 (dd, J = 14.2, 3.6 Hz, 1H), 2.57 (dd, J = 14.2, 11.2 Hz, 1H), 2.18-1.93 (m, 3H), 1.84-1.47 (m, 10H), 1.43 (s, 9H), 1.38 (d, J = 6.4 Hz, 3H), 1.34-1.25 (m, 2H), 1.12-1.00 (m, 1H), 0.81-0.72 (m, 1H) |
| 132 | — | — | ESIMS m/z 352 [M − Boc]$^+$ | $^{13}$C NMR (CDCl$_3$) δ 173.05, 154.97, 141.05, 128.61, 128.26, 125.87, 79.60, 74.50, 53.00, 48.49, 42.53, 40.09, 39.44, 33.82, 29.42, 28.65, 28.35, 27.77, 25.24, 24.43, 21.44, 19.52 $^1$H NMR (CDCl$_3$) δ 7.26-7.21 (m, 2H), 7.10-7.04 (m, 2H), 5.03 (d, J = 8.4 Hz, 1H), 4.80-4.64 (m, 1H), 4.14 (dt, J = 11.0, 7.7 Hz, 1H), 2.91-2.77 (m, 1H), 2.27 (dd, J = 13.9, 11.3 Hz, 1H), 2.23-2.07 (m, 1H), 1.79-1.64 (m, 1H), 1.58-1.47 (m, 3H), 1.43 (s, 9H), 1.39-1.25 (m, 2H), 1.35 (d, J = 6.4 Hz, 3H), 1.15-0.98 (m, 2H), 0.96 (t, J = 6.6 Hz, 6H), 0.91-0.69 (m, 2H) |
| 133 | — | — | ESIMS m/z 508 [M + Na]$^+$ | $^{13}$C NMR (CDCl$_3$) δ 173.07, 154.96, 139.52, 131.59, 129.99, 128.43, 79.73, 76.60, 52.46, 45.82, 43.72, 41.51, 36.80, 33.78, 28.34, 27.57, 27.31, 24.07, 21.97, 19.75, 18.42 $^1$H NMR (CDCl$_3$) δ 7.59-7.47 (m, 2H), 7.26-7.17 (m, 2H), 5.03 (d, J = 8.4 Hz, 1H), 4.79-4.65 (m, 1H), 4.15 (dt, J = 11.0, 7.8 Hz, 1H), 2.91 (d, J = 13.7 Hz, 1H), 2.37 (dd, J = 13.8, 10.9 Hz, 1H), 2.22-2.14 (m, 1H), 1.81-1.64 (m, 1H), 1.57-1.48 (m, 3H), 1.43 (s, 9H), 1.41-1.24 (m, 3H), 1.37 (d, J = 6.4 Hz, 3H), 1.17-1.00 (m, 2H), 0.97 (t, J = 6.6 Hz, 6H), 0.77 (dd, J = 15.6, 7.9 Hz, 1H) $^{19}$F NMR (CDCl$_3$) δ −62.30 |
| 134 | — | — | ESIMS m/z 420 [M − Boc]$^+$ | $^1$H NMR (CDCl$_3$) δ 7.53-7.10 (m, 9H), 5.03 (d, J = 8.3 Hz, 1H), 4.90 (dt, J = 12.5, 6.4 Hz, 1H), 4.16 (dt, J = 11.1, 7.7 Hz, 1H), 3.00-2.88 (m, 2H), 2.76 (dd, J = 15.6, 7.3 Hz, 1H), 2.52-2.39 (m, 1H), 2.14-2.04 (m, 1H), 1.81-1.70 (m, 1H), 1.66-1.50 (m, 2H), 1.43 (s, 9H), 1.41-1.23 (m, 2H), 1.30 (d, J = 6.3 Hz, 3H), 1.08-0.97 (m, 1H), 0.77 (dd, J = 15.3, 7.9 Hz, 1H) $^{19}$F NMR (CDCl$_3$) δ −62.33 |
| 135 | — | (Neat) 3382, 2938, 1713, 1496, 1367, 1170 | ESIMS m/z 488.4 [M + Na]$^+$ | $^1$H NMR (CDCl$_3$) δ 7.34-7.24 (m, 4H), 7.23-7.10 (m, 6H), 5.05 (d, J = 8.4 Hz, 1H), 4.94-4.84 (m, 1H), 4.23-4.12 (m, 1H), 2.88-2.69 (m, 2H), 2.57-2.46 (m, 1H), 2.32 (dd, J = 13.8, 11.1 Hz, 1H), 2.25-2.13 (m, 1H), 1.93-1.67 (m, 4H), 1.63-1.42 (m, 3H), 1.46 (d, J = 6.5 Hz, 3H), 1.44 (s, 9H), 1.13-0.97 (m, 1H), 0.83-0.71 (m, 1H) |
| 136 | — | (Neat) 3436, 2936, 1710, 1493, 1367, | ESIMS m/z 508.3 [M + Na]$^+$ | $^1$H NMR (CDCl$_3$) δ 7.35-7.28 (m, 2H), 7.27-7.17 (m, 5H), 7.02-6.96 (m, 2H), 5.04 (d, J = 8.3 Hz, 1H), 4.95-4.83 (m, 1H), 4.21-4.08 (m, 1H), 2.93 (dd, J = 15.6, 3.3 Hz, 1H), 2.90-2.81 (m, 1H), 2.72 (dd, J = 15.6, 7.4 Hz, 1H), 2.36 (dd, J = 13.9, 11.7 Hz, 1H), 2.24-2.13 (m, 1H), |

TABLE 2-continued

Analytical Data

| *Cmpd. No. | MP (° C.) | IR (cm⁻¹) | MASS | NMR (¹H, ¹³C or ¹⁹F) |
|---|---|---|---|---|
| | | 1164 | | 2.12-2.01 (m, 1H), 1.75-1.32 (m, 4H), 1.43 (s, 9H), 1.28 (d, J = 6.4 Hz, 3H), 1.09-0.96 (m, 1H), 0.82-0.70 (m, 1H) |
| 137 | — | — | ESIMS m/z 440 [M + Na]⁺ | ¹H NMR (CDCl₃) δ 7.31-7.24 (m, 2H), 7.22-7.11 (m, 3H), 5.04 (d, J = 8.4 Hz, 1H), 4.78-4.66 (m, 1H), 4.15 (dt, J = 10.9, 7.7 Hz, 1H), 2.88 (d, J = 13.7 Hz, 1H), 2.29 (dd, J = 13.8, 11.0 Hz, 1H), 2.18 (dt, J = 13.5, 6.7 Hz, 1H), 1.79-1.67 (m, 1H), 1.62-1.47 (m, 4H), 1.43 (s, 9H), 1.40-1.31 (m, 5H), 1.13 (dd, J = 14.6, 9.9 Hz, 1H), 1.02-0.93 (m, 7H), 0.75 (dd, J = 15.4, 7.6 Hz, 1H) <br> ¹³C NMR (CDCl₃) δ 173.07, 154.91, 141.05, 128.63, 128.25, 125.83, 86.59, 79.63, 76.65, 52.45, 45.84, 43.70, 41.48, 37.36, 33.79, 28.30, 27.56, 27.31, 24.07, 21.92, 19.74, 18.41 |
| 138 | — | — | ESIMS m/z 465 [M + H]⁺ | ¹H NMR (CDCl₃) δ 7.26-7.21 (m, 2H), 7.16-7.06 (m, 2H), 5.07 (d, J = 8.2 Hz, 1H), 4.91 (dq, J = 8.7, 6.3 Hz, 1H), 4.14 (dt, J = 11.1, 7.4 Hz, 1H), 2.89-2.73 (m, 1H), 2.56 (dd, J = 14.2, 11.2 Hz, 1H), 2.17 (s, 3H), 2.16-2.08 (m, 1H), 2.07-1.98 (m, 1H), 1.99-1.87 (m, 1H), 1.79 (ddt, J = 10.0, 7.1, 3.9 Hz, 1H), 1.73-1.47 (m, 9H), 1.43 (s, 9H), 1.38 (d, J = 6.3 Hz, 3H), 1.35-1.23 (m, 2H), 1.06 (q, J = 11.7 Hz, 1H), 0.78 (dd, J = 14.5, 6.6 Hz, 1H) |
| 139 | — | (Neat) 3366, 2949, 1713, 1497, 1366, 1166 | ESIMS m/z 446.4 [M + H]⁺ | ¹H NMR (CDCl₃) δ 7.32-7.26 (m, 2H), 7.23-7.12 (m, 3H), 5.08 (d, J = 8.3 Hz, 1H), 4.91-4.79 (m, 1H), 4.20-4.09 (m, 1H), 2.72-2.60 (m, 1H), 2.51-2.39 (m, 1H), 2.27-2.16 (m, 1H), 1.83-1.62 (m, 3H), 1.61-1.31 (m, 6H), 1.44 (s, 9H), 1.41 (d, J = 6.3 Hz, 3H), 1.30-1.00 (m, 4H), 0.91-0.84 (m, 6H), 0.86-0.79 (m, 1H) |
| 140 | — | (Neat) 3440, 2930, 1711, 1497, 1366, 1162 | ESIMS m/z 404.4 [M + H]⁺ | ¹H NMR (CDCl₃) δ 7.32-7.25 (m, 2H), 7.22-7.16 (m, 3H), 5.07 (d, J = 8.2 Hz, 1H), 4.89-4.77 (m, 1H), 4.20-4.07 (m, 1H), 2.81-2.71 (m, 1H), 2.54 (dd, J = 15.5, 7.8 Hz, 1H), 2.29-2.17 (m, 1H), 1.96-1.84 (m, 1H), 1.81-1.68 (m, 1H), 1.58-1.47 (m, 2H), 1.46-1.28 (m, 5H), 1.43 (s, 9H), 1.18 (d, J = 6.4 Hz, 3H), 1.18-1.06 (m, 2H), 0.84 (t, J = 7.0 Hz, 3H) |
| 141 | — | — | ESIMS m/z 516 [M + Na]⁺ | ¹H NMR (CDCl₃) δ 7.27 (m, 4H), 7.17 (m, 4H), 7.08 (ad, J = 7.0 Hz, 2H), 5.10 (d, J = 8.0 Hz, 1H), 4.84 (m, 1H), 4.14 (q, J = 8.0 Hz, 1H), 2.66-2.50 (m, 3H), 2.46-2.34 (m, 1H), 2.20 (dd, J = 12.5, 6.1 Hz, 1H), 1.83-1.33 (m, 10H), 1.44 (s, 9H), 1.40 (d, J = 6.4 Hz, 3H), 1.26-1.03 (m, 2H), 0.86 (bd, J = 15.4 Hz, 1H) <br> ¹³C NMR (CDCl₃) δ 173.21, 154.99, 142.34, 142.27, 128.48, 128.36, 128.34, 128.20, 125.95, 125.77, 79.72, 75.18, 52.58, 45.67, 40.04, 35.94, 33.75, 32.38, 32.14, 30.92, 29.14, 28.38, 28.02, 19.81, 18.32 |
| 142 | — | — | ESIMS m/z 560 [M + Na]⁺ | ¹H NMR (CDCl₃) δ 7.50 (d, J = 8.0 Hz, 2H), 7.24-7.13 (m, 4H), 7.02 (t, J = 8.6 Hz, 2H), 5.03 (d, J = 8.2 Hz, 1H), 4.89 (dq, J = 12.7, 6.3 Hz, 1H), 4.20-4.10 (m, 1H), 2.91 (ad, J = 15.1 Hz, 2H), 2.72 (dd, J = 15.7, 7.4 Hz, 1H), 2.47 (dd, J = 13.7, 11.9 Hz, 1H), 2.19 (dt, J = 13.4, 6.9 Hz, 1H), 2.10-1.99 (m, 1H), 1.74 (bt, J = 9.8 Hz, 1H), 1.67-1.55 (m, 1H), 1.55-1.29 (m, 2H), 1.43 (s, 9H), 1.28 (d, J = 6.4 Hz, 3H) 1.03 (q, J = 12.2 Hz, 1H), 0.78 (dd, J = 13.4, 5.8 Hz, 1H) <br> ¹³C NMR (CDCl₃) δ 172.93, 161.44 (d, J = 243 Hz), 154.93, 144.75, 135.82 (d, J = 4 Hz), 130.13 (d, J = 8 Hz), 128.9, 128.43 (q, J = 32 Hz), 125.30 (q, J = 3 Hz), 124.23 (q, J = 270 Hz), 115.46 (d, J = 21 Hz), 79.82, 75.46, 52.48, 46.92, 43.75, 37.69, 36.44, 33.64, 28.32, 27.39, 20.73, 18.62 <br> ¹⁹F NMR (CDCl₃) δ -62.34, -116.61 |
| 143 | — | | ESIMS m/z 410 | ¹H NMR (CDCl₃) δ 5.11 (d, J = 8.0 Hz, 1H), 5.00-4.89 (m, 1H), 4.12 (m, 1H), 2.19 (dt, J = |

TABLE 2-continued

Analytical Data

| *Cmpd. No. | MP (° C.) | IR (cm$^{-1}$) | MASS | NMR ($^1$H, $^{13}$C or $^{19}$F) |
|---|---|---|---|---|
| | | | [M + H]$^+$ | 12.7, 5.9 Hz, 1H), 1.95-1.01 (m, 20H), 1.44 (s, 9H), 1.33 (d, J = 6.4 Hz, 3H), 0.87 (dd, J = 6.6, 3.3 Hz, 6H), 0.85-0.69 (m, 1H) $^{13}$C NMR (CDCl$_3$) δ 173.12, 154.98, 79.63, 74.67, 53.10, 49.70, 42.51, 38.36, 37.16, 34.02, 31.41, 30.00, 28.43, 28.35, 28.27, 27.82, 25.07, 24.29, 22.94, 22.48, 21.45, 19.05 |
| 144 | — | — | ESIMS m/z 432 [M + H]$^+$ | $^1$H NMR (CDCl$_3$) δ 7.35-7.04 (m, 5H), 5.03 (d, J = 8.4 Hz, 1H), 4.77 (dt, J = 9.6, 6.2 Hz, 1H), 4.15 (dt, J = 11.1, 7.8 Hz, 1H), 2.93-2.72 (m, 1H), 2.31 (dd, J = 13.7, 11.3 Hz, 1H), 2.24-2.14 (m, 1H), 1.77 (td, J = 13.7, 10.9, 3.0 Hz, 1H), 1.70-1.38 (m, 7H), 1.43 (s, 9H), 1.34 (d, J = 6.3 Hz, 3H), 1.28 (ddd, J = 12.0, 7.2, 5.2 Hz, 1H), 1.19-0.97 (m, 2H), 0.92 (d, J = 6.6 Hz, 6H), 0.70 (dd, J = 14.7, 6.9 Hz, 1H) $^{13}$C NMR (CDCl$_3$) δ 173.10, 154.97, 141.18, 128.71, 128.32, 125.86, 79.68, 75.10, 52.47, 45.29, 42.31, 37.90, 34.47, 33.78, 28.85, 28.33, 27.49, 27.18, 22.73, 22.45, 19.70, 18.47 |
| 145 | — | — | ESIMS m/z 422 [M + H]$^+$ | $^1$H NMR (CDCl$_3$) δ 7.18-7.09 (m, 2H), 7.04-6.89 (m, 2H), 5.07 (d, J = 8.3 Hz, 1H), 4.90-4.75 (m, 1H), 4.13 (dt, J = 11.0, 7.5 Hz, 1H), 2.77-2.66 (m, 1H), 2.52 (dd, J = 15.5, 7.8 Hz, 1H), 2.29-2.18 (m, 1H), 1.93-1.78 (m, 2H), 1.80-1.63 (m, 2H), 1.55-1.26 (m, 4H), 1.43 (s, 9H), 1.17 (d, J = 6.4 Hz, 3H), 1.12 (dd, J = 13.5, 7.5 Hz, 2H), 0.88-0.81 (m, 1H), 0.85 (t, J = 7.1 Hz, 3H) $^{19}$F NMR (CDCl$_3$) δ −117.37 |
| 146 | — | — | ESIMS m/z 460 [M + Na]$^+$ | $^1$H NMR (CDCl$_3$) δ 7.35 (at, J = 7.4 Hz, 2H), 7.26 (at, J = 7.3 Hz, 1H), 7.23-7.14 (m, 4H), 7.11 (at, J = 7.2 Hz, 1H), 6.91-6.84 (m, 2H), 5.16 (dd, J = 9.6, 6.4 Hz, 1H), 5.07 (d, J = 8.2 Hz, 1H), 4.31-4.17 (m, 1H), 2.74 (t, J = 9.9 Hz, 1H), 2.51 (d, J = 12.7 Hz, 1H), 2.32-2.17 (m, 2H), 2.17-2.06 (m, 1H), 1.77-1.47 (m, 3H), 1.44 (s, 9H), 1.33-1.23 (m, 1H), 1.11 (q, J = 11.7 Hz, 1H), 0.96 (dd, J = 6.4, 5.0 Hz, 3H) $^{13}$C NMR (CDCl$_3$) δ 173.26, 154.98, 142.22, 140.81, 128.76, 128.58, 128.16, 127.00, 125.78, 79.77, 75.25, 55.16, 52.48, 46.73, 37.54, 33.88, 28.35, 27.23, 20.66, 18.11 |
| 147 | — | — | ESIMS m/z 412 [M + Na]$^+$ | $^1$H NMR (CDCl$_3$) δ 7.34-7.24 (m, 2H), 7.21 (ddd, J = 7.3, 5.1, 1.2 Hz, 1H), 7.13-7.07 (m, 2H), 5.18-5.06 (m, 2H), 4.22 (m, 1H), 2.57 (t, J = 9.9 Hz, 1H), 2.28 (dt, J = 13.5, 6.7 Hz, 1H), 1.82 (m, 2H), 1.67-1.49 (m, 2H), 1.45 (s, 9H), 1.38-0.83 (m, 6H), 0.89 (d, J = 6.4 Hz, 3H), 0.67 (t, J = 7.2 Hz, 3H) $^{13}$C NMR (CDCl$_3$) δ 173.37, 154.98, 142.62, 128.94, 128.47, 126.65, 79.73, 75.49, 55.51, 52.56, 43.40, 33.89, 33.46, 28.35, 27.96, 20.57, 20.04, 18.04, 13.99 |
| 148 | — | — | ESIMS m/z 468 [M + Na]$^+$ | $^1$H NMR (CDCl$_3$) δ 7.31-7.23 (m, 2H), 7.16 (td, J = 6.4, 1.7 Hz, 3H), 5.10 (d, J = 8.3 Hz, 1H), 4.66 (dq, J = 9.5, 6.4 Hz, 1H), 4.11 (dt, J = 11.2, 7.5 Hz, 1H), 2.68-2.47 (m, 2H), 2.25-2.16 (m, 1H), 1.78-1.63 (m, 2H), 1.65-1.51 (m, 1H), 1.43 (s, 9H), 1.48-1.32 (m, 5H), 1.29 (d, J = 6.4 Hz, 3H), 1.22-1.06 (m, 4H), 0.90-0.78 (m, 8H) $^{13}$C NMR (CDCl$_3$) δ 173.19, 154.96, 142.39, 128.38, 128.26, 125.71, 79.62, 76.87, 52.58, 44.13, 43.16, 41.39, 35.93, 33.83, 30.41, 29.24, 28.36, 27.91, 27.40, 24.02, 21.87, 19.78, 18.29 |
| 149 | — | — | ESIMS m/z 586 [M + Na]$^+$ | $^1$H NMR (CDCl$_3$) δ 7.31-7.23 (m, 2H), 7.21-7.09 (m, 7H), 5.08 (d, J = 8.3 Hz, 1H), 4.82 (dq, J = 9.7, 6.4 Hz, 1H), 4.13 (dt, J = 10.9, 7.6 Hz, 1H), 2.67 (dd, J = 15.5, 3.5 Hz, 1H), 2.62-2.44 (m, 3H), 2.29-2.15 (m, 1H), 1.87 (ddq, J = 16.0, 8.3, 4.3, 3.4 Hz, 1H), 1.81-1.65 (m, 2H), 1.43 (s, 15H), 1.25-1.06 (m, 4H), 0.95-0.80 (m, 1H) |

TABLE 2-continued

Analytical Data

| *Cmpd. No. | MP (° C.) | IR (cm⁻¹) | MASS | NMR ($^1$H, $^{13}$C or $^{19}$F) |
|---|---|---|---|---|
| | | | | $^{13}$C NMR (CDCl$_3$) δ 173.01, 154.89, 147.46 (q, J = 1.6 Hz), 142.24, 139.51, 129.98, 128.27, 125.77, 120.89, 120.46 (q, J = 256.9 Hz), 79.70, 75.57, 52.55, 47.47, 41.65, 36.65, 35.99, 33.70, 31.15, 29.25, 28.31, 27.84, 20.74, 18.42<br>$^{19}$F NMR (CDCl$_3$) δ −57.91 |
| 150 | — | — | ESIMS m/z 438 [M + Na]$^+$ | $^1$H NMR (CDCl$_3$) δ 7.28-7.21 (m, 2H), 7.19-7.09 (m, 3H), 5.11 (d, J = 8.2 Hz, 1H), 4.83 (dq, J = 9.8, 6.5 Hz, 1H), 4.12 (dt, J = 11.0, 7.7 Hz, 1H), 2.67 (dd, J = 15.6, 3.1 Hz, 1H), 2.49 (dd, J = 15.5, 7.7 Hz, 1H), 2.22 (ddd, J = 12.6, 9.9, 5.2 Hz, 1H), 2.00-1.80 (m, 2H), 1.61-1.43 (m, 4H), 1.41 (s, 9H), 1.16 (d, J = 6.4 Hz, 3H), 1.14-1.08 (m, 1H), 1.05-0.95 (m, 1H), 0.94-0.86 (m, 1H), 0.62 (dtt, J = 9.9, 8.0, 4.9 Hz, 1H), 0.50-0.37 (m, 1H), 0.31 (tt, J = 8.9, 4.5 Hz, 1H), 0.01 (td, J = 8.9, 8.4, 4.3 Hz, 1H), −0.16 (dq, J = 9.5, 4.9 Hz, 1H)<br>$^{13}$C NMR (CDCl$_3$) δ 173.04, 154.94, 140.80, 128.80, 128.38, 125.99, 79.62, 76.00, 52.60, 46.78, 42.58, 37.28, 36.58, 33.88, 28.35, 20.76, 18.84, 9.17, 5.66, 3.72 |
| 151 | — | — | ESIMS m/z 470 [M + H]$^+$ | $^1$H NMR (CDCl$_3$) δ 7.30-7.14 (m, 5H), 7.11-7.05 (m, 2H), 7.05-6.95 (m, 2H), 5.06 (d, J = 8.3 Hz, 1H), 4.87 (dq, J = 9.5, 6.4 Hz, 1H), 4.15 (dt, J = 11.2, 7.8 Hz, 1H), 2.92 (ddd, J = 13.2, 5.9, 3.1 Hz, 2H), 2.68 (dd, J = 15.7, 7.5 Hz, 1H), 2.51-2.33 (m, 1H), 2.23-2.16 (m, 1H), 2.03 (tdd, J = 9.8, 7.5, 3.0 Hz, 1H), 1.79-1.66 (m, 1H), 1.66-1.47 (m, 2H), 1.45-1.36 (m, 1H), 1.42 (s, 9H), 1.25 (d, J = 6.4 Hz, 3H), 1.02 (q, J = 11.8 Hz, 1H), 0.84-0.68 (m, 1H)<br>$^{19}$F NMR (CDCl$_3$) δ −116.84 |
| 152 | 65-67 | (Neat) 3442, 2939, 1711, 1509, 1326, 1259 | HRMS-ESI (m/z) [M]$^+$ calcd for C$_{30}$H$_{35}$F$_6$NO$_5$, 603.2419; found, 603.2425 | $^1$H NMR (CDCl$_3$) δ 7.55-7.47 (m, 2H), 7.29-7.25 (m, 2H), 7.21-7.13 (m, 4H), 5.02 (d, J = 8.4 Hz, 1H), 4.95-4.85 (m, 1H), 4.22-4.11 (m, 1H), 2.99-2.86 (m, 2H), 2.75 (dd, J = 15.8, 7.5 Hz, 1H), 2.49 (dd, J = 13.9, 11.6 Hz, 1H), 2.26-2.14 (m, 1H), 2.14-2.03 (m, 1H), 1.80-1.69 (m, 2H), 1.68-1.56 (m, 1H), 1.56-1.30 (m, 2H), 1.43 (s, 9H), 1.27 (d, J = 6.4 Hz, 2H), 1.11-0.97 (m, 1H), 0.85-0.72 (m, 1H) |
| 153 | — | (Neat) 3441, 2953, 1713, 1509, 1367, 1259 | HRMS-ESI (m/z) [M]$^+$ calcd for C$_{29}$H$_{36}$F$_3$NO$_5$, 535.2546; found, 535.2542 | $^1$H NMR (CDCl$_3$) δ 7.30-7.22 (m, 4H), 7.22-7.14 (m, 3H), 7.10-7.03 (m, 2H), 5.02 (d, J = 8.2 Hz, 1H), 4.94-4.83 (m, 1H), 4.21-4.09 (m, 1H), 3.01-2.86 (m, 2H), 2.71 (dd, J = 15.8, 7.6 Hz, 1H), 2.42 (dd, J = 13.8, 11.6 Hz, 1H), 2.25-2.14 (m, 1H), 2.13-2.01 (m, 1H), 1.78-1.67 (m, 1H), 1.66-1.36 (m, 3H), 1.43 (s, 9H), 1.25 (d, J = 7.3 Hz, 3H), 1.10-0.97 (m, 1H), 0.83-0.71 (m, 1H)<br>$^{19}$F NMR (CDCl$_3$) δ −57.93 |
| 154 | — | (Neat) 3350, 2932, 1712, 1496, 1366, 1169 | HRMS-ESI (m/z) [M]$^+$ calcd for C$_{30}$H$_{41}$NO$_4$, 479.3036; found, 479.3037 | $^1$H NMR (CDCl$_3$) δ 7.31-7.23 (m, 4H), 7.22-7.10 (m, 6H), 5.06 (d, J = 8.2 Hz, 1H), 4.90-4.76 (m, 1H), 4.19-4.03 (m, 1H), 2.71 (dd, J = 15.4, 3.3 Hz, 1H), 2.63-2.42 (m, 3H), 2.30-2.12 (m, 1H), 1.97-1.82 (m, 1H), 1.82-1.61 (m, 2H), 1.59-1.25 (m, 6H), 1.43 (s, 9H), 1.20 (d, J = 6.4 Hz, 3H), 1.19-1.04 (m, 1H), 0.92-0.79 (m, 1H) |

*Cmpd. No.—Compound Number
*$^1$H NMR were run at 400 MHz unless noted otherwise.
*$^{13}$C NMR were run at 101 MHz unless noted otherwise.
*$^{19}$F NMR were run at 376 MHz unless noted otherwise.

TABLE 3

Biological Testing Rating Scale Rating Table for Fungal Pathogens

| % Control | Rating |
|---|---|
| >70 | A |
| ≤70 | B |
| Not Tested | C |

TABLE 4

Biological Activity - PUCCRT and SEPTTR Disease Control in High and Low Volume Applications

| Cmpd. No. | Low Volume activity at 121.5 g/H PUCCRT 1DP* | 3DC* | SEPTTR 1DP* | 3DC* | High Volume activity at 100 ppm PUCCRT 1DP* | 3DC* | SEPTTR 1DP* | 3DC* |
|---|---|---|---|---|---|---|---|---|
| 1 | A | B | A | A | A | A | A | A |
| 2 | A | B | A | A | A | A | A | A |
| 3 | A | B | A | A | C | C | C | C |
| 4 | A | B | A | A | C | C | C | C |
| 5 | A | A | A | A | C | C | C | C |
| 6 | A | A | A | A | C | C | C | C |
| 7 | A | A | A | A | C | C | C | C |
| 8 | A | B | A | A | C | C | C | C |
| 9 | A | B | A | A | C | C | C | C |
| 10 | A | A | A | A | C | C | C | C |
| 12 | A | B | A | A | C | C | C | C |
| 13 | A | B | A | A | C | C | C | C |
| 14 | A | B | A | A | C | C | C | C |
| 15 | A | B | A | A | C | C | C | C |
| 16 | A | A | A | A | C | C | C | C |
| 17 | A | B | A | A | C | C | C | C |
| 18 | B | B | A | A | C | C | C | C |
| 19 | A | B | A | A | C | C | C | C |
| 20 | A | A | A | B | C | C | C | C |
| 21 | A | B | A | B | C | C | C | C |
| 22 | A | B | A | B | C | C | C | C |
| 23 | A | B | A | B | C | C | C | C |
| 24 | B | B | A | B | C | C | C | C |
| 25 | B | B | B | B | C | C | C | C |
| 26 | A | B | A | B | C | C | C | C |
| 27 | A | B | A | B | C | C | C | C |
| 28 | A | B | A | A | C | C | C | C |
| 29 | A | B | A | A | C | C | C | C |
| 30 | B | B | A | A | C | C | C | C |
| 31 | A | B | A | A | C | C | C | C |
| 32 | A | B | A | B | C | C | C | C |
| 33 | B | B | A | B | C | C | C | C |
| 34 | A | B | A | A | C | C | C | C |
| 35 | A | B | A | A | C | C | C | C |
| 36 | A | B | A | A | C | C | C | C |
| 37 | A | A | A | A | C | C | C | C |
| 38 | A | A | A | A | C | C | C | C |
| 39 | B | B | A | A | C | C | C | C |
| 40 | A | B | A | B | C | C | C | C |
| 41 | B | B | B | B | C | C | C | C |
| 42 | A | B | A | A | C | C | C | C |
| 43 | A | B | A | A | C | C | C | C |
| 44 | A | B | A | A | C | C | C | C |
| 45 | A | B | A | A | C | C | C | C |
| 46 | A | A | A | A | C | C | C | C |
| 47 | A | B | A | A | C | C | C | C |
| 48 | A | A | A | A | C | C | C | C |
| 49 | B | B | A | A | C | C | C | C |
| 50 | A | B | A | A | C | C | C | C |
| 51 | A | B | A | A | C | C | C | C |
| 52 | A | B | A | A | C | C | C | C |
| 53 | A | B | A | A | C | C | C | C |
| 54 | A | A | A | A | C | C | C | C |
| 55 | A | A | A | A | C | C | C | C |
| 56 | A | B | A | B | C | C | C | C |
| 57 | B | B | B | B | C | C | C | C |
| 58 | B | B | B | B | C | C | C | C |
| 59 | A | B | A | B | C | C | C | C |
| 60 | A | A | A | A | C | C | C | C |
| 61 | A | A | A | A | C | C | C | C |
| 62 | A | B | A | A | C | C | C | C |
| 63 | A | B | A | A | C | C | C | C |
| 64 | A | B | A | A | C | C | C | C |
| 65 | B | B | B | B | C | C | C | C |
| 66 | B | B | B | B | C | C | C | C |
| 67 | B | B | B | B | C | C | C | C |
| 68 | B | B | B | B | C | C | C | C |
| 69 | B | B | A | B | C | C | C | C |
| 70 | A | B | A | A | C | C | C | C |
| 71 | C | C | C | C | A | A | A | B |
| 72 | C | C | C | C | A | B | A | B |
| 73 | C | C | C | C | A | B | A | A |
| 74 | C | C | C | C | A | A | A | A |
| 75 | C | C | C | C | A | B | A | A |
| 76 | C | C | C | C | A | B | A | A |
| 77 | C | C | C | C | C | C | C | C |
| 78 | C | C | C | C | A | B | A | A |
| 79 | C | C | C | C | A | B | A | B |
| 80 | C | C | C | C | A | B | A | B |
| 81 | C | C | C | C | A | B | A | B |
| 82 | C | C | C | C | A | A | B | A |
| 83 | C | C | C | C | A | B | A | B |
| 84 | C | C | C | C | A | B | A | A |
| 85 | C | C | C | C | A | B | A | B |
| 86 | C | C | C | C | A | B | B | B |
| 87 | C | C | C | C | A | B | A | B |
| 88 | C | C | C | C | A | B | B | A |
| 89 | C | C | C | C | C | C | C | C |
| 90 | C | C | C | C | A | A | A | A |
| 91 | C | C | C | C | A | B | A | A |
| 92 | C | C | C | C | A | B | A | B |
| 93 | C | C | C | C | B | B | B | B |
| 94 | A | B | A | A | C | C | C | C |
| 95 | A | B | A | A | C | C | C | C |
| 96 | C | C | C | C | B | B | B | B |
| 97 | C | C | C | C | A | B | A | B |
| 98 | C | C | C | C | A | B | A | A |

*Cmpd. No.—Compound Number
*PUCCRT—Wheat Brown Rust (*Puccinia triticina*)
*SEPTTR—Wheat Leaf Blotch (*Septoria tritici*)
*1DP—1 Day Protectant
*3DC—3 Day Curative
*g/H—Grams Per Hectare
*ppm—Parts Per Million

TABLE 5

Biological Activity - Disease Control at 100 ppm

| *Cmpd. No. | ALTESO* | CERCBE* | COLLLA* 1DP* | ERYSCI* | ERYSGH* |
|---|---|---|---|---|---|
| 3 | A | B | A | A | A |

*Cmpd. No. - Compound Number
*ALTESO - Tomato Early Blight (*Alternaria solani*)
*CERCBE - Leaf Spot of Sugar Beets (*Cercospora beticola*)
*COLLLA - Cucumber Anthracnose (*Glomerella lagenarium*; Anamorph: *Colletotricum lagenarium*)
*ERYSCI - Powdery Mildew of Cucumber (*Erysiphe cichoracearum*)
*ERYSGH - Barley Powdery Mildew (*Blumeria graminis* f.sp. *hordei*; Synonym: *Erysiphe graminis* f.sp. *hordei*)
1DP - 1 Day Protectant

TABLE 6

| | Biological Activity - Disease Control at 100 ppm | | | |
|---|---|---|---|---|
| *Cmpd. No. | LEPTNO* | RHYNSE* 1DP | UNCINE* | VENTIN* |
| 3 | A | B | A | A |

*Cmpd. No. - Compound Number
*LEPTNO - Wheat Glume Blotch (*Leptosphaeria nodorum*)
*RHYNSE - Barley Scald (*Rhyncosporium secalis*)
*UNCINE - Grape Powdery Mildew (*Uncinula necator*)
*VENTIN - Apple Scab (*Venturia inaequalis*)
*1DP - 1 Day Protectant

TABLE 7

| | Biological Activity - Disease Control at 25 ppm | |
|---|---|---|
| *Cmpd. | PHAKPA* | |
| No. | 1DP* | 3DC* |
| 3 | B | B |

*Cmpd. No. - Compound Number
*PHAKPA - Asian Soybean Rust (*Phakopsora pachyrhizi*)
*1DP - 1 Day Protectant
*3DC - 3 Day Curative

What is claimed is:

1. A compound of Formula I

[Structure I: a lactone ring with substituents X, Y on N; CH$_3$, R$_1$, R$_2$ substituents]

wherein
X is hydrogen or C(O)R$_3$;
Y is hydrogen, C(O)R$_3$, or Q;
Q is

[Structure showing a pyridine ring with H$_3$C—O, R$_4$—O substituents and C(O) linker]

R$_1$ and R$_2$ are independently selected from the group consisting of hydrogen, alkyl, alkenyl, and aryl, each optionally substituted with 0, 1 or multiple R$_6$;
R$_3$ alkoxy or benzyloxy, each optionally substituted with 0, 1, or multiple R$_6$;
R$_4$ is hydrogen, —C(O)R$_5$, or —CH$_2$OC(O)R$_5$;
R$_5$ is alkyl, alkoxy, or aryl, each optionally substituted with 0, 1, or multiple R$_6$;
R$_6$ is hydrogen, alkyl, aryl, halo, acyloxy, alkenyl, alkoxy, heteroaryl, heterocyclyl, or thioalkyl, each optionally substituted with 0, 1, or multiple R$_7$; and
R$_7$ is hydrogen, alkyl, aryl, or halo.

2. A compound according to claim 1, wherein X and Y are hydrogen.
3. A compound according to claim 2, wherein R$_1$ is chosen from alkyl or aryl, each optionally substituted with 0, 1 or multiple R$_6$.
4. A compound according to claim 2, wherein R$_2$ is chosen from alkyl or aryl, each optionally substituted with 0, 1 or multiple R$_6$.
5. A compound according to claim 1, wherein X is C(O)R$_3$ and Y is hydrogen.
6. A compound according to claim 5, wherein R$_1$ is chosen from alkyl or aryl, each optionally substituted with 0, 1 or multiple R$_6$.
7. A compound according to claim 5, wherein R$_2$ is chosen from alkyl or aryl, each optionally substituted with 0, 1 or multiple R$_6$.
8. A compound according to claim 1, wherein X is hydrogen and Y is Q.
9. A compound according to claim 8, wherein R$_1$ is chosen from alkyl or aryl, each optionally substituted with 0, 1 or multiple R$_6$.
10. A compound according to claim 8, wherein R$_2$ is chosen from alkyl or aryl, each optionally substituted with 0, 1 or multiple R$_6$.
11. A compound according to claim 9, wherein R$_4$ is hydrogen.
12. A compound according to claim 9, wherein R$_4$ is —C(O)R$_5$ or —CH$_2$OC(O)R$_5$.
13. A compound according to claim 12, wherein R$_5$ is chosen from alkyl or alkoxy, each optionally substituted with 0, 1, or multiple R$_6$.
14. A compound according to claim 13, wherein R$_5$ is chosen from —CH$_3$, —CH(CH$_3$)$_2$, —CH$_2$OCH$_2$CH$_3$, or —CH$_2$CH$_2$OCH$_3$.
15. A composition for the control of a fungal pathogen including at least one of the compounds of claim 1 and a phytologically acceptable carrier material.
16. A composition for the control of a fungal pathogen including mixtures of at least one of the compounds of claim 1 with other pesticides including fungicides, insecticides, nematocides, miticides, arthropodicides, bactericides, and combinations thereof.
17. The composition according to claim 16, further comprising an azole fungicide selected from the group consisting of epoxiconazole, tebuconazole, fluquinconazole, flutriafol, metconazole, myclobutanil, cycproconazole, prothioconazole, and propiconazole.
18. The composition according to claim 16, further comprising a strobilurin fungicide selected from the group consisting of trifloxystrobin, pyraclostrobin, orysastrobin, fluoxastrobin, and azoxystrobin.
19. The composition according to claim 16, further comprising a succinate dehydrogenase inhibiting (SDHI) fungicide selected from the group consisting of fluxapyroxad, boscalid, penthiopyrad, benzovindiflupyr, bixafen, flupyram, and isopyrazam.
20. The compositions according to claim 15 wherein the fungal pathogen is one of Leaf Blotch of Wheat (*Mycosphaerella graminicola*; anamorph: *Septoria tritici*), Wheat Brown Rust (*Puccinia triticina*), Stripe Rust (*Puccinia striiformis*), Scab of Apple (*Venturia inaequalis*), Blister Smut of Maize (*Ustilago maydis*), Powdery Mildew of Grapevine (*Uncinula necator*), Barley Scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (Blumeria

*graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

21. The composition according to claim 20 wherein the fungal pathogen is one of Leaf Blotch of Wheat (*Septoria tritici*), Wheat Brown Rust (*Puccinia triticina*), and Rust of Soybean (*Phakopsora pachyrhizi*).

22. A method for the control and prevention of fungal attack on a plant, the method including the step of: Applying a fungicidally effective amount of at least one of the compounds of claim 1 to at least one of the plant, an area adjacent to the plant, soil adapted to support growth of the plant, a root of the plant, and foliage of the plant.

23. A method for the control and prevention of fungal attack on a plant, the method including the step of: Applying a fungicidally effective amount of at least one of the compositions according to claim 15 to at least one of the plant, an area adjacent to the plant, soil adapted to support growth of the plant, a root of the plant, and foliage of the plant.

* * * * *